United States Patent [19]

Sakurai et al.

[11] Patent Number: 5,391,144
[45] Date of Patent: Feb. 21, 1995

[54] ULTRASONIC TREATMENT APPARATUS

[75] Inventors: Tomohisa Sakurai; Hideo Nagazumi; Kazuya Hijii; Toshihiko Suzuta; Masahiro Kudo, all of Hachioji; Kenji Yoshino, Tama; Tetsumaru Kubota, Hachioji; Tatsuya Kubota, Sagamihara; Hiroaki Kagawa, Hachioji; Yuichi Ikeda, Hachioji; Mitsumasa Okada, Hachioji; Hitoshi Karasawa, Hachioji; Tadao Hagino, Yokohama, all of Japan

[73] Assignee: Olympus Optical Co., Ltd., Tokyo, Japan

[21] Appl. No.: 94,910

[22] Filed: Jul. 20, 1993

Related U.S. Application Data

[63] Continuation of Ser. No. 680,099, Apr. 2, 1991, abandoned, which is a continuation-in-part of Ser. No. 628,650, Dec. 14, 1990, abandoned.

[30] Foreign Application Priority Data

| Feb. 2, 1990 | [JP] | Japan | 2-22241 |
| Feb. 13, 1990 | [JP] | Japan | 2-32099 |
| Mar. 27, 1990 | [JP] | Japan | 2-77375 |
| Mar. 28, 1990 | [JP] | Japan | 2-79716 |
| Mar. 29, 1990 | [JP] | Japan | 2-78918 |
| Mar. 29, 1990 | [JP] | Japan | 2-78919 |
| Apr. 3, 1990 | [JP] | Japan | 2-89685 |
| Jun. 15, 1990 | [JP] | Japan | 2-155522 |
| Jun. 29, 1990 | [JP] | Japan | 2-170232 |
| Jul. 24, 1990 | [JP] | Japan | 2-193802 |
| Jul. 31, 1990 | [JP] | Japan | 2-201132 |
| Oct. 23, 1990 | [JP] | Japan | 2-283322 |
| Oct. 26, 1990 | [JP] | Japan | 2-286976 |

[51] Int. Cl.$^6$ .............................. A61B 17/36
[52] U.S. Cl. .......................... 604/22; 128/6; 606/1; 606/169; 607/97
[58] Field of Search .............. 128/24 AA, 4, 6; 433/99, 100, 119; 604/22; 606/169, 1; 607/97; 601/2-3

[56] References Cited

U.S. PATENT DOCUMENTS

| 3,809,977 | 5/1974 | Balamuth et al. | 128/24 AA |
| 3,924,335 | 12/1975 | Balamuth et al. | |
| 3,990,452 | 11/1976 | Murry et al. | 128/24 AA |
| 4,750,902 | 6/1988 | Wuchinich et al. | |
| 4,768,496 | 9/1988 | Kreizman et al. | |
| 4,816,018 | 3/1989 | Parisi | 128/24 AA |
| 4,823,775 | 4/1989 | Rindt . | |
| 4,979,952 | 12/1990 | Kubota et al. | |
| 5,047,043 | 9/1991 | Kubota et al. | |

FOREIGN PATENT DOCUMENTS

| 3707403A1 | 9/1987 | Germany . |
| 3807004A1 | 9/1988 | Germany . |
| WO87/01276 | 3/1987 | WIPO . |

Primary Examiner—Ruth S. Smith
Attorney, Agent, or Firm—Frishauf, Holtz, Goodman & Woodward

[57] ABSTRACT

An ultrasonic treatment apparatus comprises at least one hand piece, a plurality of probes, and an ultrasonic drive device. The hand piece has an ultrasonic oscillation device for generating ultrasonic vibration. Each probe is adapted to be attached to the hand piece and designed to transmit the ultrasonic vibration generated by the hand piece. The ultrasonic drive device is connected to the hand piece, for driving the ultrasonic oscillation device.

70 Claims, 76 Drawing Sheets

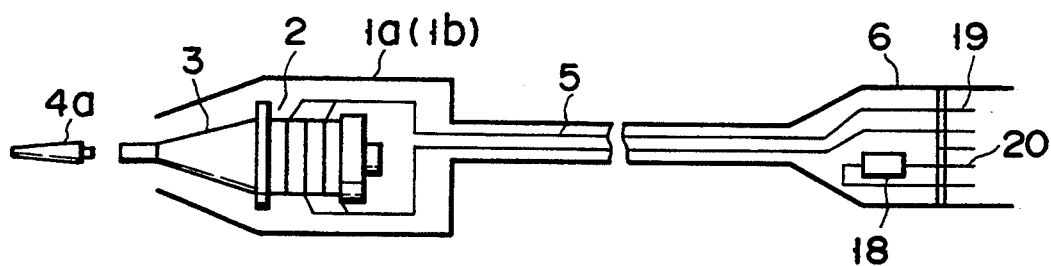
F I G. 2
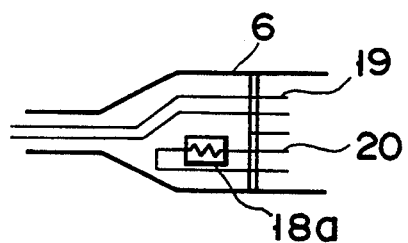
F I G. 3A
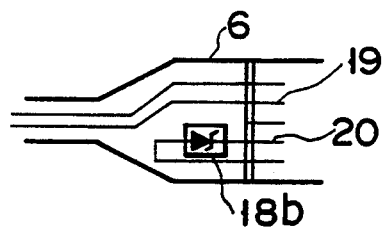
F I G. 3B
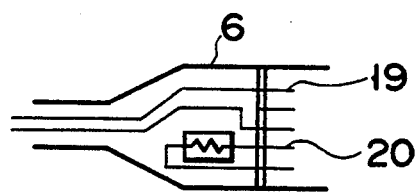
F I G. 3C

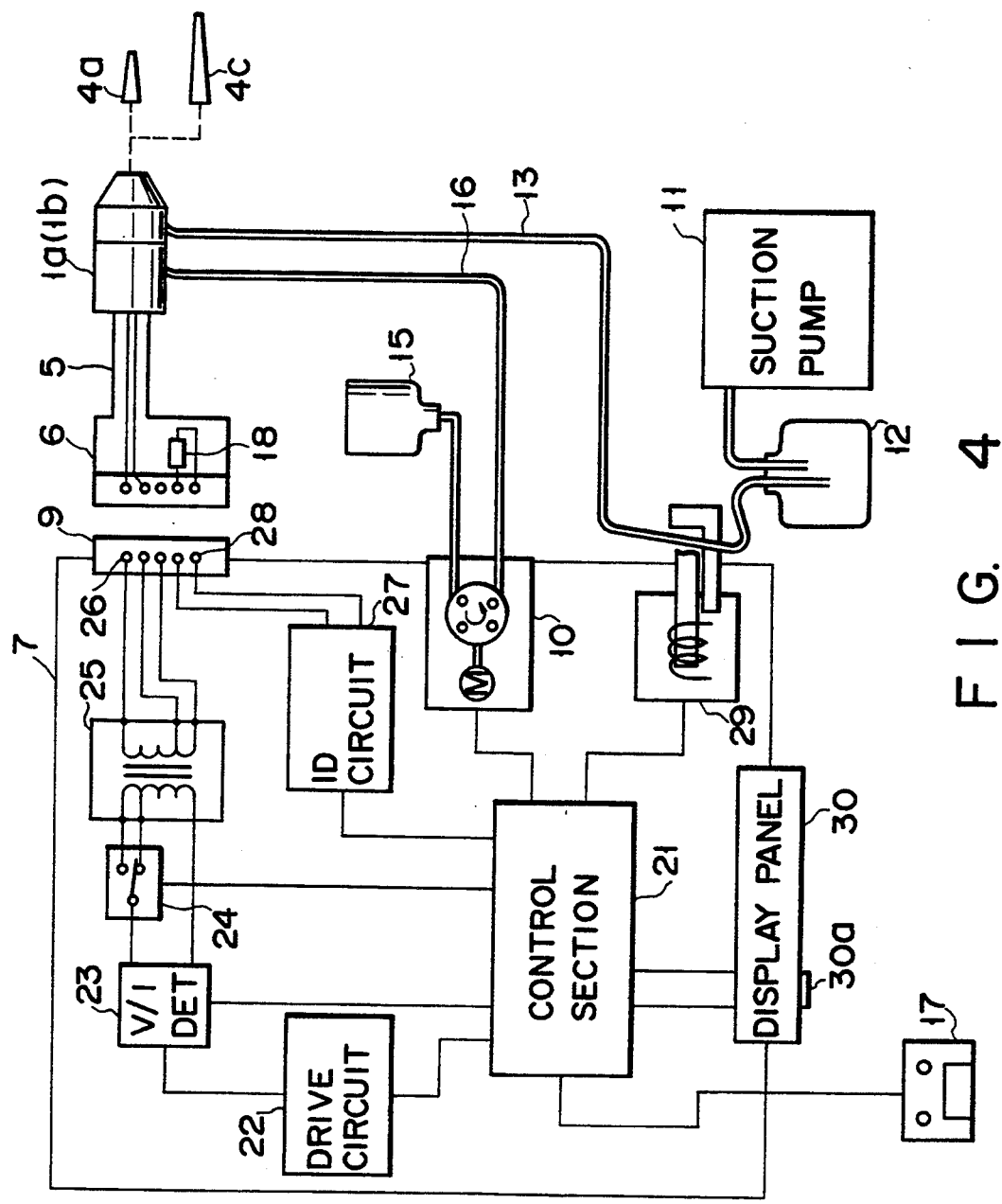
F I G. 4

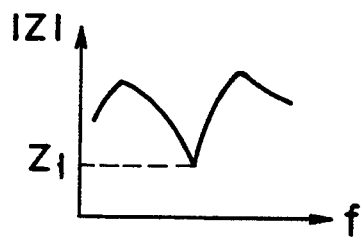 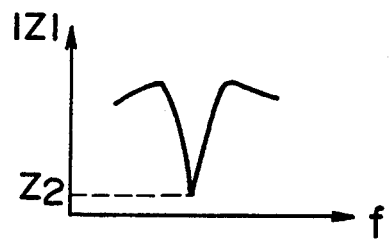
F I G.  5A    F I G.  5B
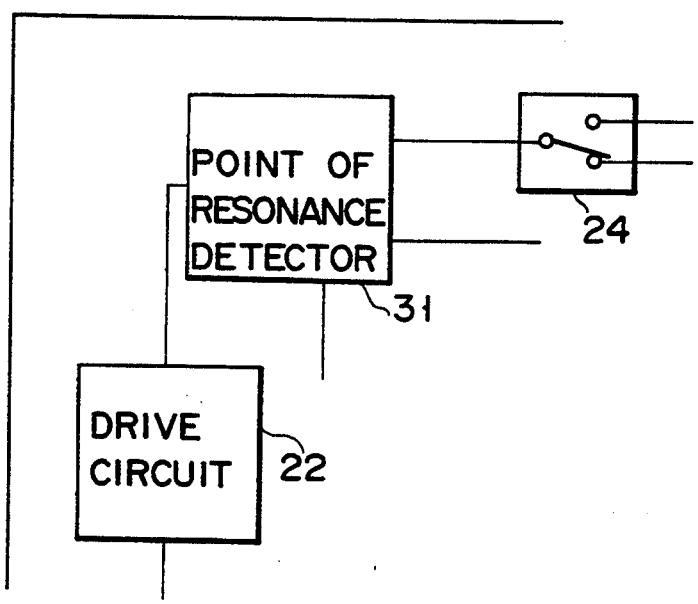
F I G.  6
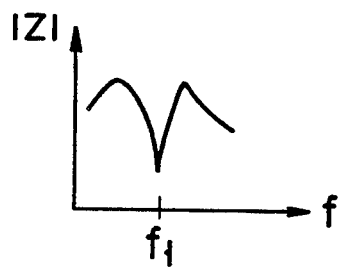 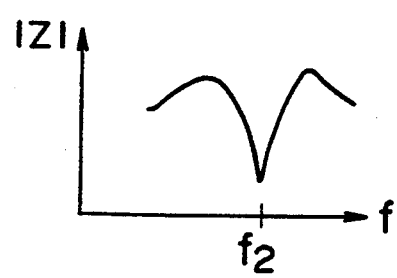
F I G.  7A    F I G.  7B

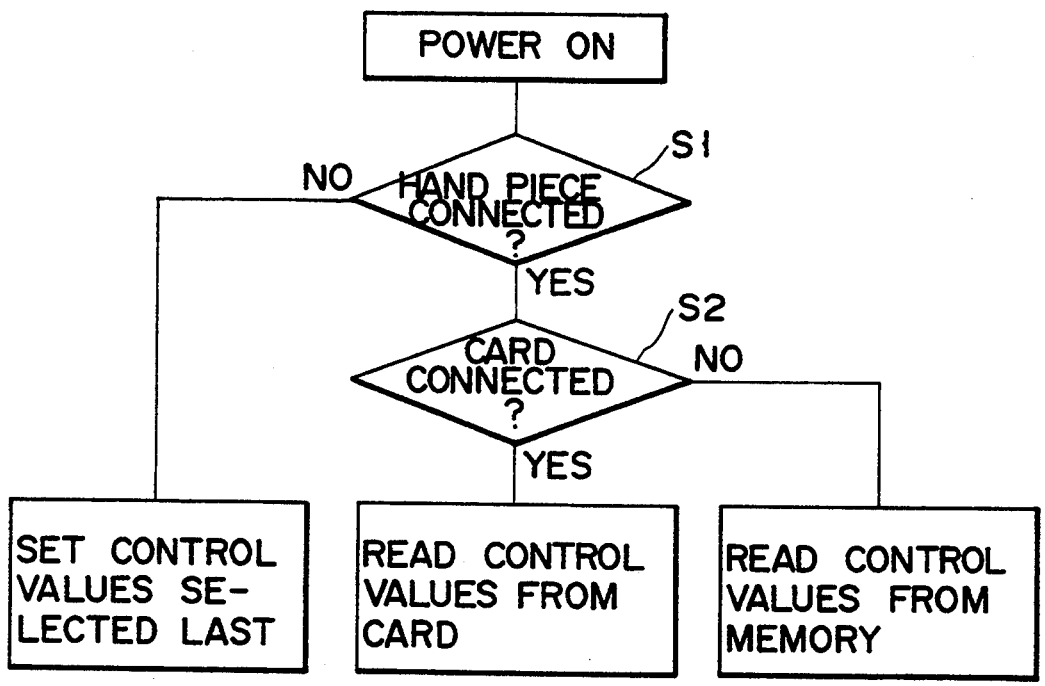
F I G. 11
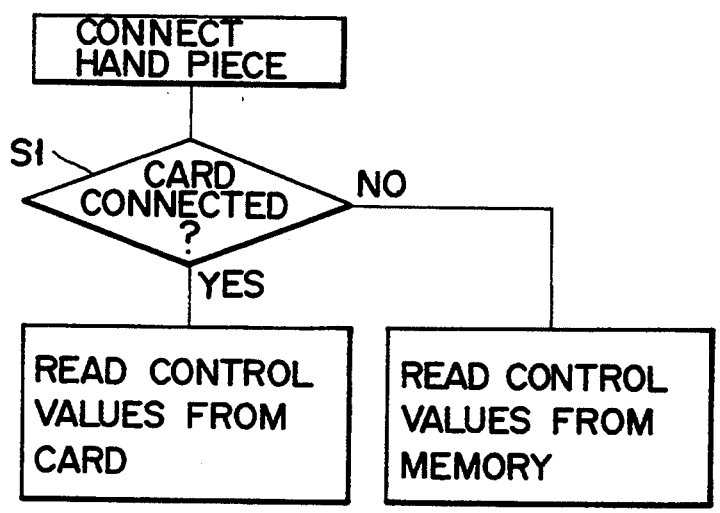
F I G. 12

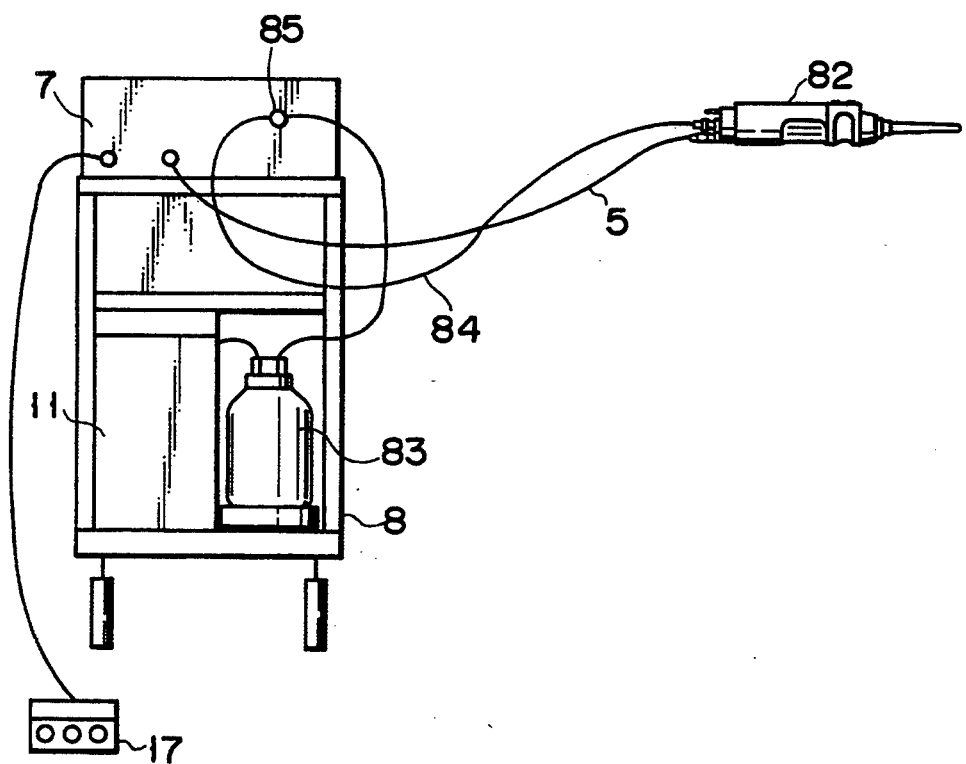
F I G. 15

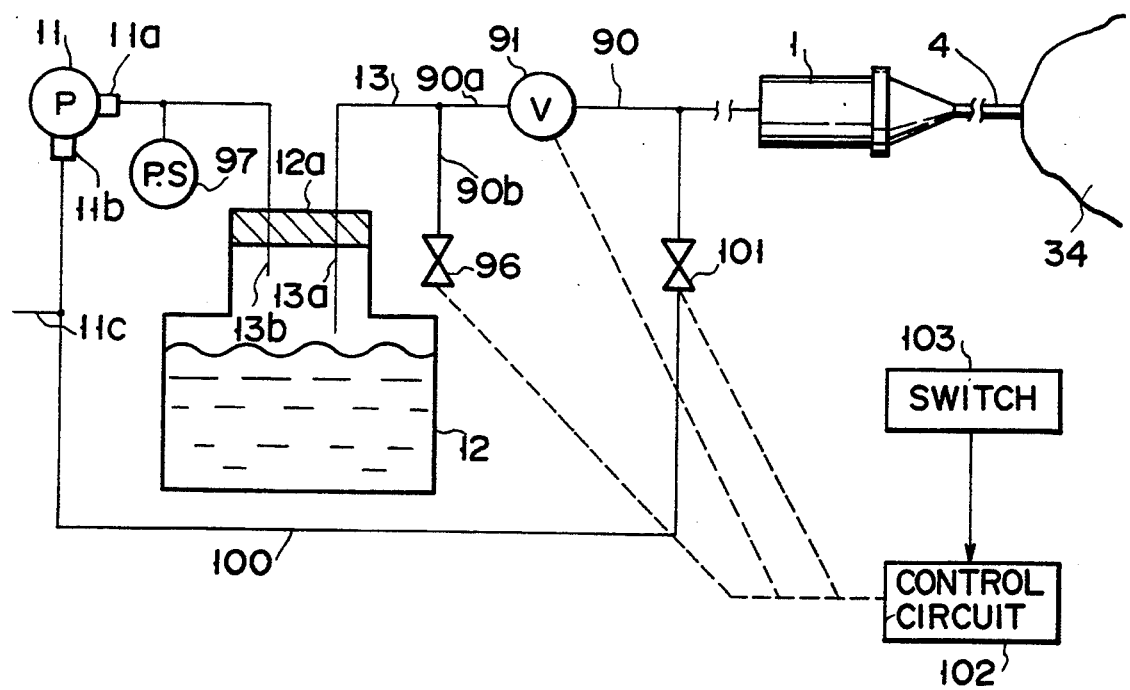
F I G. 18
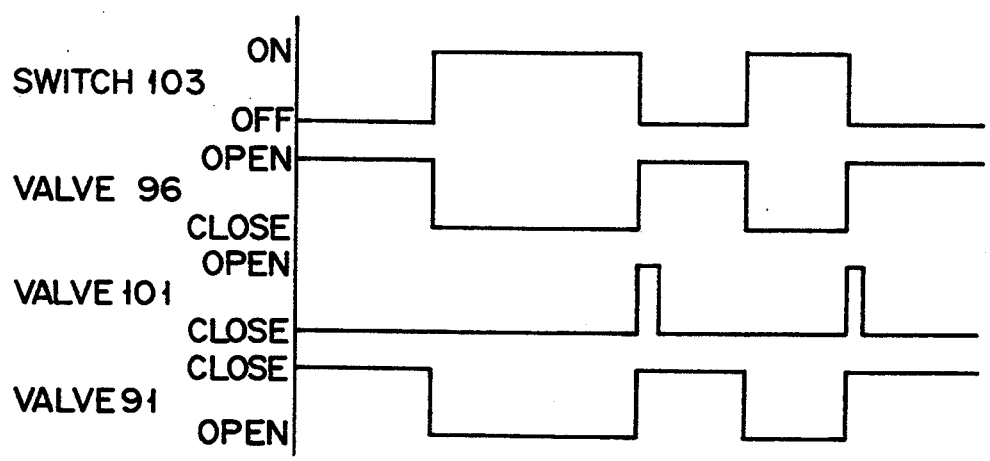
F I G. 19

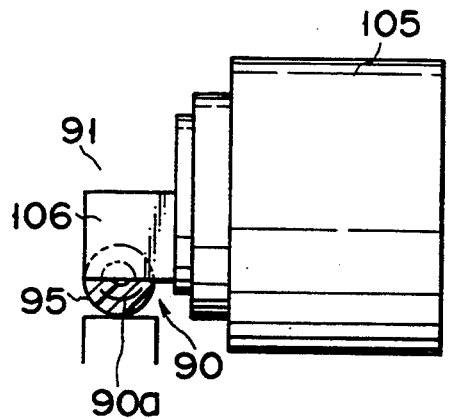
F I G. 22
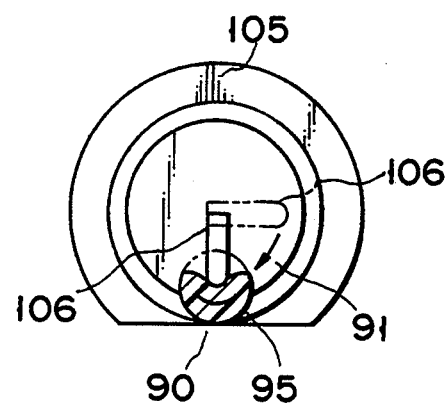
F I G. 23
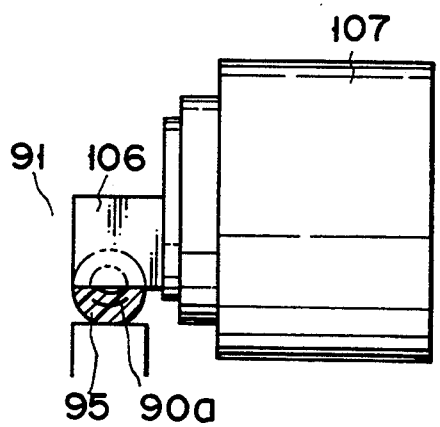
F I G. 24
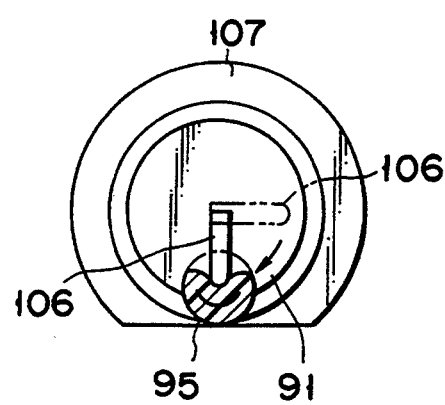
F I G. 25

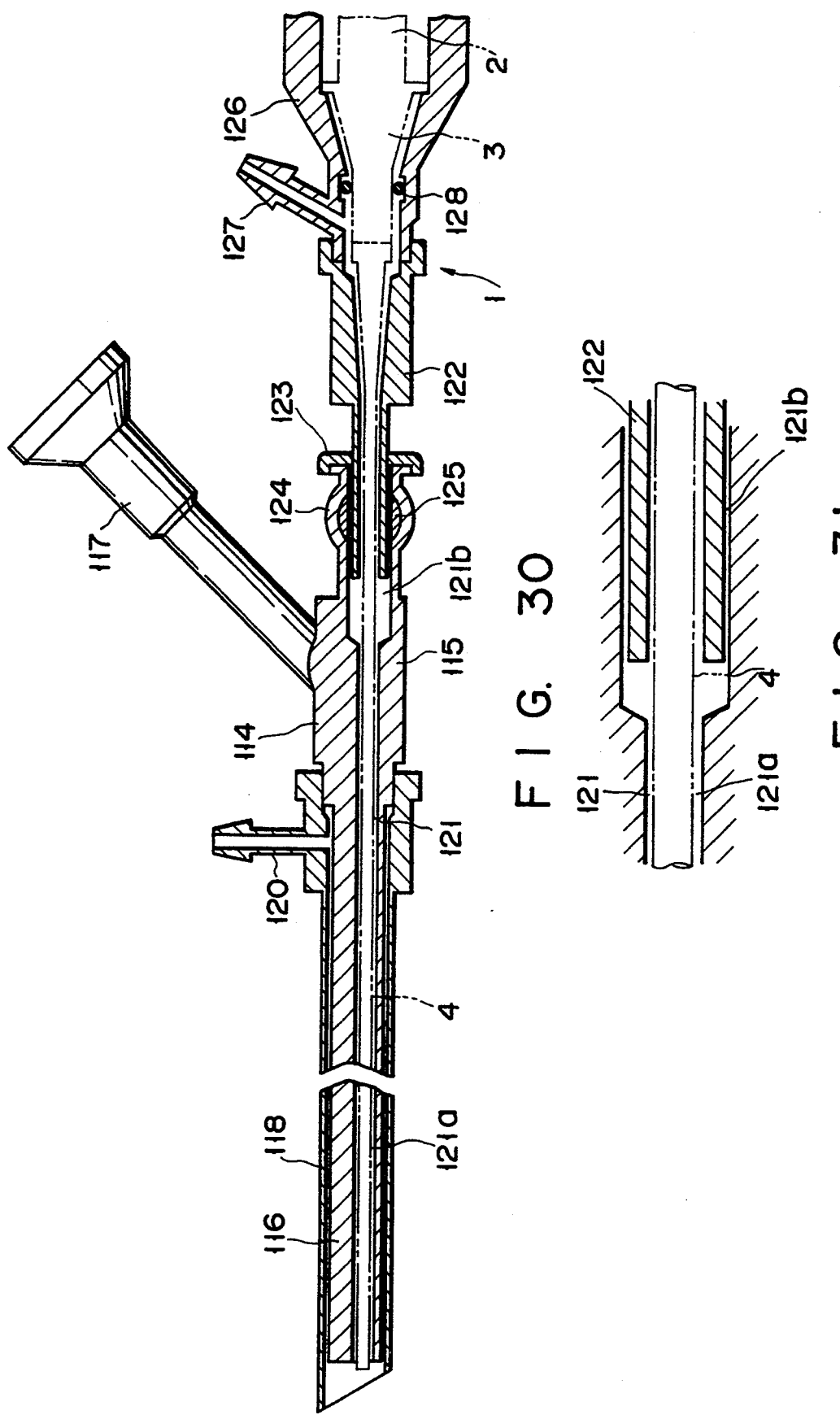

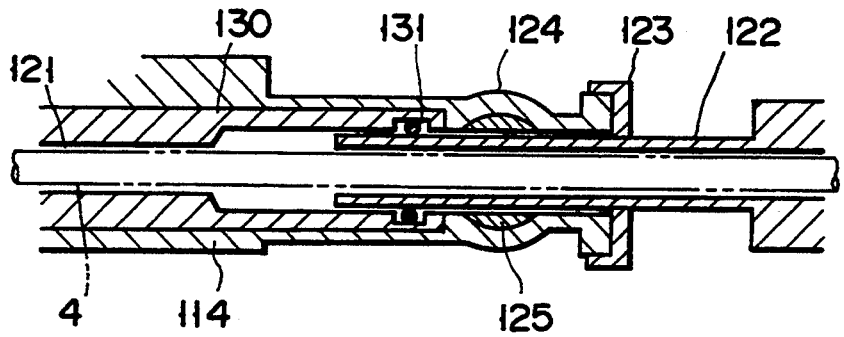
F I G. 32A
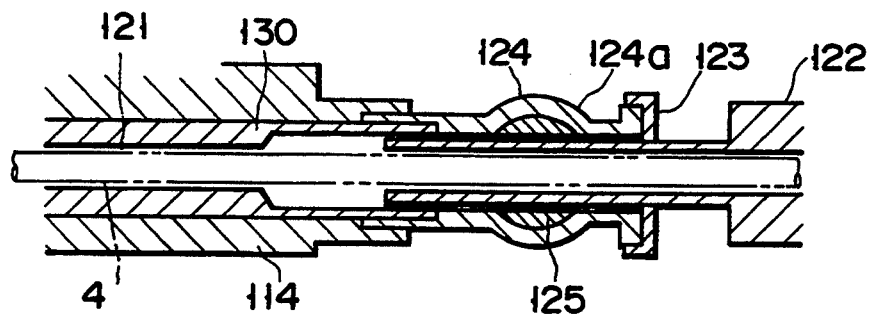
F I G. 32B
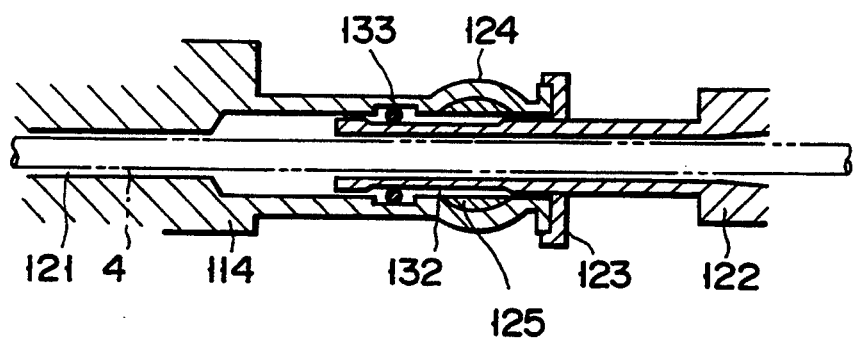
F I G. 32C

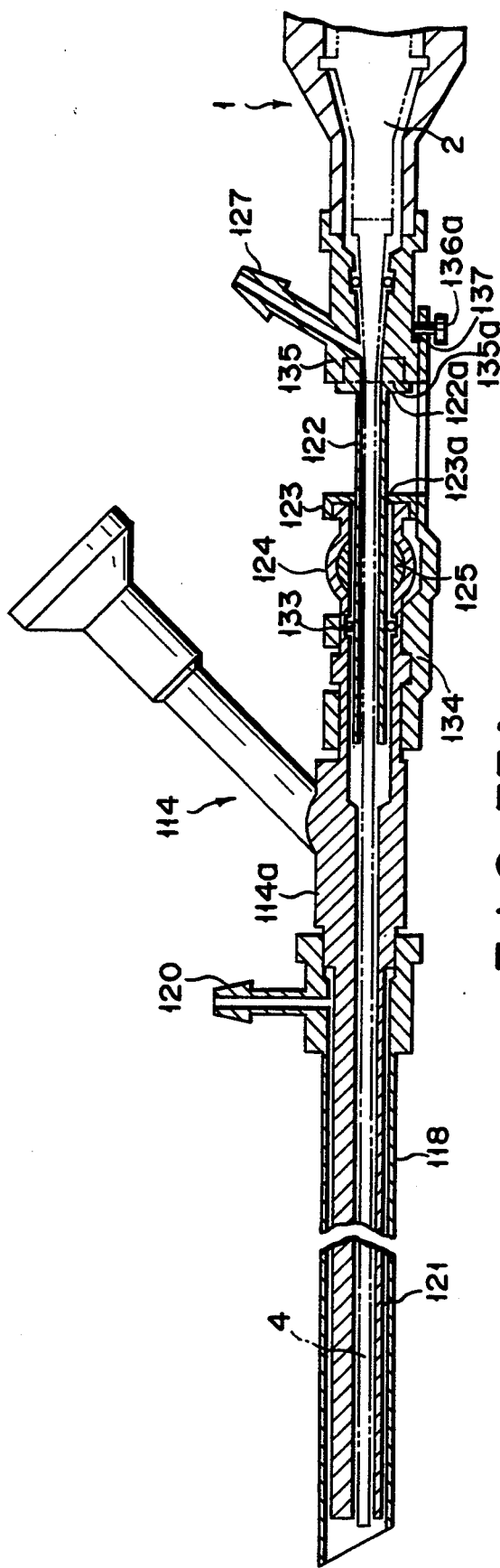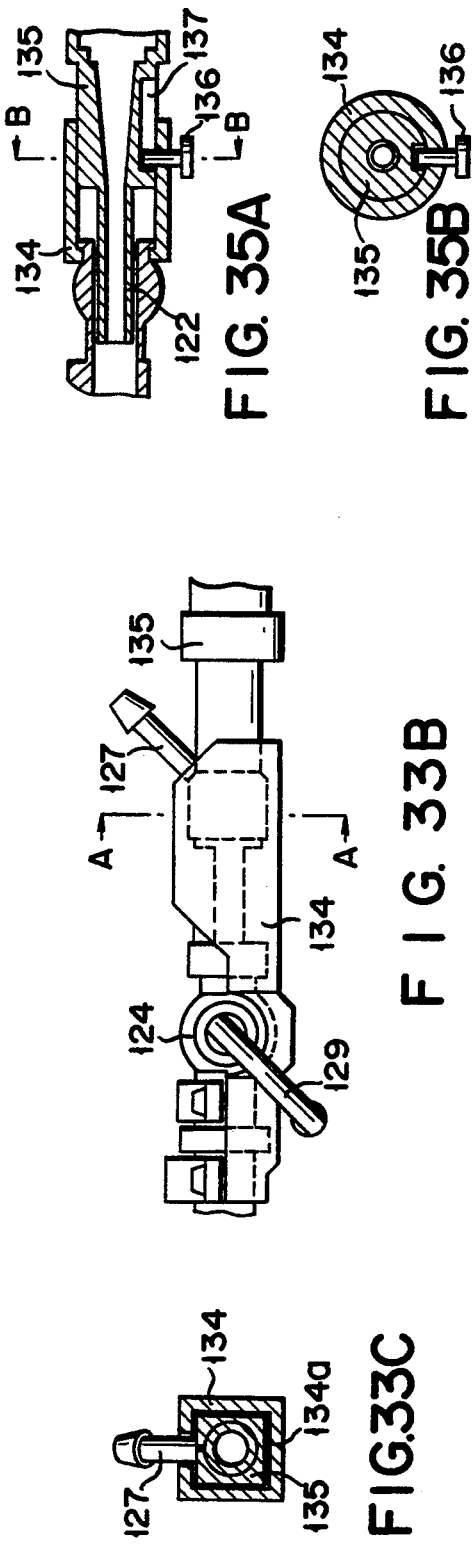

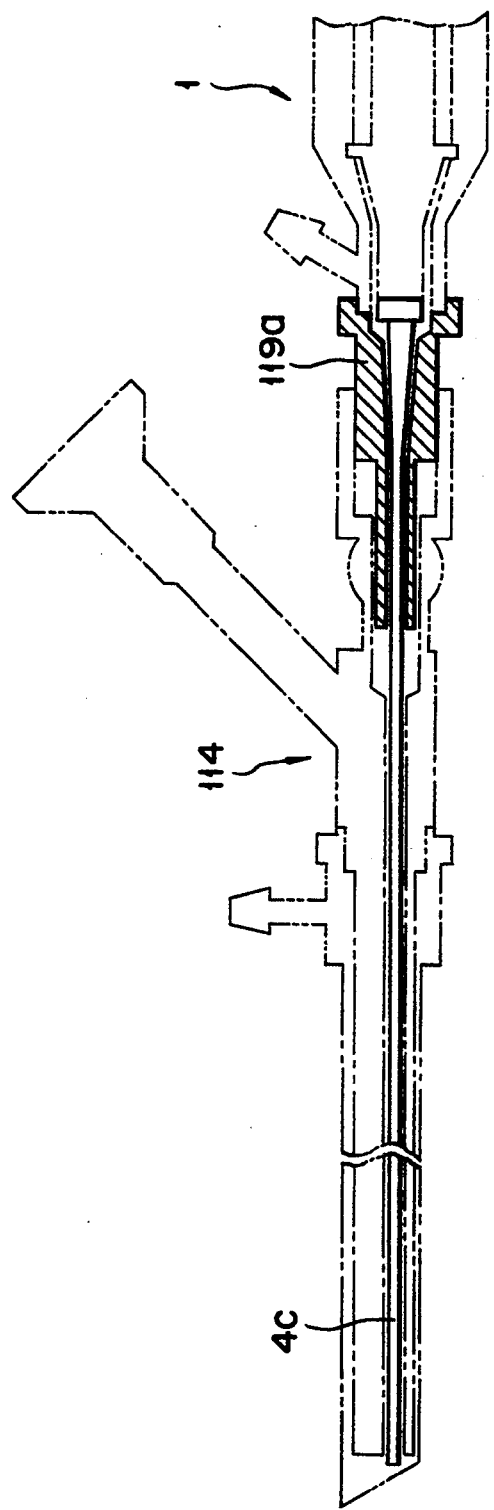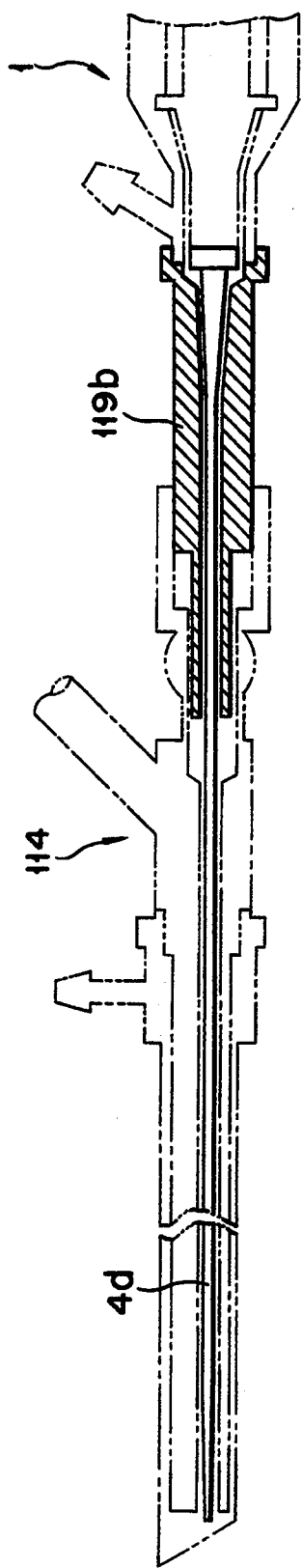
FIG. 34A
FIG. 34B

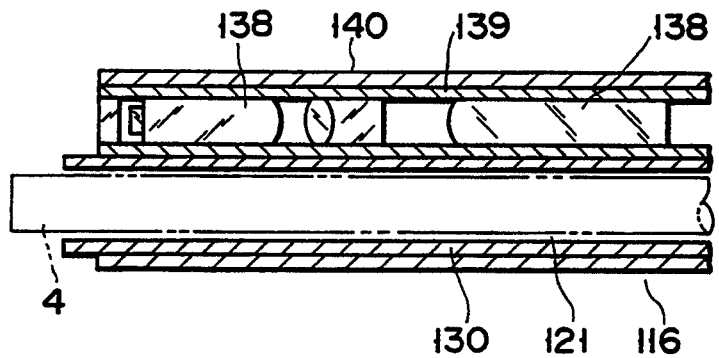 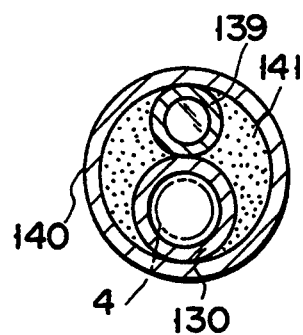
FIG. 36    FIG. 37
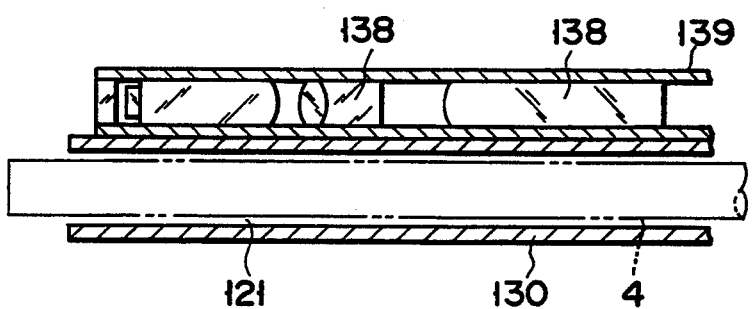 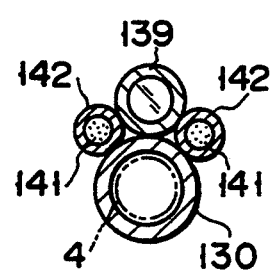
FIG. 38    FIG. 39

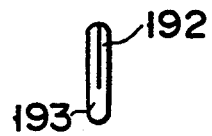 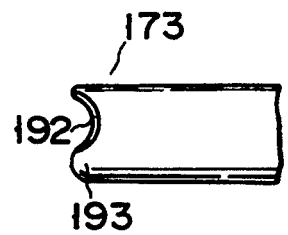
FIG. 46B     FIG. 46A
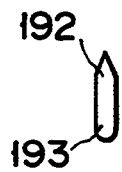 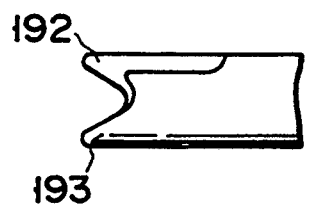
FIG. 46D     FIG. 46C
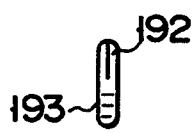 
FIG. 46F     FIG. 46E
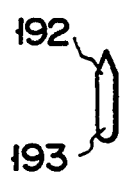 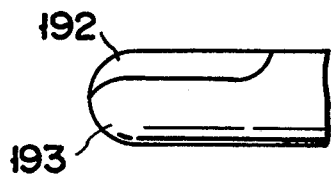
FIG. 46H     FIG. 46G

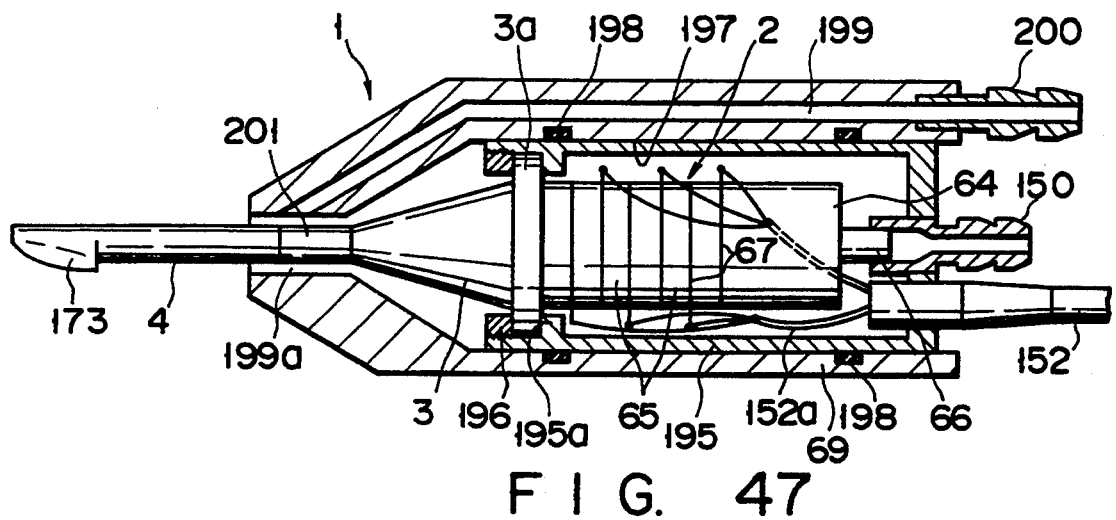
F I G. 47
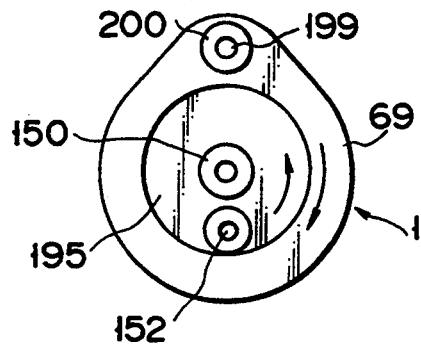
F I G. 48
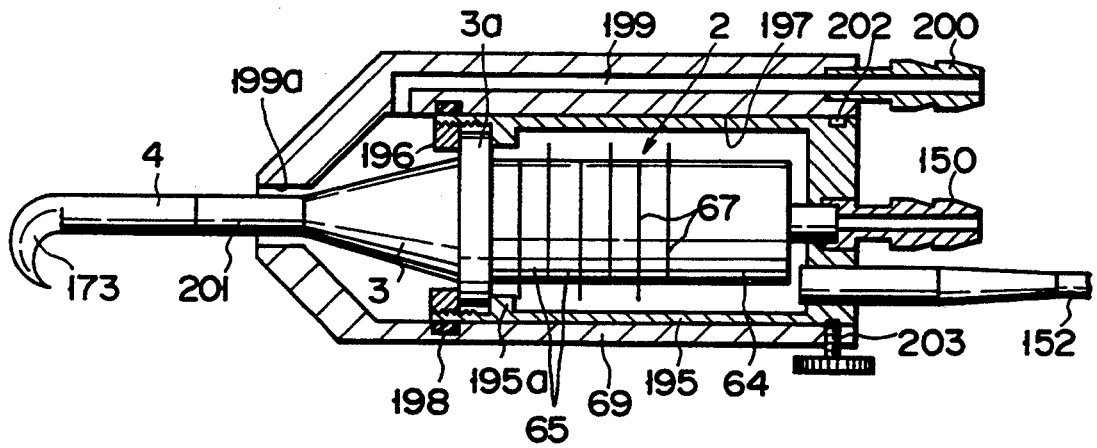
F I G. 49

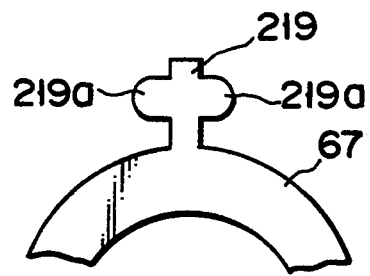
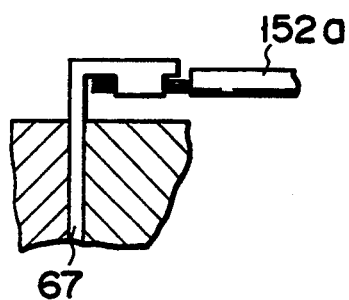
FIG. 57　　　FIG. 58
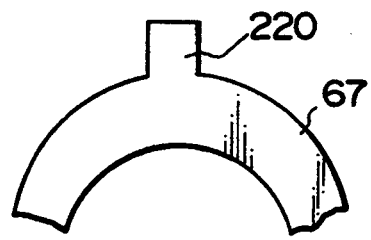
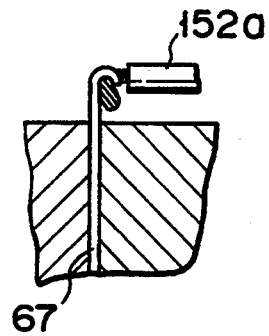
FIG. 59　　　FIG. 60

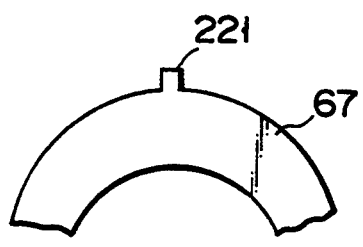
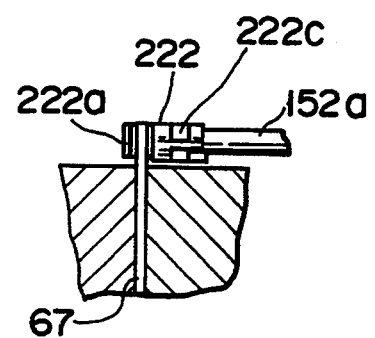
F I G. 61   F I G. 62
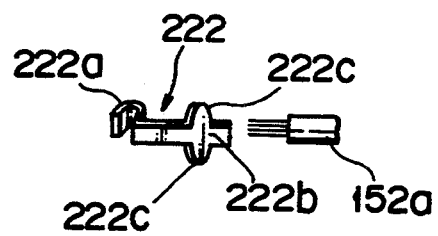
F I G. 63

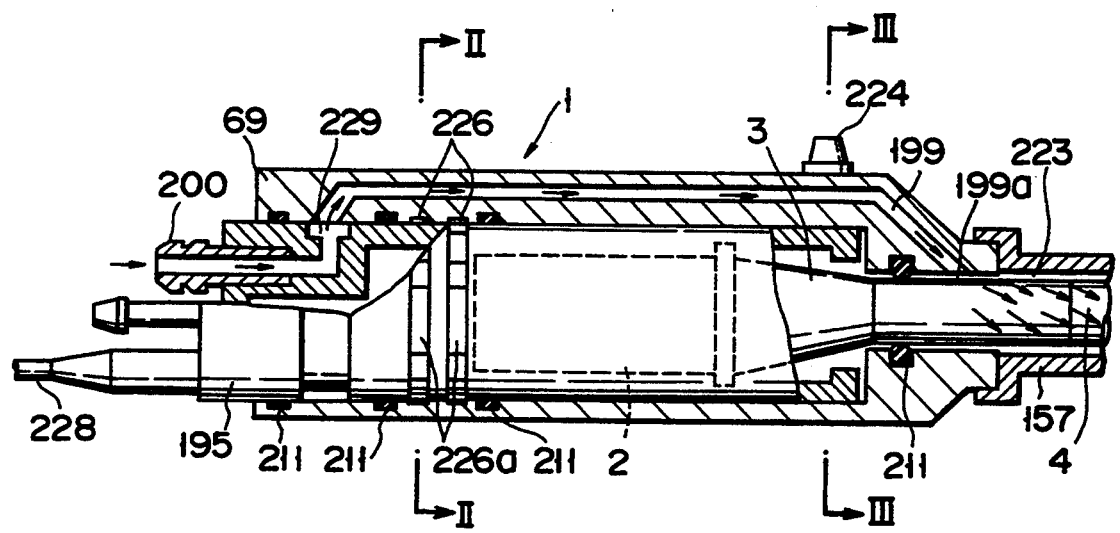
FIG. 64
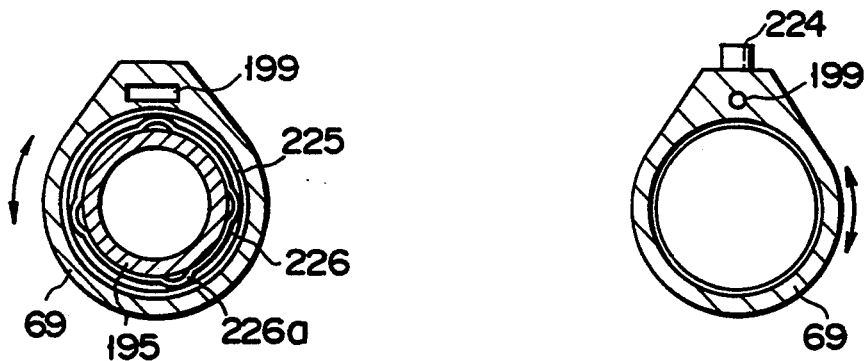
FIG. 65
FIG. 66
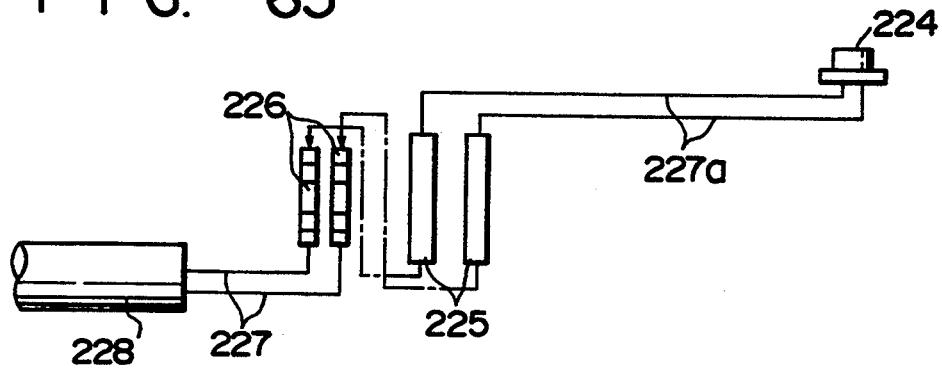
FIG. 67

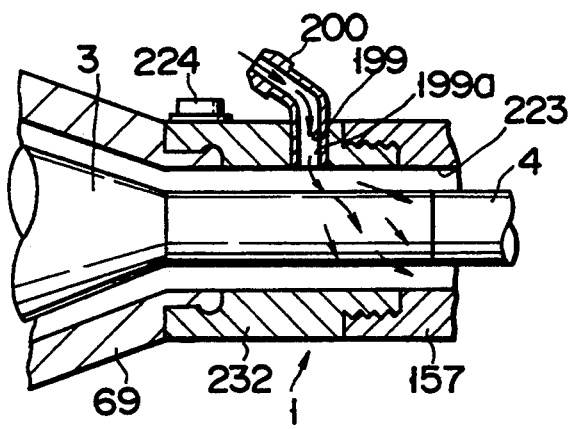
F I G. 72
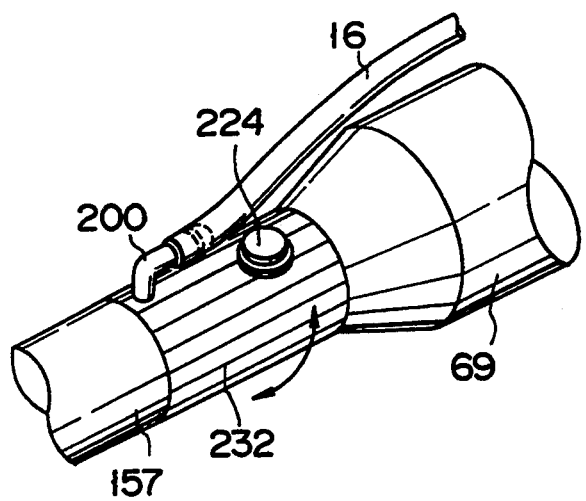
F I G. 73
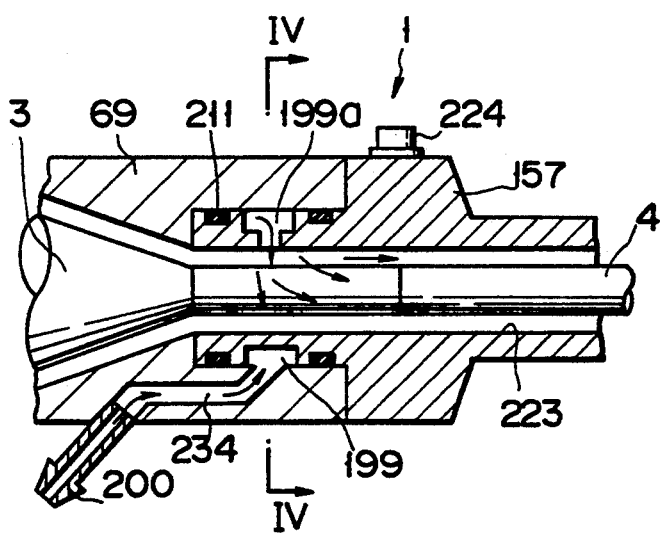
F I G. 74
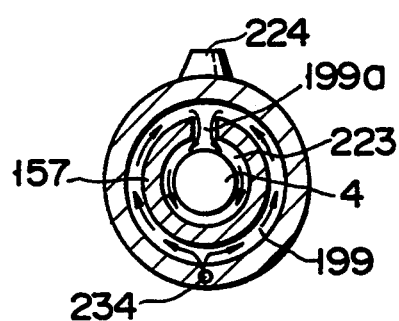
F I G. 75

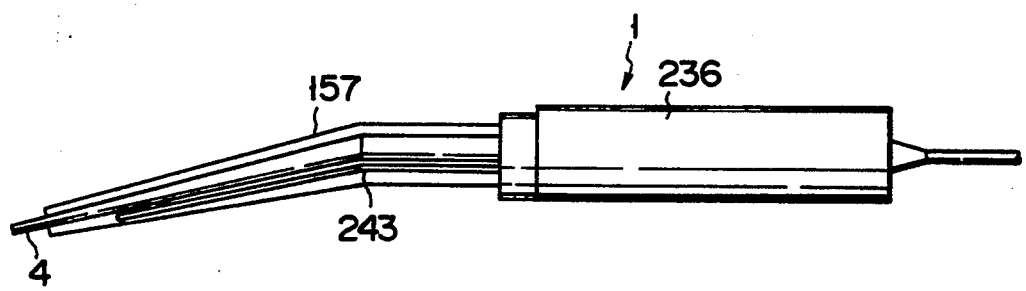
F I G. 81
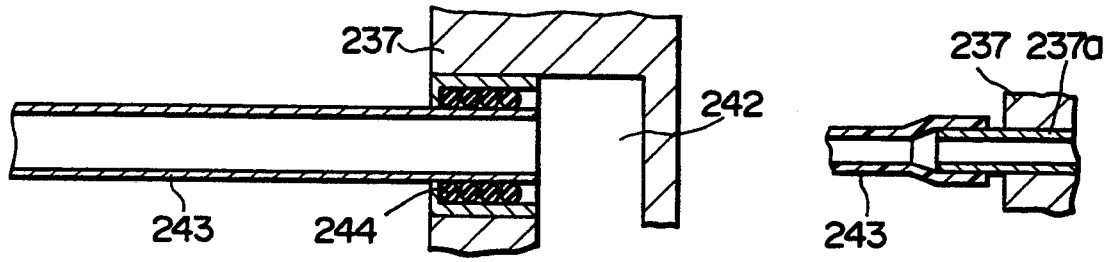
F I G. 82     F I G. 83
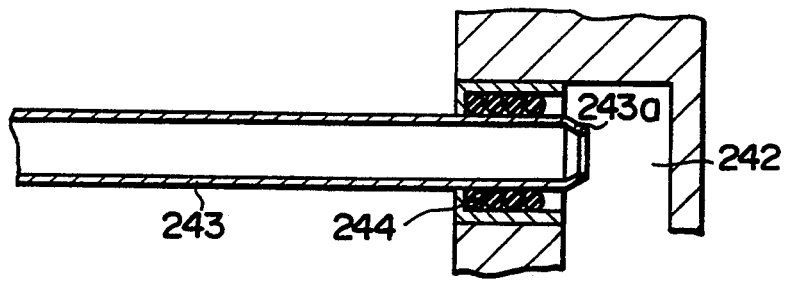
F I G. 84
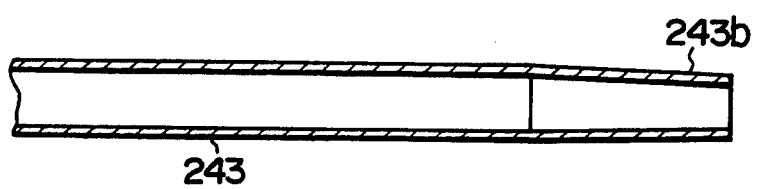
F I G. 85

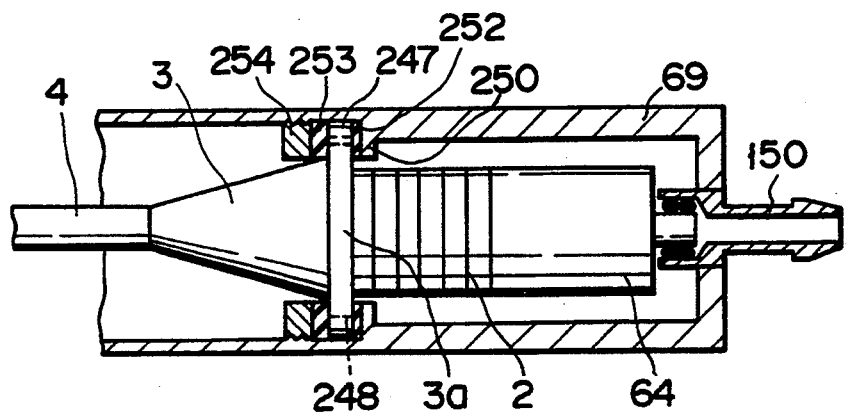
F I G. 86
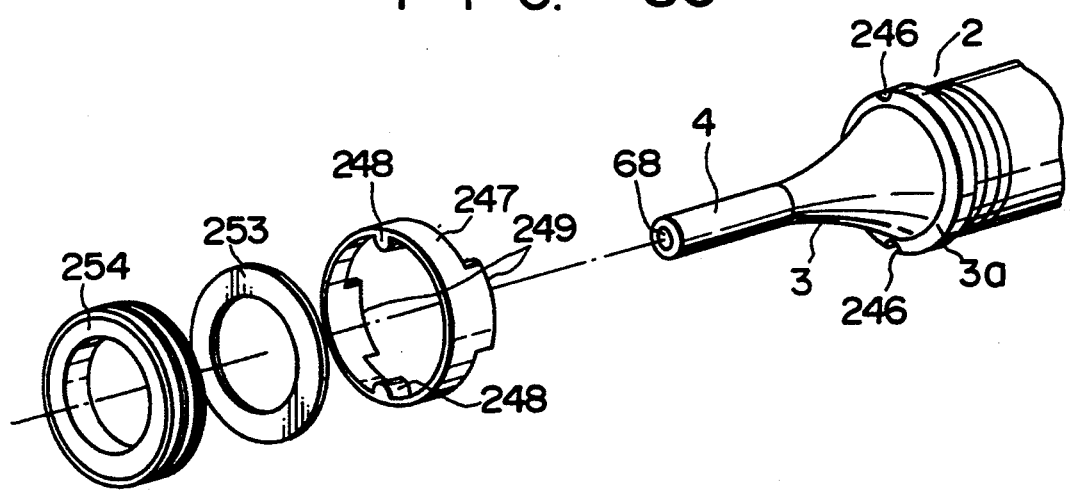
F I G. 87A
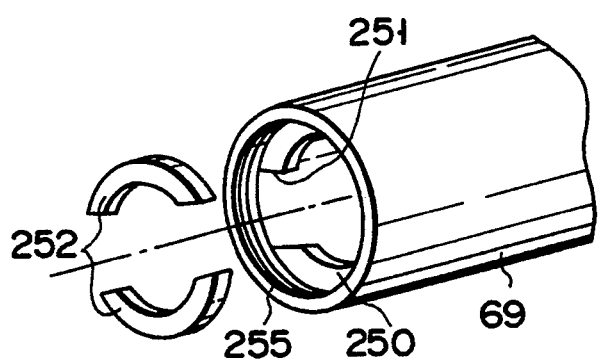
F I G. 87B

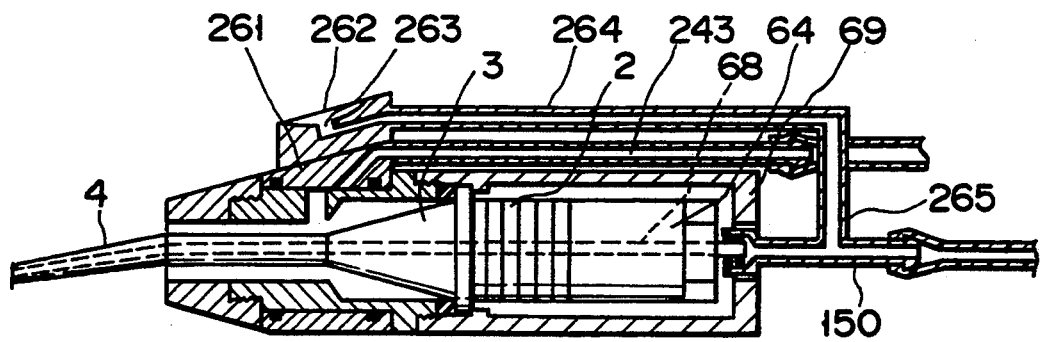
F I G. 94
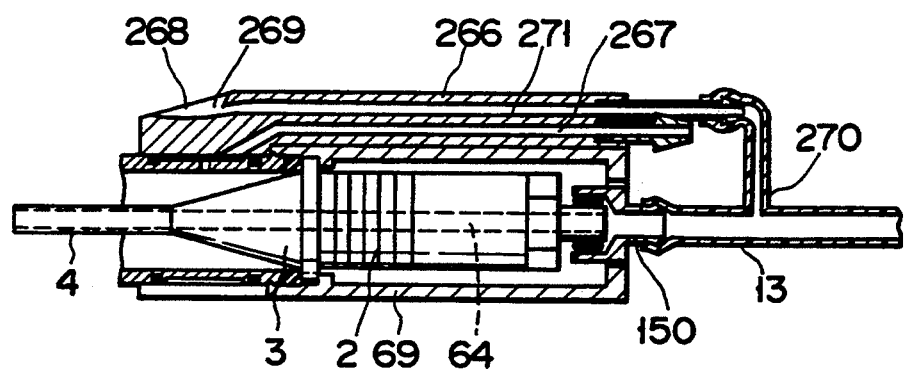
F I G. 95

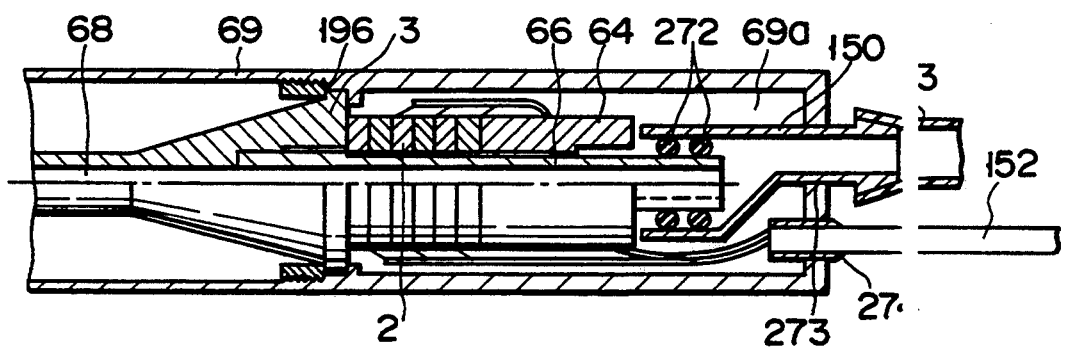
F I G. 96
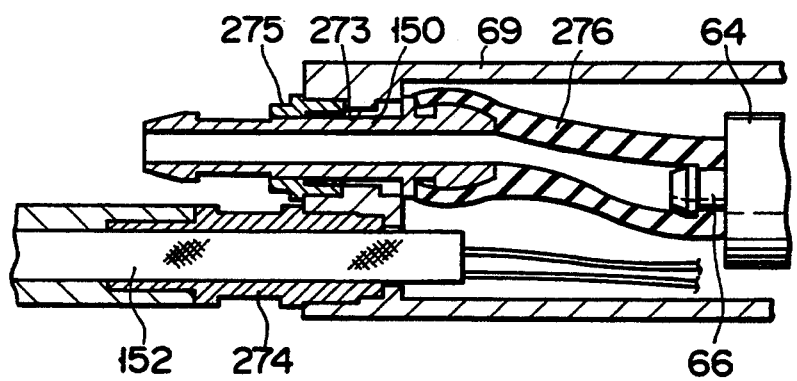
F I G. 97

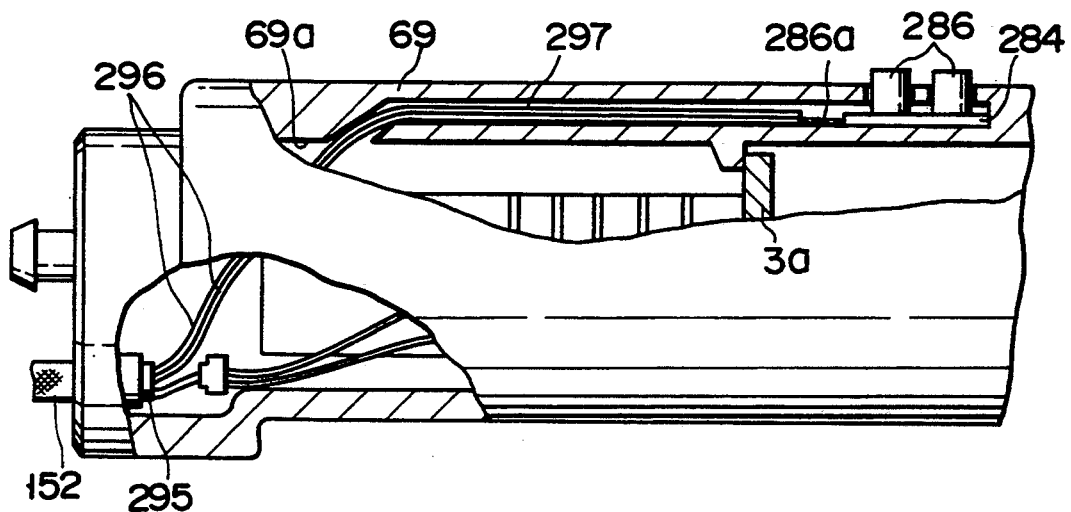
F I G. 100
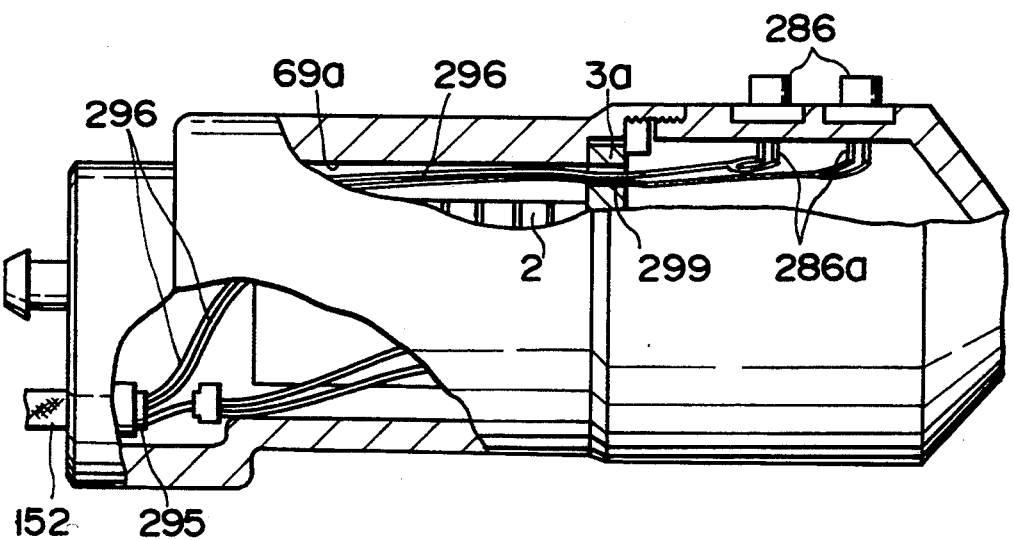
F I G. 101

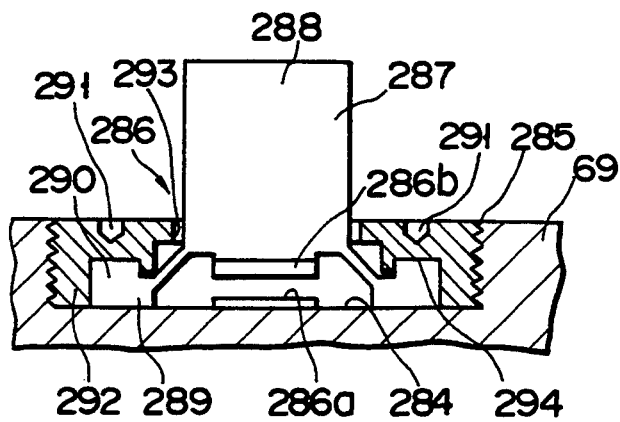
F I G. 102
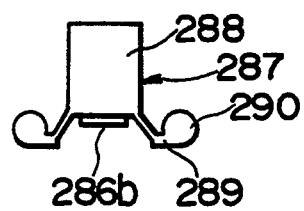
F I G. 103
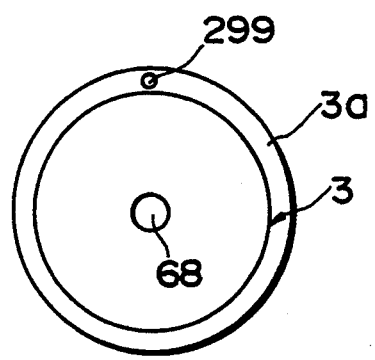     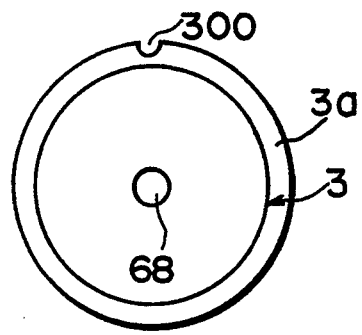
F I G. 104     F I G. 105

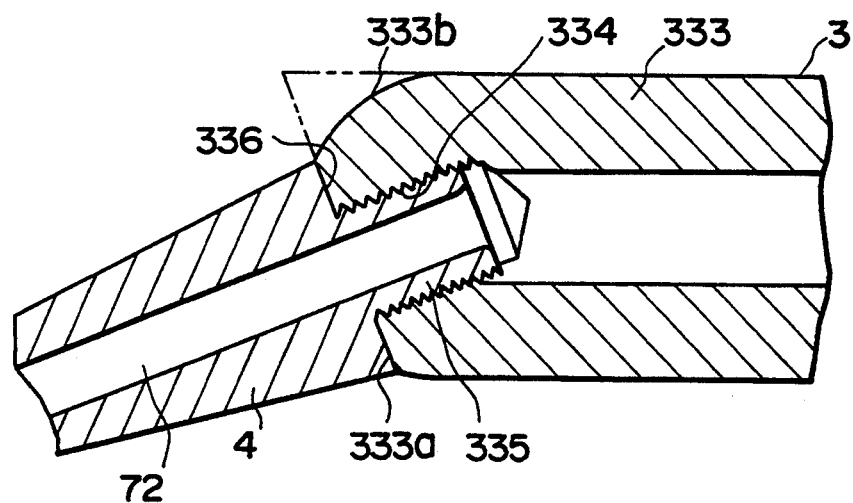
F I G. 108
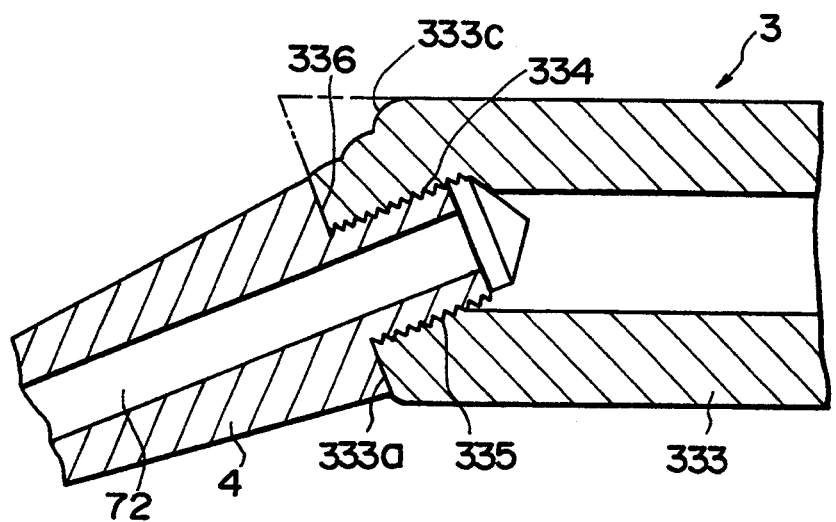
F I G. 109

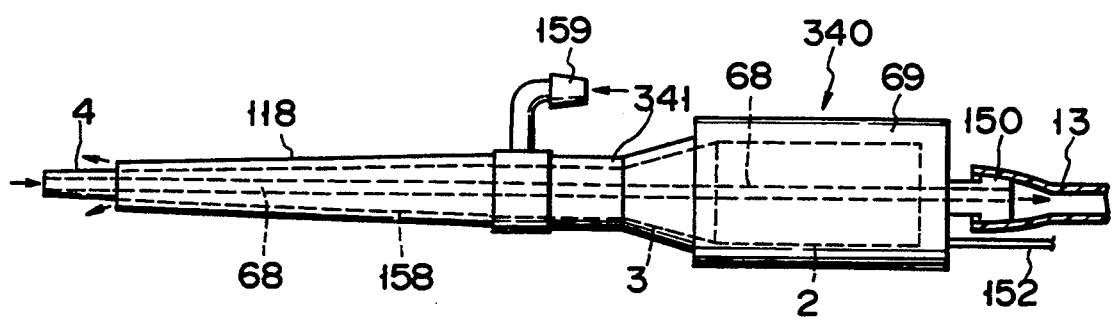
F I G. 111
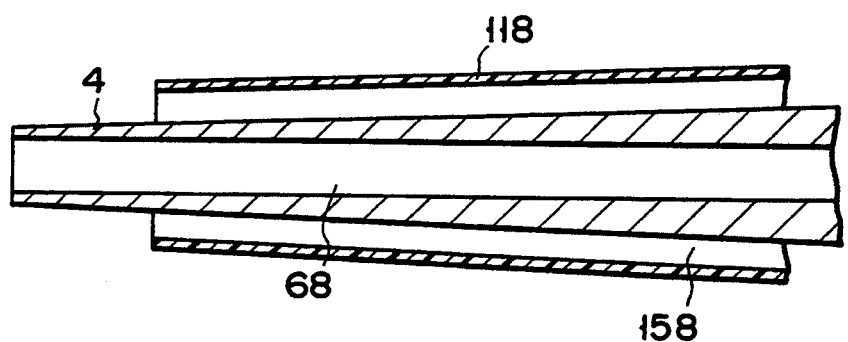
F I G. 112

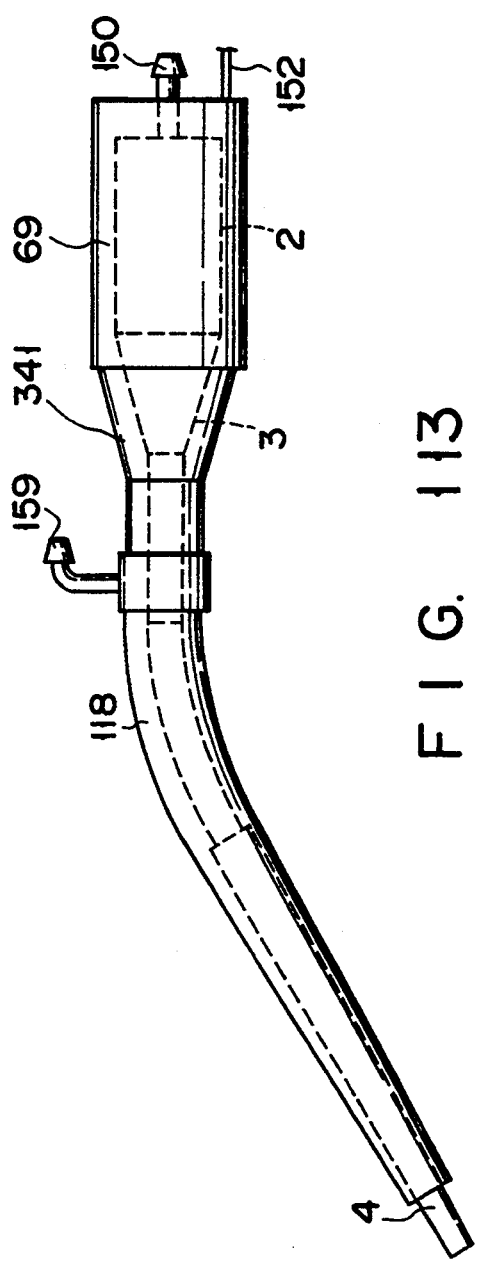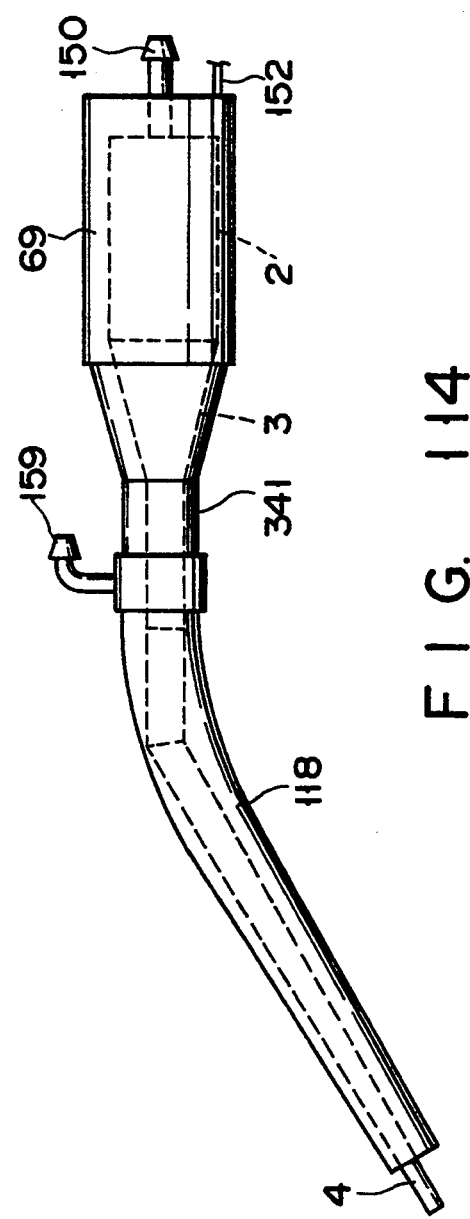

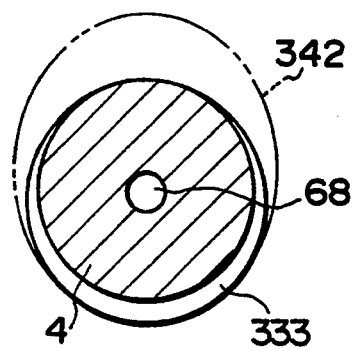
F I G. 117
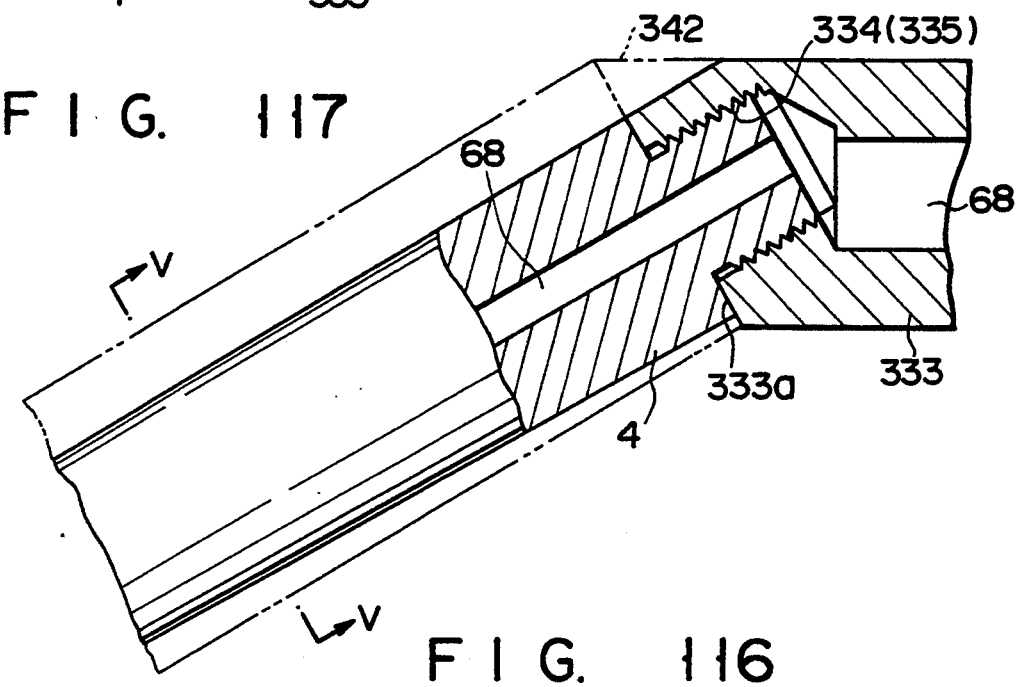
F I G. 116
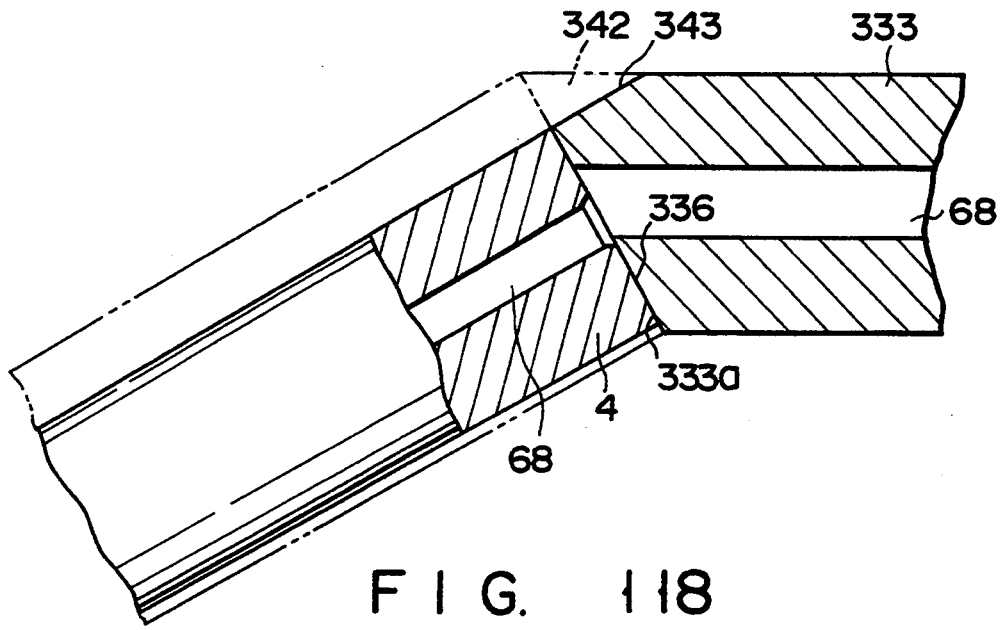
F I G. 118

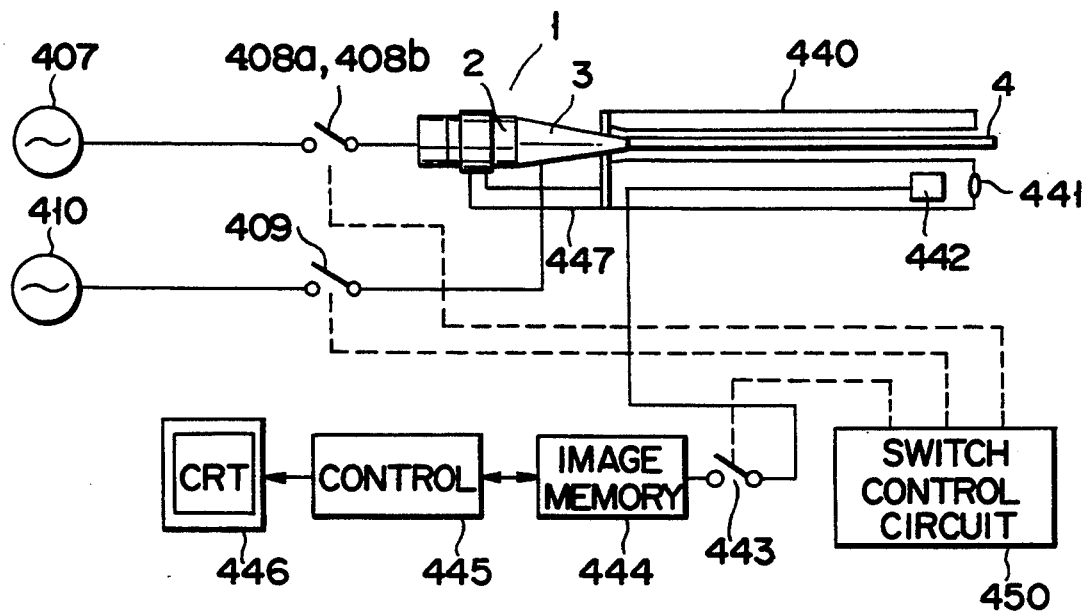
F I G. 125
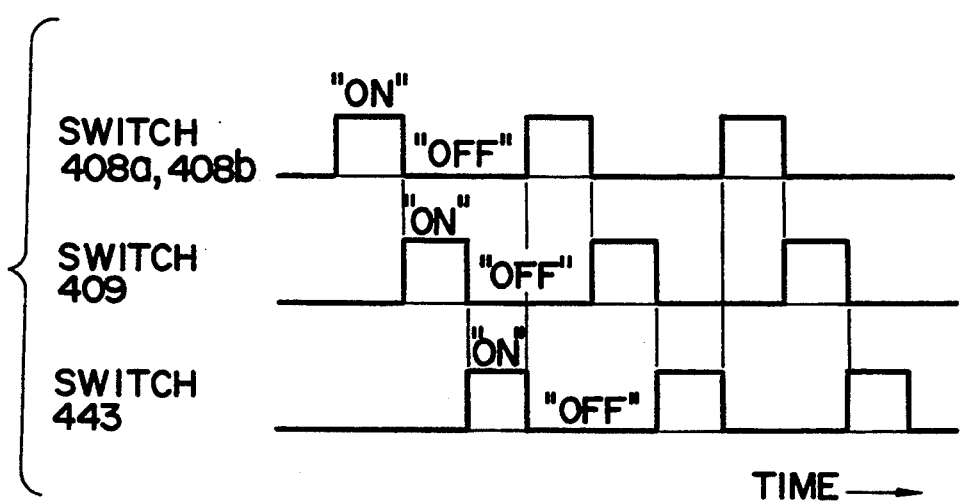
F I G. 126

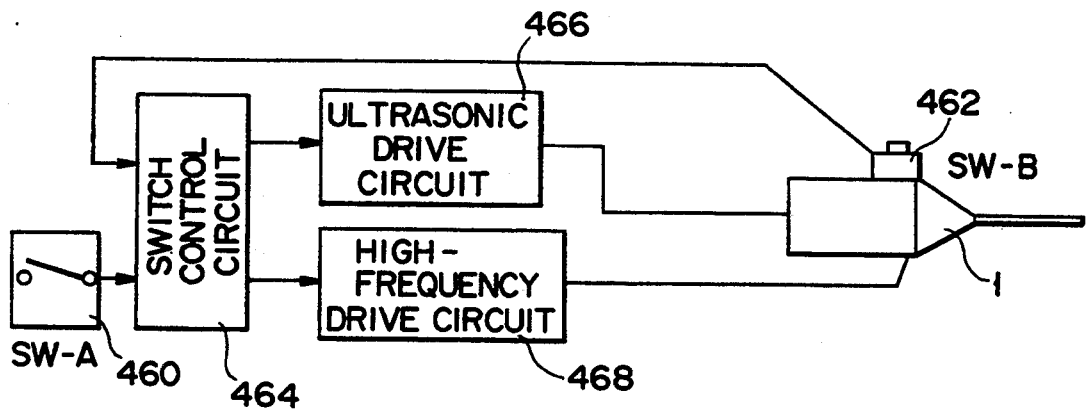
F I G. 127
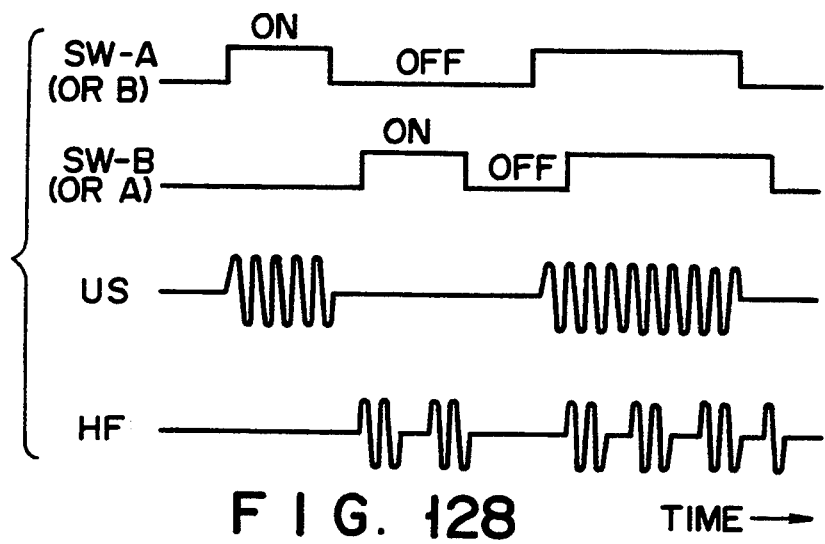
F I G. 128
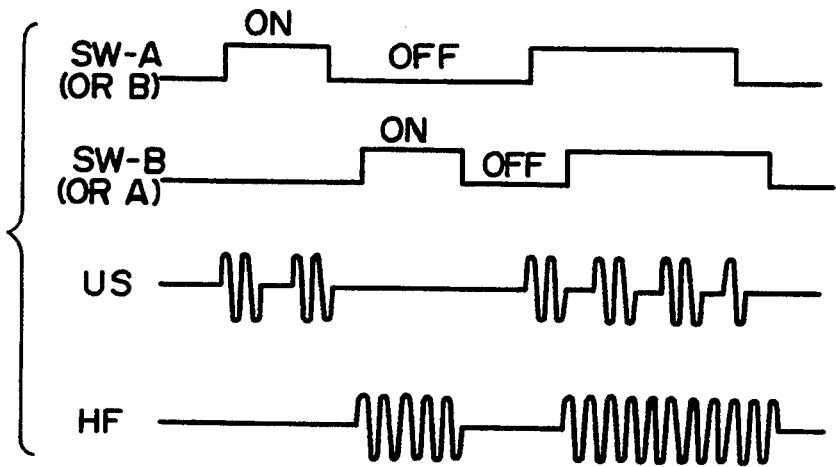
F I G. 129

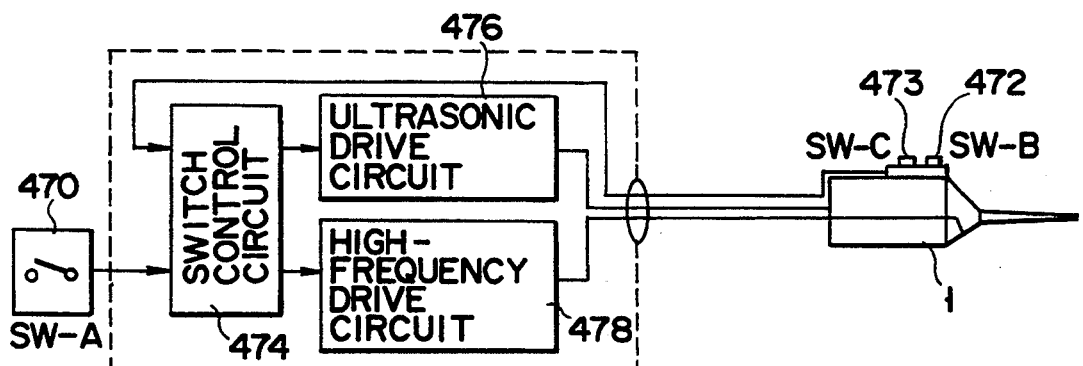
F I G. 130
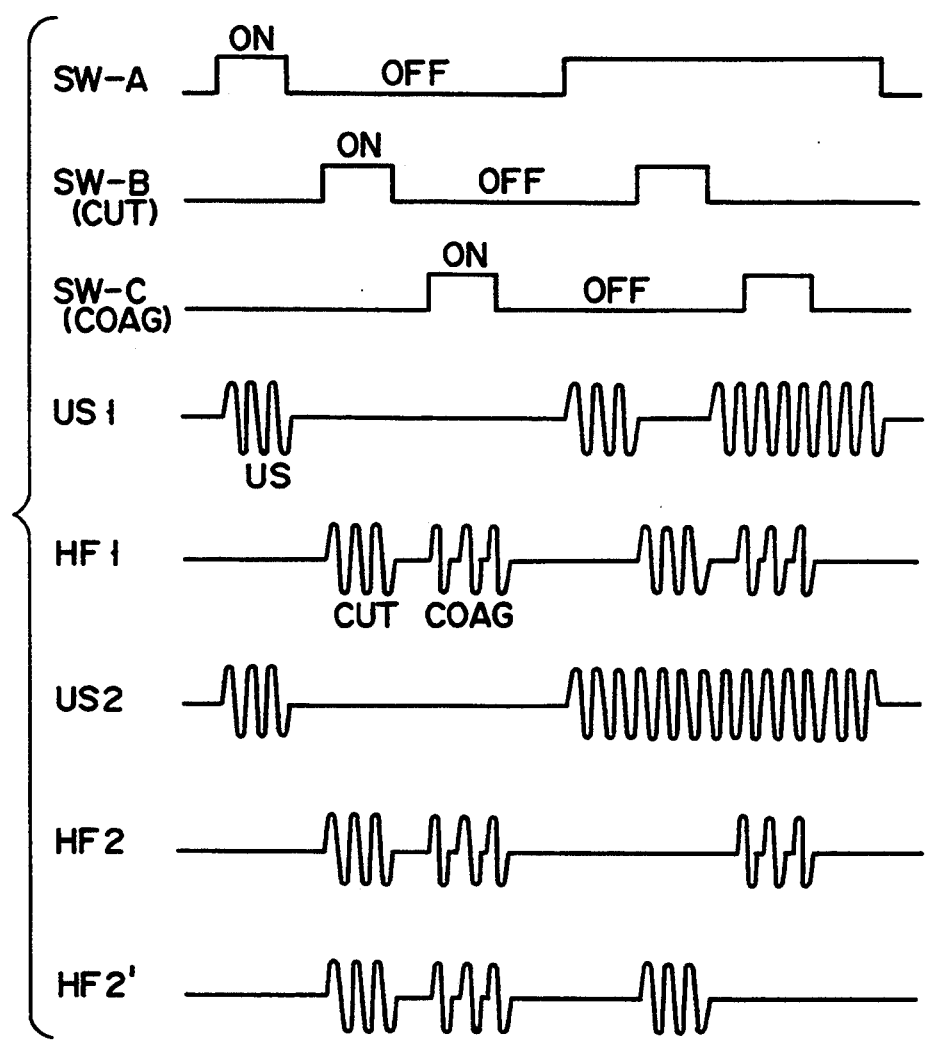
F I G. 131
TIME →

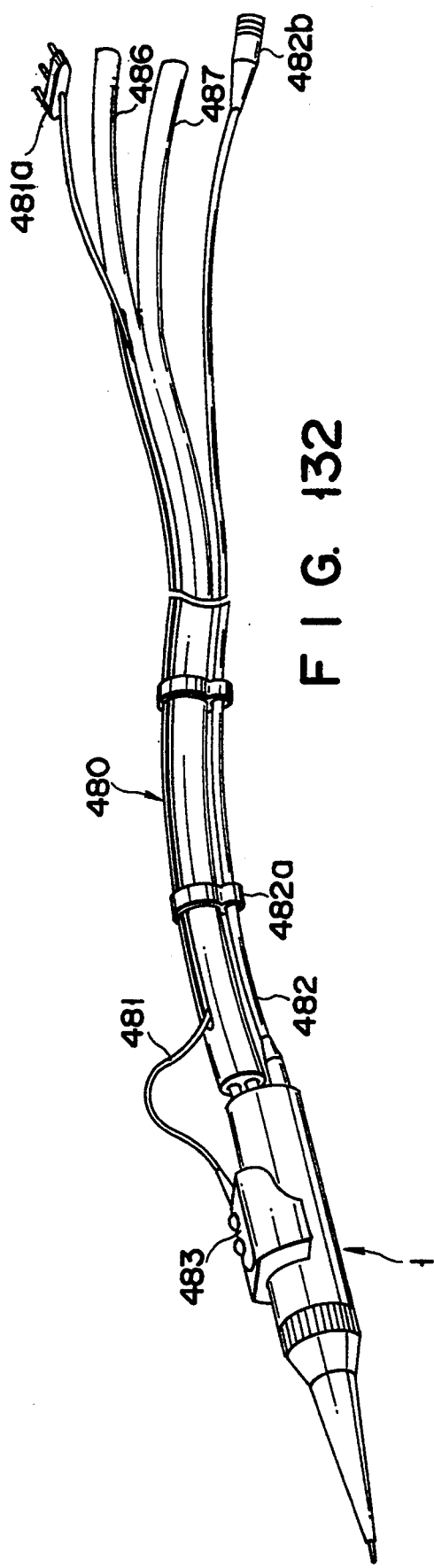
FIG. 132
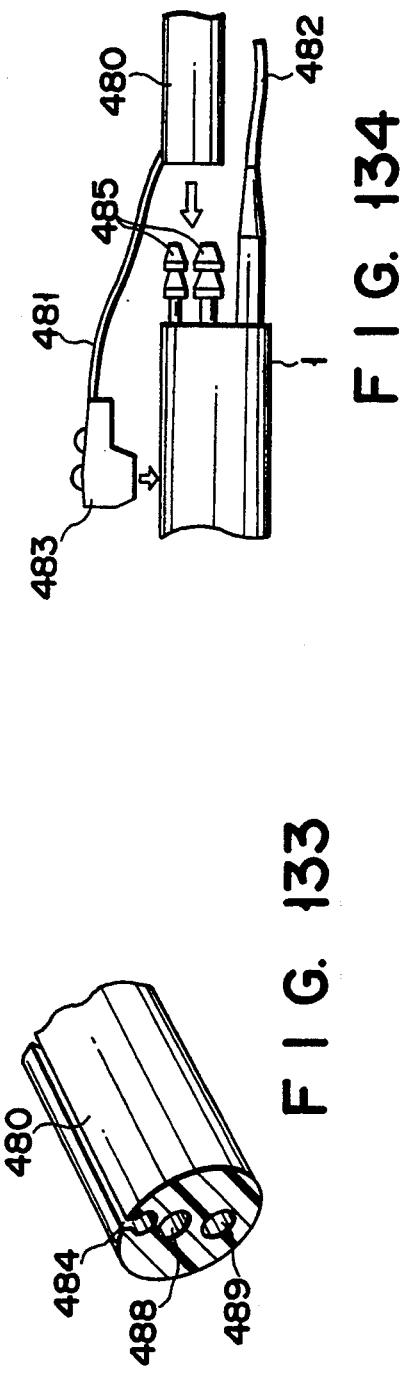
FIG. 134
FIG. 133

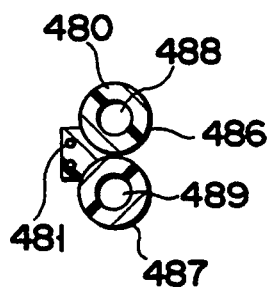
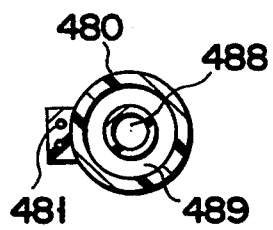
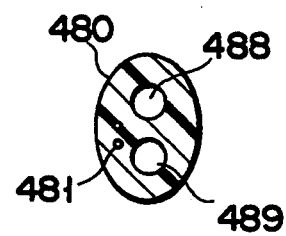
F I G. 135   F I G. 136   F I G. 137
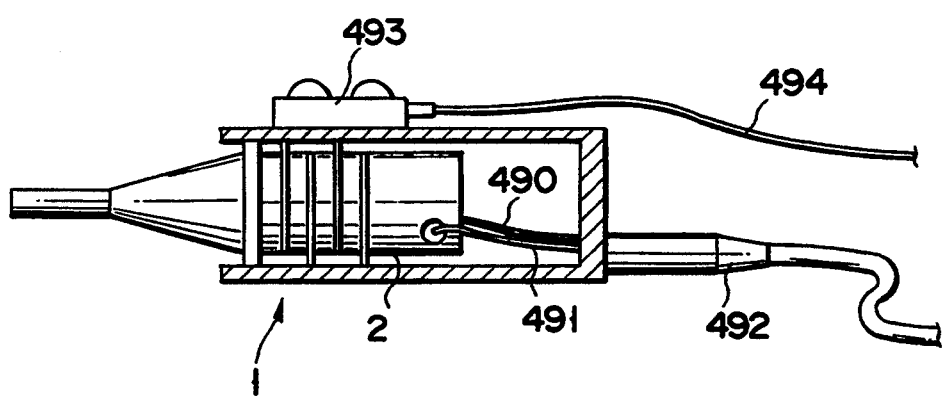
F I G. 138

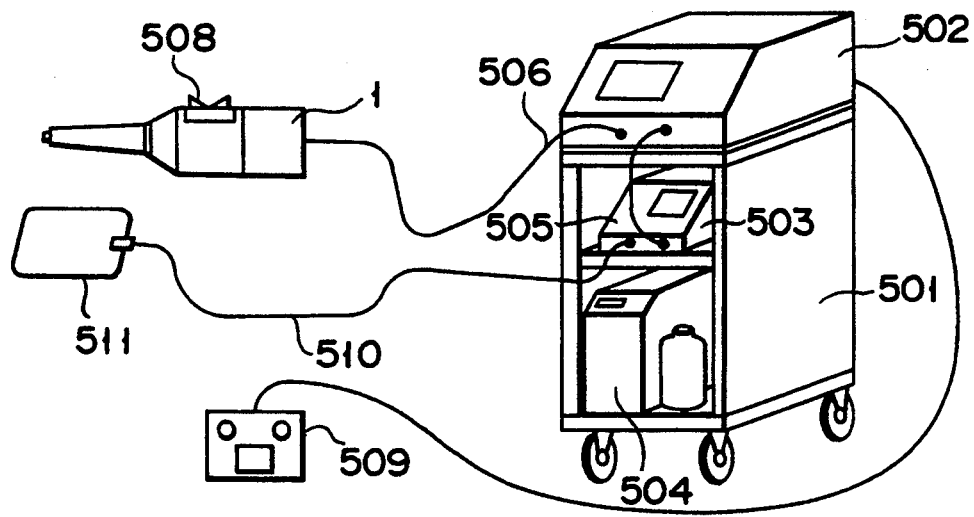
F I G. 141
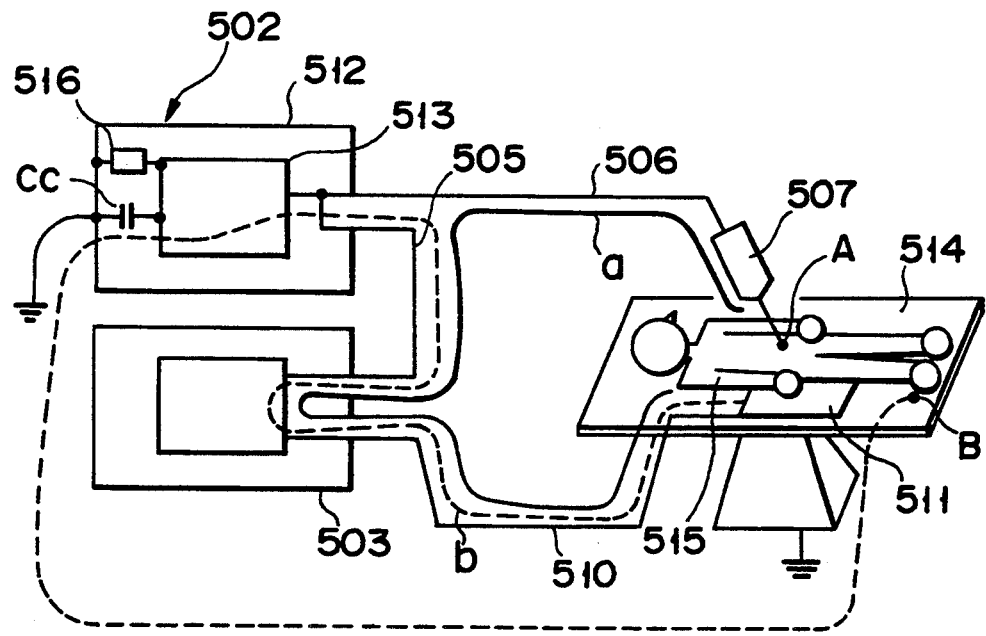
F I G. 142

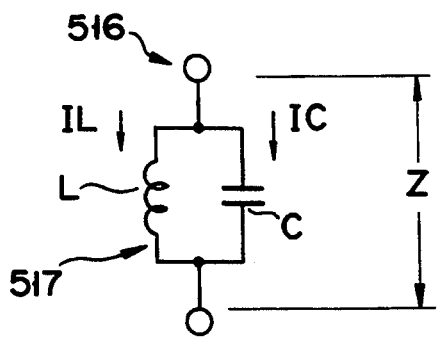
F I G. 143
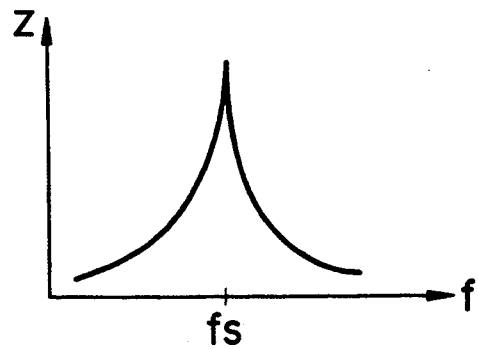
F I G. 144
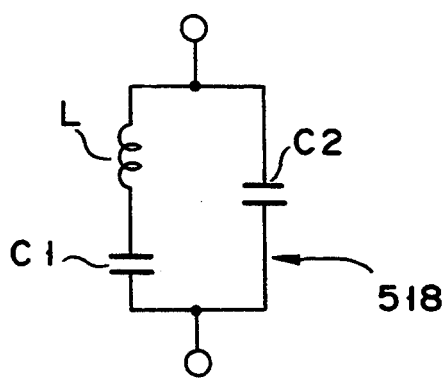
F I G. 145
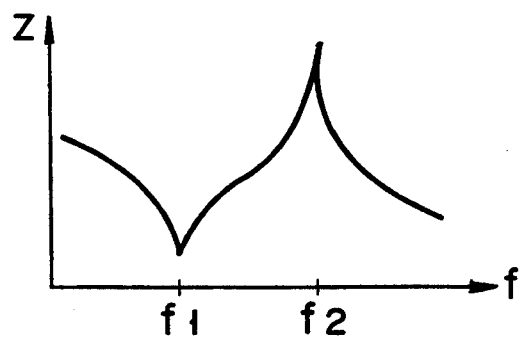
F I G. 146

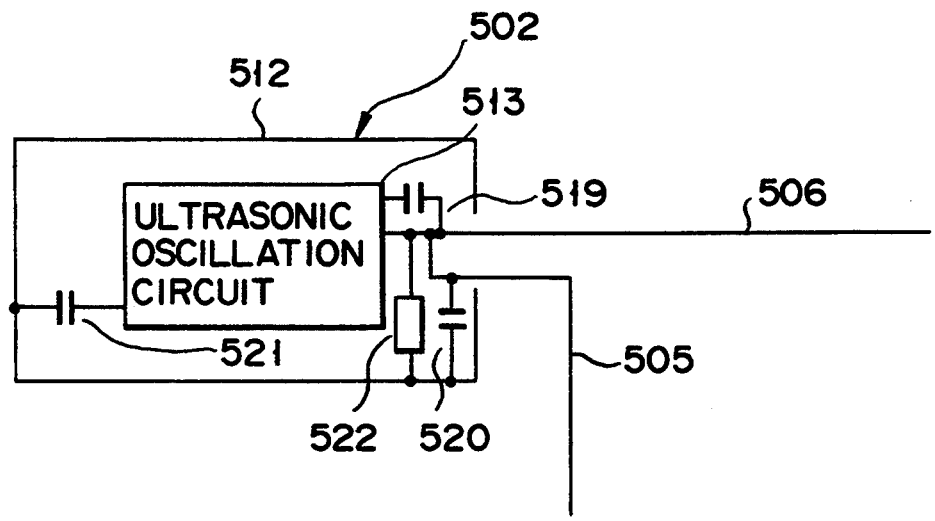
F I G. 147
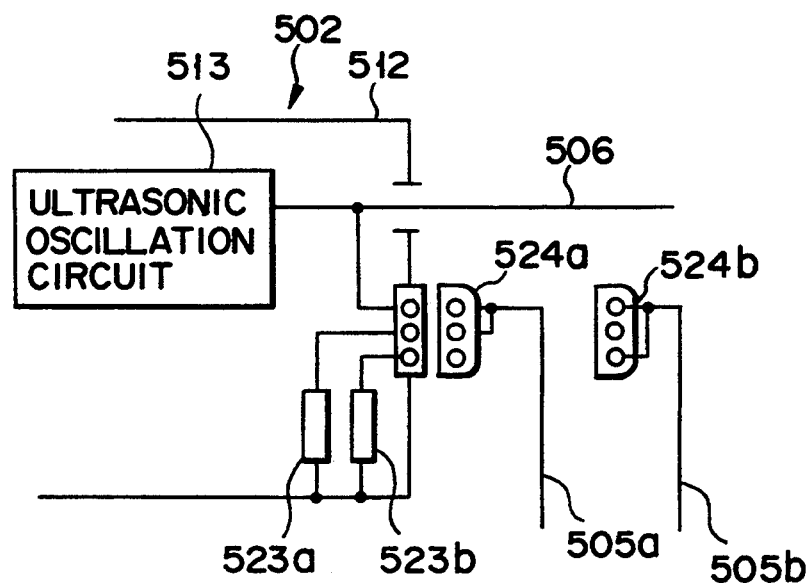
F I G. 148

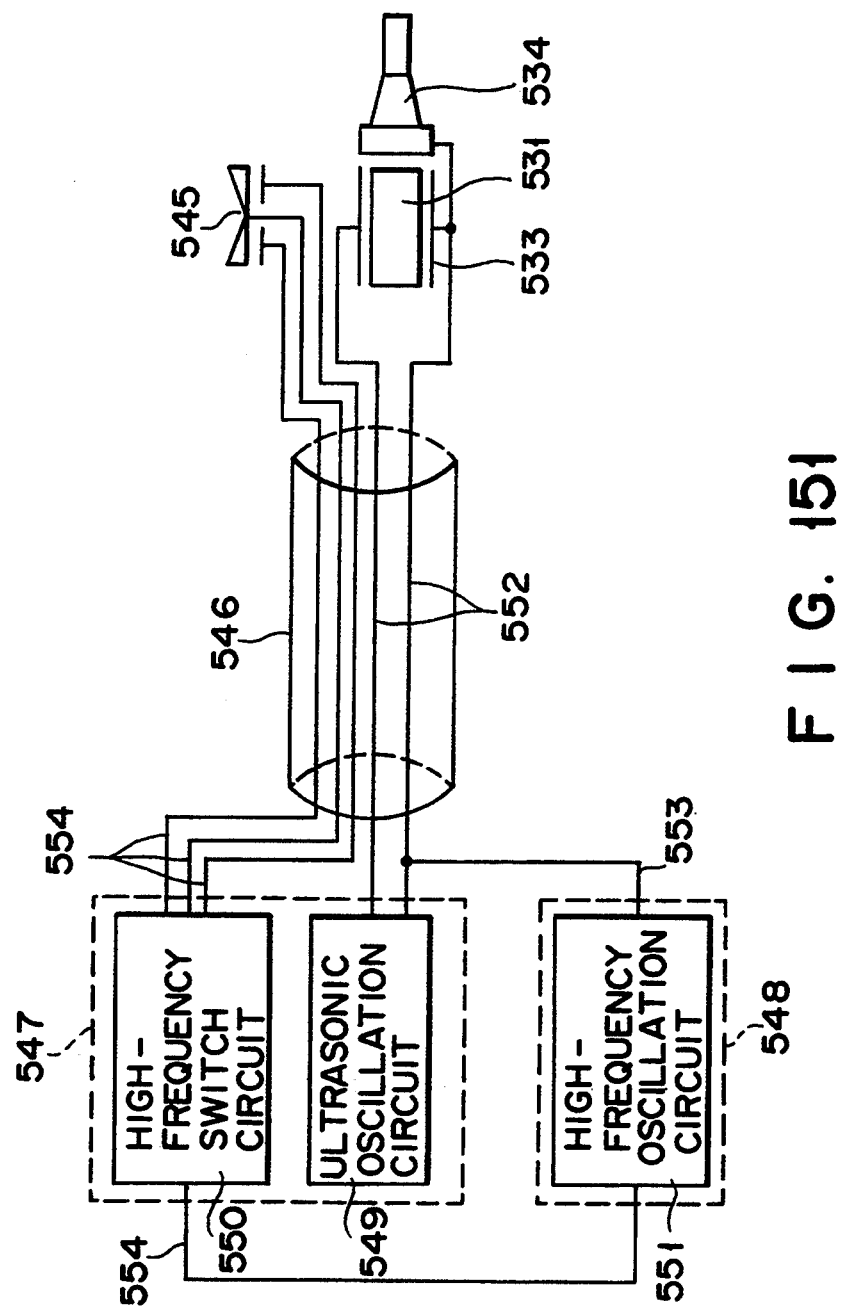
F I G. 151

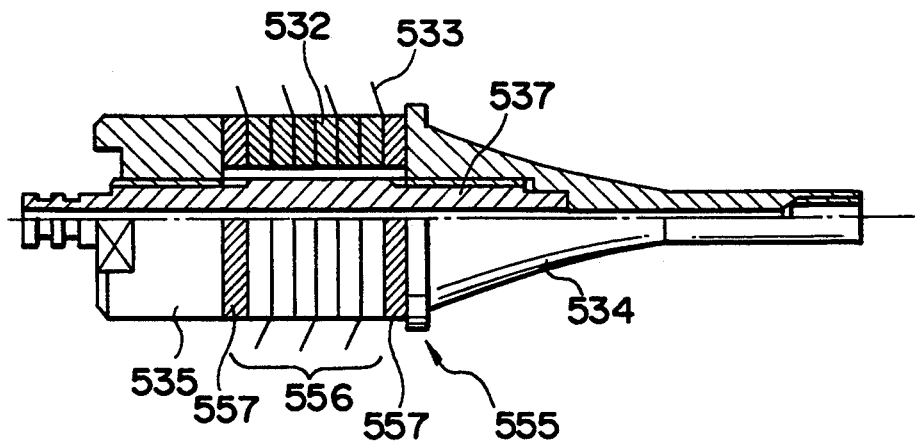
F I G. 152
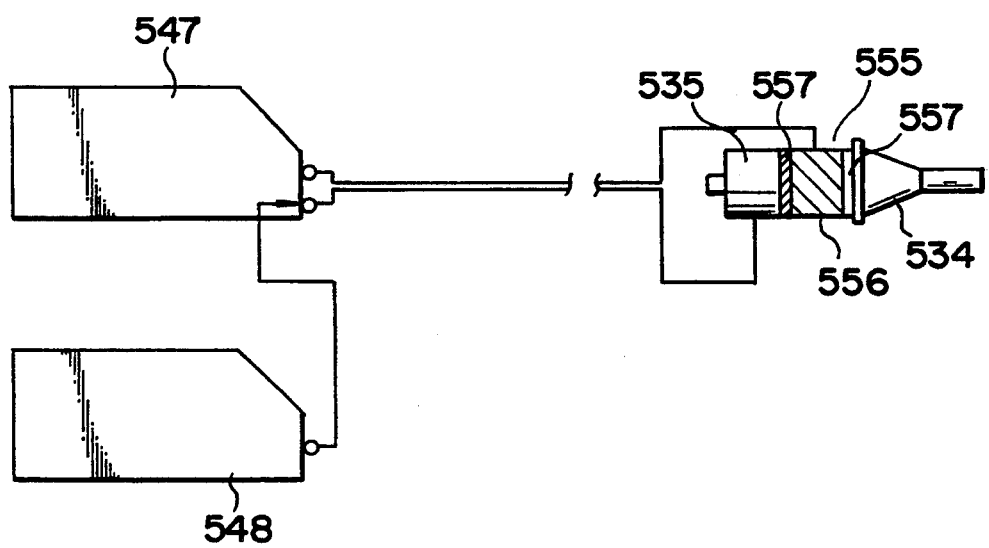
F I G. 153

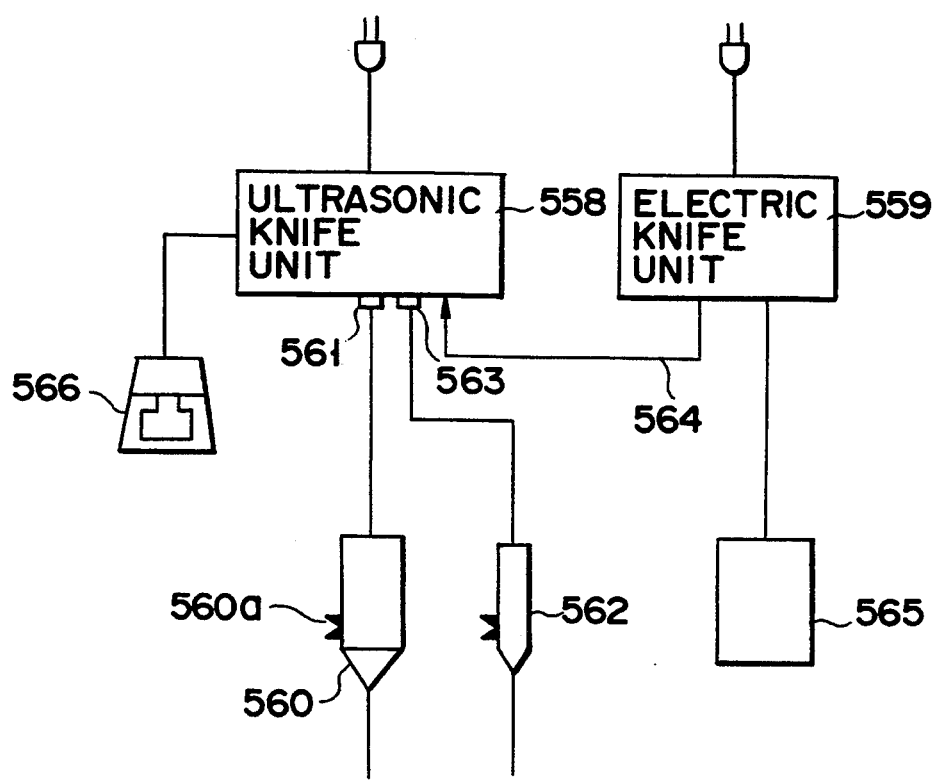
F I G. 154

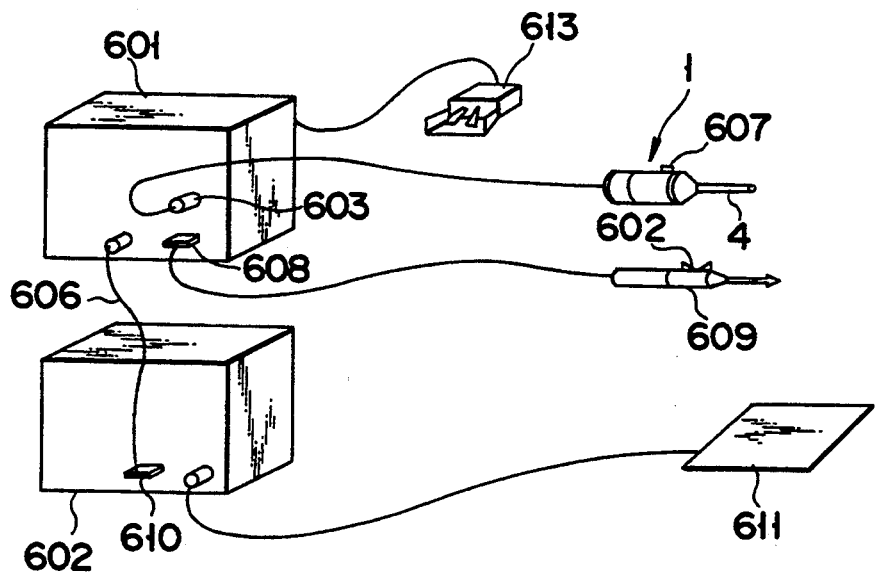
F I G. 155
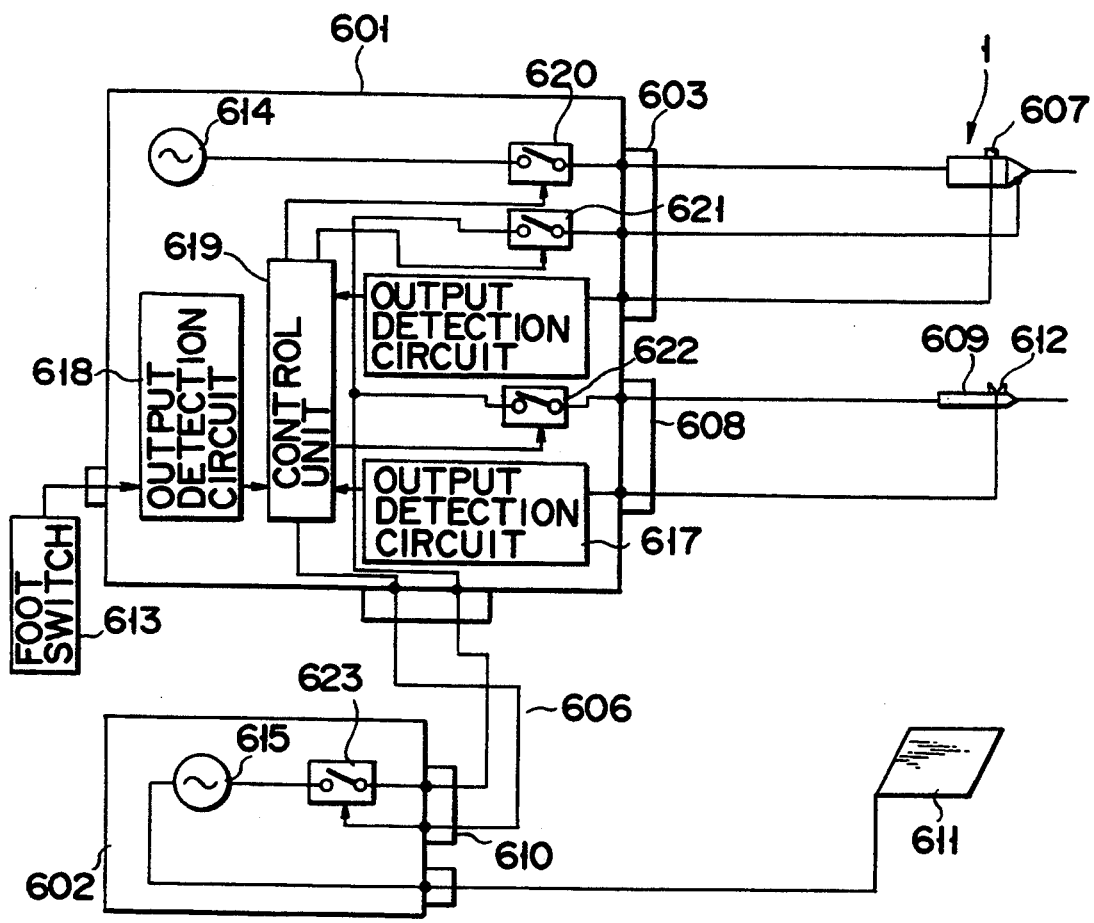
F I G. 156

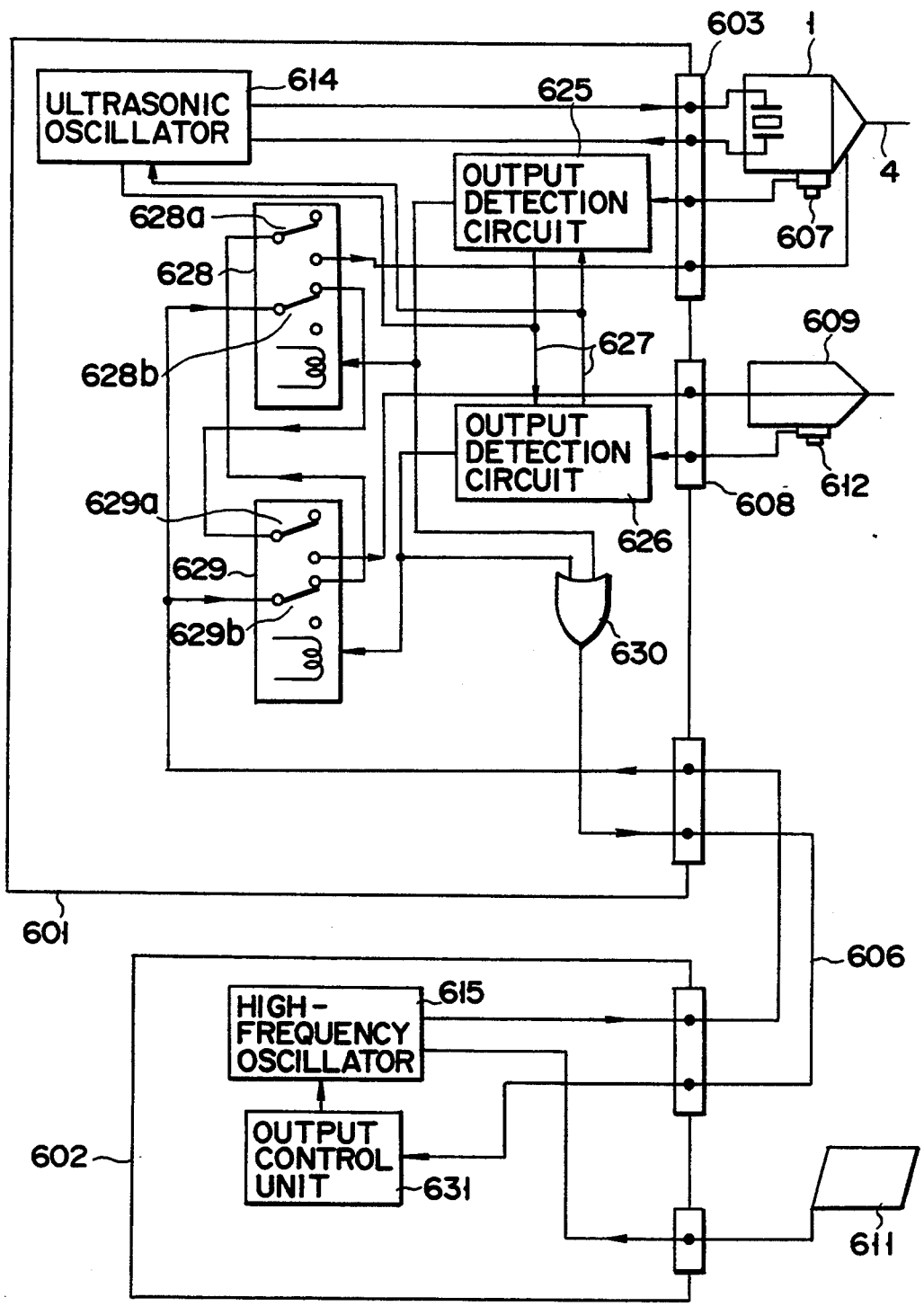
F I G. 157

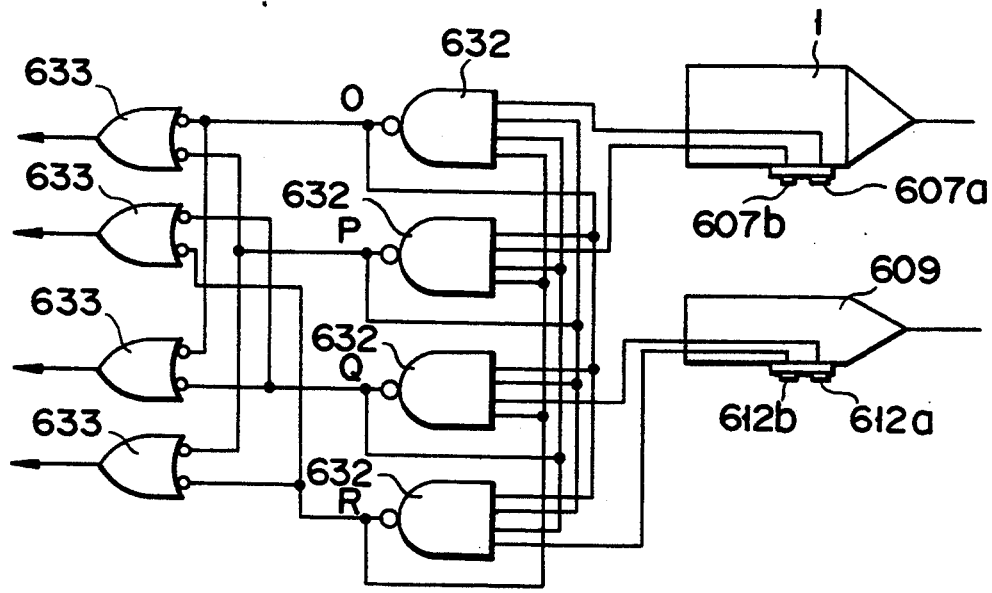
F I G. 158
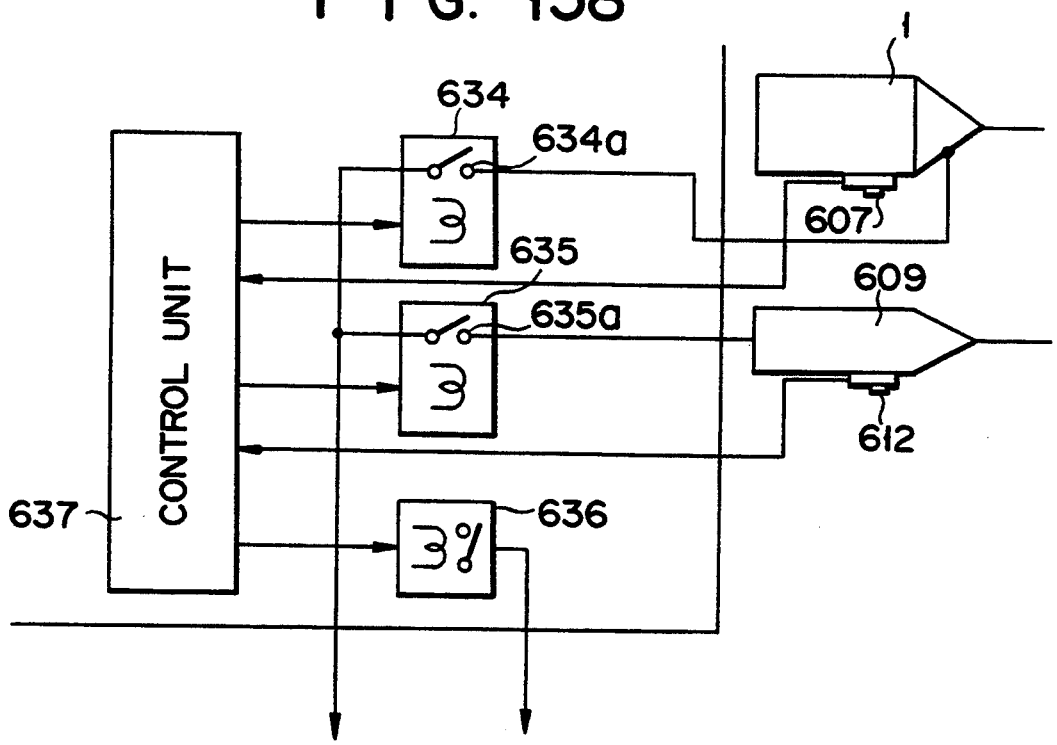
F I G. 159

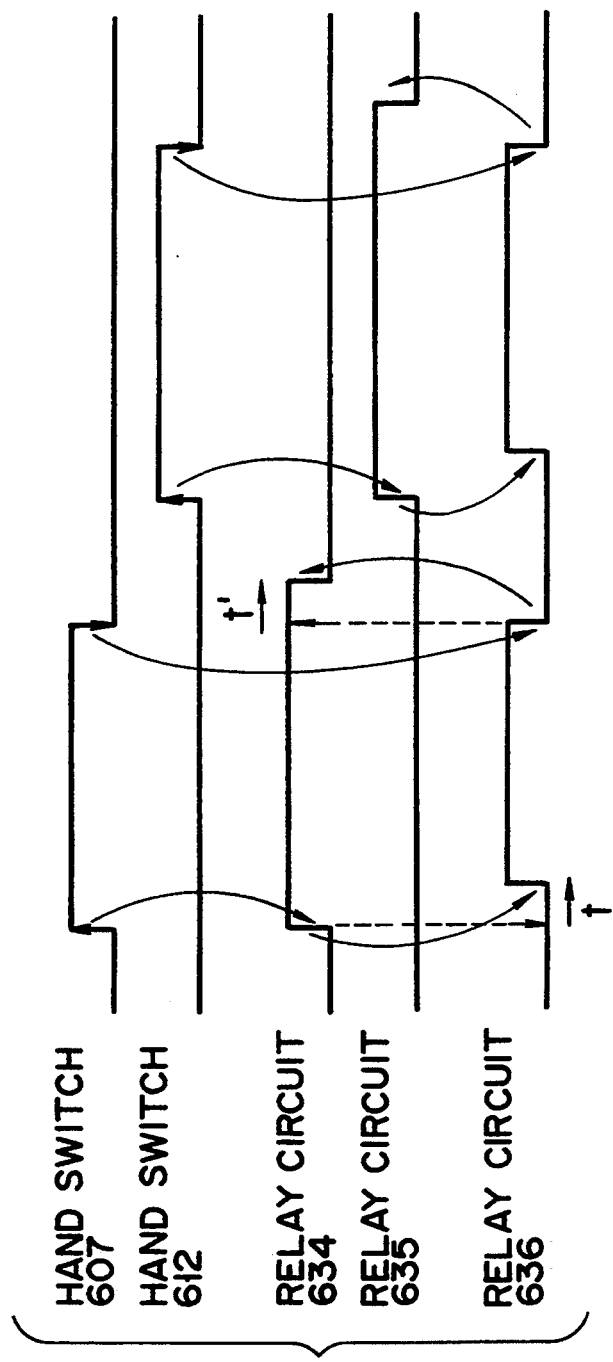

ULTRASONIC TREATMENT APPARATUS

CROSS-REFERENCE TO RELATED APPLICATIONS

This application is a continuation of application Ser. No. 07/680,099, filed Apr. 2, 1991, now abandoned which is a continuation-in-part of application Ser. No. 07/628,650, filed Dec. 14, 1990, now abandoned.

BACKGROUND OF THE INVENTION

1. Field of the Invention

The present invention relates to an ultrasonic treatment apparatus for incising or emulsifying living tissues, or for breaking stones in organs, by applying ultrasonic vibrations to the tissues or the stones.

2. Description of the Related Art

An ultrasonic treatment apparatus, which is designed to incise or emulsify living tissues, or to break stones in organs, by applying ultrasonic vibration to the tissues or the stones, comprises a hand piece containing an ultrasonic oscillator, a probe attached to the hand piece, and a drive device for driving the ultrasonic oscillator.

Only a few types of hand pieces are available for use in combination with the drive device. The conventional ultrasonic treatment apparatus can not serve to incise relatively elastic tissues such as blood vessels and neural tissues, but can serve to incise other tissues. This is why it is used in various surgical operations, among which are operations on the liver which have many blood vessels or on the brain which has many neurons. In addition, the ultrasonic treatment apparatus is also employed in endoscopic surgery since it is not likely to damage the living tissues.

When the ultrasonic treatment apparatus is used, however, it is necessary for a surgeon to adjust the control values of the apparatus, such as the output of the ultrasonic oscillator, the flow rate of a liquid applied to the affected tissue, and the like, in order to accomplish the surgery successfully. Hence, several drive devices must be provided, each designed to set control values appropriate for a specific surgical operation.

Several types of hand pieces, and several types of probes must be provided, so that a surgeon may use them in many combinations to perform various surgical operations. The surgeon attaches one of the hand pieces and one of the probes to the drive device he or she has selected for the operation to be performed. Since each drive device need to be used in combination with hand pieces having different characteristics and also with probes having different characteristics, it is inevitably large and complex.

SUMMARY OF THE INVENTION

The object of the present invention is to provide an ultrasonic treatment apparatus which can be used for various purposes.

In order to achieve the object, there is provided, according to the invention, an ultrasonic treatment apparatus which comprises at least one hand piece, a plurality of probes, and an ultrasonic drive device. The hand piece has an ultrasonic oscillation device for generating ultrasonic vibration. Each probe is adapted to be attached to the hand piece and designed to transmit the ultrasonic vibration generated by the hand piece. The ultrasonic drive device is connected to the hand piece, for driving the ultrasonic oscillation device.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 1 to 8 illustrate an ultrasonic treatment apparatus according to a first embodiment of the present invention; FIG. 1 being a perspective view of the apparatus; FIG. 2 schematically showing the signal-transmitting section incorporated in the apparatus; FIG. 3A to 3C showing three alternative means for identifying the hand piece attached to the drive unit of the apparatus; FIG. 4 being a block diagram showing the internal structure of the apparatus; FIGS. 5A and 5B being graphs representing the characteristics of various probes which can be used in the apparatus; FIG. 6 showing the ID means of the drive unit; FIGS. 7A and 7B being graphs also showing the characteristics of the probes, and FIG. 8 being a flow chart explaining how to alter the control values set for the hand piece connected to the drive unit of the apparatus;

FIGS. 9 to 12 illustrates the drive unit of the ultrasonic treatment apparatus according to the first embodiment of this invention; FIG. 9 showing the operation panel of the apparatus; FIG. 10 being a block diagram of the drive device of the apparatus, and FIGS. 11 and 12 being flow charts explaining how to set control valves suitable for the hand piece connected to the drive device;

FIG. 13 being a longitudinal sectional view showing a hand piece and two alternative probes; FIG. 14 being a diagram showing possible combinations of a hand piece and a probe;

FIGS. 15 to 17 illustrate a second modification of the first embodiment; FIG. 15 being a front view of the second modification; FIG. 16 showing the suction system incorporated in the second modification, and FIG. 17 being a timing chart explaining how to operate the suction system;

FIGS. 18 to 21 illustrate an ultrasonic treatment apparatus according to a second embodiment of the invention; FIG. 18 schematically showing the suction system incorporated in the apparatus, FIG. 19 being a timing chart explaining how to operate the suction system, and FIGS. 20 and 21 being side views of the open/close valve of the suction system;

FIGS. 22 and 23 are side and front views of the open/close valve of the suction system incorporated in a first modification of the second embodiment;

FIGS. 24 and 25 are side and front views of the open/close valve of the suction system incorporated in a second modification of the second embodiment;

FIG. 26 schematically showing the suction system incorporated in this modification, and FIG. 27 being a timing chart explaining the operation of the suction system;

FIGS. 30 and 31 illustrate an endoscope for inserting a probe into a body cavity; FIG. 30 being a sectional view of the endoscope, and FIG. 31 being an enlarged sectional view of a part thereof;

FIG. 32A is a sectional view showing a first modification of the junction between an endoscope and the hand piece of an ultrasonic treatment apparatus according to the invention;

FIG. 32B is also a sectional view illustrating a second modification of the junction;

FIG. 32C is a sectional view showing a third modification of the junction;

FIGS. 33A to 33C illustrate a fifth modification of the junction; FIG. 33A being a sectional view of the endoscope, FIG. 33B being a side view of the junction, and FIG. 33C being a sectional view of the junction, taken along line A—A in FIG. 33B;

FIGS. 34A and 34B are schematic views showing a sixth modification of the junction;

FIGS. 35A and 35B illustrate an another modification of the junction; FIG. 35A being a partial view of the junction and FIG. 35B being a sectional view of the junction, taken along line B—B in FIG. 35A;

FIGS. 36 and 37 are a longitudinal sectional view and cross-sectional view of the distal-end portion of the endoscope;

FIGS. 38 and 39 are a longitudinal sectional view and cross-sectional view of the distal-end portion of another endoscope;

FIGS. 46A and 46B are side view and front view of a seventh treatment tool;

FIGS. 46C and 46D are side view and front view of an eighth treatment tool;

FIGS. 46E and 46F are side view and front view of a ninth treatment tool;

FIGS. 46G and 46H are side view and front view of a tenth treatment tool;

FIGS. 47 and 48 are longitudinal sectional view and rear view of the hand piece incorporated in an ultrasonic treatment apparatus according to a fifth embodiment of the invention;

FIG. 49 is a longitudinal sectional view showing a first modification of the hand piece illustrated in FIGS. 48A and 48B;

FIG. 57 shows a part of the electrode of the ultrasonic oscillator incorporated in the hand piece shown in FIGS. 48A and 48B;

FIG. 58 is a diagram explaining how a lead wire is connected to the electrode;

FIG. 59 illustrates a part of a first modification of the electrode shown in FIG. 57;

FIG. 60 is a diagram explaining how a lead wire is connected the first modification of the electrode;

FIG. 61 shows a part of a second modification of the electrode shown in FIG. 57;

FIG. 62 is a diagram explaining how a lead wire is connected to the second modification of the electrode;

FIG. 63 is a perspective view of a connector for connecting a lead wire to the electrode;

FIGS. 64 to 67 illustrate the hand piece incorporated in an ultrasonic treatment apparatus according to a sixth embodiment of the invention; FIG. 64 being a schematic sectional view of the hand piece, FIG. 65 being a sectional view taken along line II—II in FIG. 64, FIG. 66 being a sectional view taken along line III—III in FIG. 64, and FIG. 67 being the hand switch of the hand piece and the elements associated with the hand switch;

FIGS. 72 and 73 are partially sectional view and perspective view of a second modification of the hand piece shown in FIG. 64;

FIGS. 74 and 75 are partial sectional view and sectional view, taken along line IV—IV in FIG. 73, of a third modification of the hand piece shown in FIG. 64;

FIG. 76 showing a hand piece having a specific electrode assembly, FIG. 77 showing a hand piece containing a water-supplying pipe, FIG. 78 being a shown in FIG. 77, FIG. 79 being a side view showing another modification of the hand piece of FIG. 77, and FIG. 80 being a partial sectional view illustrating another hand piece;

FIGS. 81 to 85 illustrate another modification of the hand piece; FIG. 81 being a side view of the modification, and FIGS. 82 to 85 being sectional views schematically showing various liquid-supplying tubes which can be connected to the hand piece of FIG. 81;

FIG. 86 and FIGS. 87A and 87B illustrate a hand piece for use in an ultrasonic treatment apparatus according to a seventh embodiment of the invention; FIG. 86 being a sectional view of the hand piece, and FIGS. 87A and 87B being exploded perspective views thereof;

FIG. 88 being a sectional view of the hand piece, and FIGS. 89A and 89B being exploded perspective views thereof;

FIG. 94 is a sectional view illustrating a hand piece which can adjust a suction pressure;

FIG. 95 is a sectional view showing a modification of the hand piece illustrated in FIG. 94;

FIG. 96 is a sectional view of a hand piece incorporated in an ultrasonic treatment apparatus according to an eighth embodiment of the present invention;

FIG. 97 is a sectional view of the rear portion of a modification of the hand piece illustrated in FIG. 96;

FIG. 98 being a side view, and FIG. 99 being an exploded perspective view of one of the connection terminals;

FIGS. 100 to 105 illustrate a hand piece having an improved wiring system; FIGS. 100 and 101 being partially sectional side views of the hand piece, FIG. 102 being a sectional view of that part of the hand piece where a switch is located, FIG. 103 being a side view of a rubber contact, FIG. 104 being a partially sectional front view showing the flange portion of the hand piece, and FIG. 105 being a partially section front view showing a modification of the flange portion illustrated in FIG. 104;

FIGS. 107 and 108 illustrate a first modification of the hand piece shown in FIG. 106; FIG. 107 is a side view, and FIG. 108 being a sectional view showing a part of the modification;

FIG. 109 is a sectional view showing the main part of a second modification of the hand piece shown in FIG. 106;

FIGS. 111 and 112 illustrate a hand piece for use in an ultrasonic treatment apparatus according to a tenth embodiment of the invention; FIG. 111 being a side view, and FIG. 112 being a sectional view showing a part of the hand piece;

FIG. 113 is a side view showing a first modification of the vibration-transmitting member incorporated in the hand piece shown in FIG. 111;

FIG. 114 is a side view showing a second modification of the vibration-transmitting member;

FIGS. 115 to 117 illustrate a hand piece for use in an ultrasonic treatment apparatus according to an eleventh embodiment of the invention; FIG. 115 being a side view of the hand piece, FIG. 116 being a partial sectional view thereof, and FIG. 117 being a cross-sectional view thereof, taken along line V—V in FIG. 116;

FIG. 118 is a partially sectional view showing a modification of the vibration-transmitting member incorporated in the hand piece illustrated in FIG. 115;

FIGS. 125 and 126 illustrate an ultrasonic treatment apparatus related to a second modification of the 12th embodiment, the former being a block diagram of the ultrasonic treatment apparatus, and the latter a switch timing chart;

FIGS. 127 through 129 illustrate an ultrasonic treatment apparatus, each related to a third modification of the 12th embodiment, FIG. 127 being a block diagram of the ultrasonic treatment apparatus, FIGS. 128 and 129 each a waveform diagram giving the relation between switching-on/-off, and each of ultrasonic and high-frequency outputs;

FIGS. 130 and 131 illustrate an ultrasonic treatment apparatus related to a 4th modification of the 12th embodiment, FIG. 130 being a block diagram of the ultrasonic treatment apparatus, and FIG. 131 a waveform diagram specifying the relation between switching-on/-off, and each of ultrasonic and high-frequency outputs;

FIGS. 132 through 134 illustrate connection means, each coupling a hand piece of the ultrasonic treatment apparatus to which the present invention relates, and a main body of the apparatus together, FIG. 132 being a perspective view of the hand piece and the connection means, FIG. 133 a sectional view of a liquid supply/suction tube, and FIG. 134 a side view showing a pre-stage of coupling the connection means to the hand piece;

FIGS. 135 through 137 are sectional views showing another modification of said connection means;

FIG. 138 is a partial view of another modification respectively of said connection means and the hand piece;

FIGS. 141 through 144 illustrate a 13th embodiment of the ultrasonic treatment apparatus according to the present invention, FIG. 141 being a perspective view of the ultrasonic treatment apparatus, FIG. 142 a block diagram of the electric circuit incorporated in the ultrasonic treatment apparatus, FIG. 143 a circuit diagram of a drift capacitance cancel means, and FIG. 144 a frequency characteristic diagram;

FIGS. 145 and 146 are a circuit diagram and a frequency characteristic diagram of the drift capacitance cancel means, respectively, involved in a first modification of the 13th embodiment of the present invention;

FIG. 147 is a circuit diagram of the drift capacitance cancel means involved in a second modification of the 13th embodiment;

FIG. 148 is a circuit diagram of the drift capacitance cancel means a third modification of the 13th embodiment;

FIGS. 149 through 151 illustrate another modification of the 13th embodiment, FIG. 149 being a longitudinally sectional view of a hand switch-equipped hand piece, FIGS. 150 and 151 each a block diagram of the electric circuit incorporated in the ultrasonic treatment apparatus;

FIGS. 152 and 153 are partially sectional views showing a modification wherein an oscillator of the ultrasonic treatment apparatus of the 13th embodiment is furnished with an insulation ring on both sides;

FIG. 154 is a block diagram of a surgical operation unit system comprising the ultrasonic treatment apparatus according to the present invention, and a cautery knife;

FIGS. 155 and 156 illustrate a 14th embodiment of the present embodiment, FIG. 155 being a perspective view of the entirety of a surgical operation unit incorporating the ultrasonic treatment apparatus, and FIG. 156 an electric circuit diagram of the surgical operation unit;

FIG. 157 is an electric circuit diagram of the surgical operation unit involved in a first modification of the 14th embodiment;

FIG. 158 is an electric circuit diagram of the surgical operation unit concerned with a second modification of the 14th embodiment; and FIGS. 159 and 160 are an electric circuit diagram and a timing chart respectively of the surgical operation unit involved in a third modification of the 14th embodiment.

DETAILED DESCRIPTION OF THE PREFERRED EMBODIMENTS

An embodiment of the invention will be described with reference to the accompanying drawings.

Figure 1:
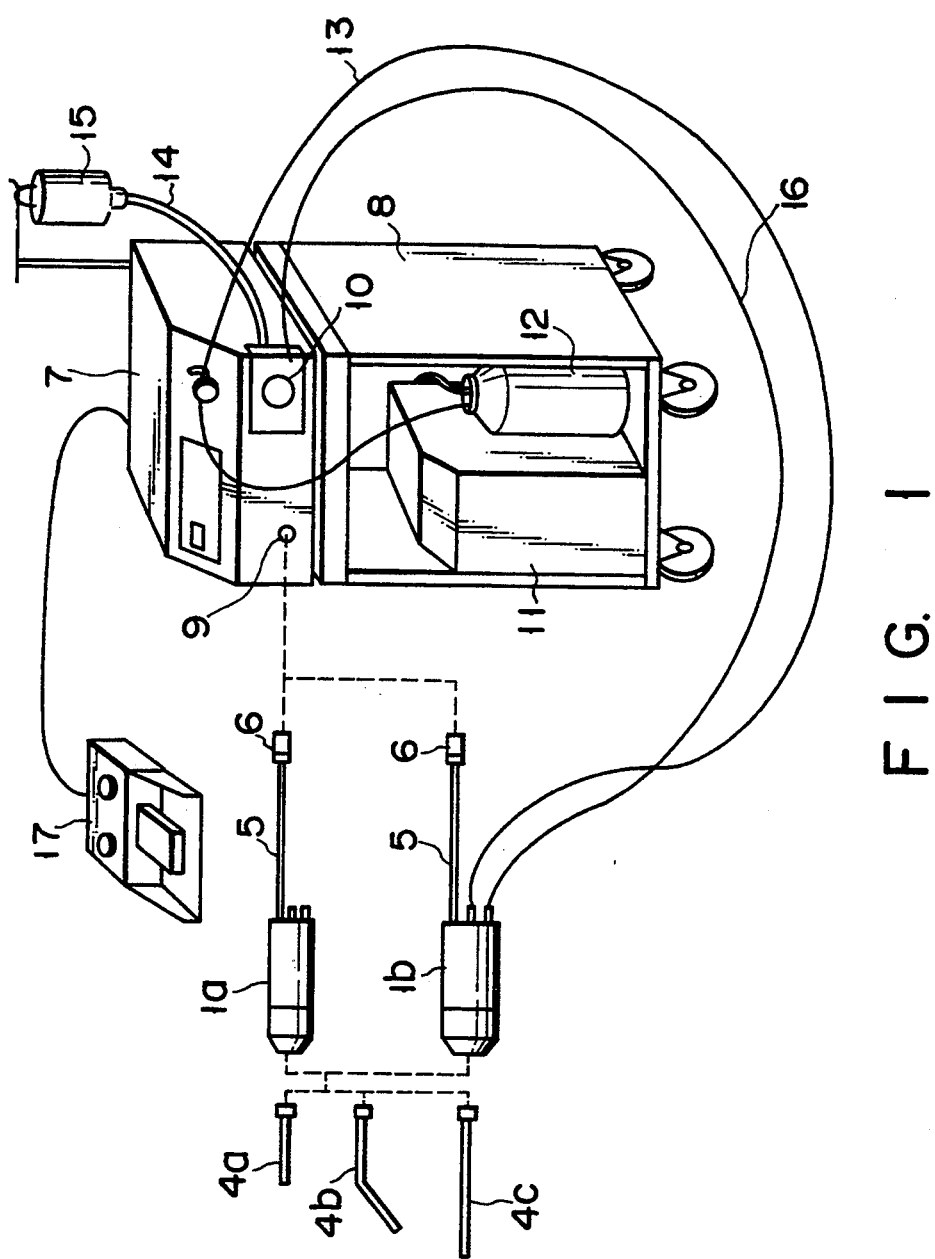

FIGS. 1 to 8 illustrate an ultrasonic treatment apparatus according to a first embodiment of this invention. As is shown in FIG. 1, the apparatus has two types of hand pieces, i.e., a standard hand piece 1a, a reinforced hand piece 1b. Either hand piece contains an ultrasonic oscillator 2 as is illustrated in FIG. 2. The ultrasonic oscillator 2 has a horn 3, to which various probes 4a to 4c can be connected. The probe 4a is generally known as "short probe," the probe 4b as "bent probe," and the probe 4c as "long probe." One of these probes 4a to 4c is selected in accordance with the treatment or surgical operation in which to use the ultrasonic treatment apparatus, and is connected to one end of the hand piece 1a or 1b, or both, by means of screw connection. As FIG. 1 shows, the hand pieces 1a and 1b are connected, at the other end, to two cables 5 which are part of a signal transmission section. Two connectors 6 are connected to the free ends of the cables 5, respectively.

As is shown in FIG. 1, the ultrasonic treatment apparatus further comprises a drive unit 7 placed on a movable table 8. The drive unit 7 has a connector socket 9 and a liquid roller pump 10. The connectors 6 can be plugged into the socket 9, thereby to connect the hand piece 1a or 1b to the drive unit 7. Also mounted on the movable table 8 are a suction pump 11 and a tank 12. The tank 12 is connected to the hand piece 1a or 1b by means of a suction tube 13. The roller pump 10 is connected by a liquid-supply tube 14 to a liquid-supply bottle 15 containing a liquid such as physiological saline solution. The roller pump 10 can be connected by a liquid-supply tube 16 to the hand piece 1a or the hand piece 1b. The drive unit 7 has a foot switch 17.

The short probe 4a is used for general surgical operations, the bent probe 4b for microscopic surgery such as neurosurgery, and the long probe 4c for endoscopic operations. The bent probe 4b and the long probe 4c differ from the short probe 4a in impedance characteristic. More precisely, the probes 4b and 4c are loads greater than the short probe 4a to the ultrasonic oscillators 2 incorporated in the hand pieces 1a and 1b. In other words, either oscillator 2 requires more electrical power to drive the bent probe 4b or the long probe 4c than to drive the short probe 4a. Hence, a high voltage must be applied to the oscillator 2 to drive probes 4b and 4c, whereas a low voltage is applied to the oscillator 2 to drive the probe 4a. Obviously, the bent probe 4b and the long probe 4c generates more heat than the short probe 4a when they are driven by the ultrasonic oscillators 2. It is therefore necessary to supply more water to cool the probe 4b or 4c than to cool the short probe 4a.

As may be understood from the above, the rate of supplying water and some other items must be controlled to perform treatments and surgery successfully by means of the short probe 4a, the bent probe 4b, and the long probe 4c. To this end, the ultrasonic treatment apparatus further comprises various means which will be described, one by one.

As is illustrated in FIG. 2, an identification (ID) means 18 is provided within either connector 6. The ID means 18 is either a resistor 18a as is shown in FIG. 3A, or a zener diode 18b as is shown in FIG. 3B. In the case of the resistor 18a, it suffices to change its resistance in accordance with the kind of the probe connected to the hand piece. In the case of the zener diode 18b, it suffices to change its Zener voltage in accordance with the probe connected to the hand piece. In whichever case, the connector 6 has a signal-transmitting terminal 19 and an ID terminal 20 extending parallel to the terminal 19, as is illustrated in FIGS. 3A and 3B.

The ID means 18 can be designed also to determine which hand piece, 1a or 1b, is connected to the drive unit 7. Further, in the case where the hand pieces 1a and 1b contain different types of ultrasonic oscillators 2, the signal-transmitting terminal 19 can be rearranged in either connector 6 as is shown in FIG. 3C, thereby to match the oscillator 2, in electrical characteristic, with the drive circuit (not shown) incorporated in the drive unit 7.

The drive unit 7 will now be described in detail. As is shown in FIG. 4, the unit 7 comprises a control section 21, a drive circuit 22, a detector circuit 23, a switching relay 24, an output transformer 25, an ID circuit 27, a solenoid valve 29, and display panel 30. The control section 21 is connected to the drive circuit 22, which in turn is connected to the detector circuit 23 designed to detect the voltage v and current I of a drive signal (later described). The circuit 23 is connected by the switching relay 24 to the primary winding of the output transformer 25. The secondary winding of the transformer 25 are connected to the first three contacts 26 of the connector socket 9. The section 21 is also connected by the ID circuit 27 to the fourth and fifth contacts 28 of the socket 9.

The solenoid valve 29 is located partly within the housing of the unit 7 and partly in the intermediate portion of the suction tube 13 which connects the hand piece 1a (1b) to the tank 12. The control section 21 supplies a control signal to the solenoid valve 29, and a display signal to the display panel 30.

when the short probe 4a is connected to the hand piece 1a, and the connector 6 at the tip of the cable 5 of the hand piece 1a then is plugged into the connector socket 9 of the drive unit 7, the signal-transmitting terminal 19 is connected to the first to third contacts 26 of the connector socket 9. Simultaneously, the resistor 18a (i.e., the ID means 18) incorporated in the connector 6 is connected to the fourth and fifth contacts 28 of the socket 9. As a result, the ultrasonic oscillator 2 is connected to the the drive circuit 22, and the resistor 18a is connected to the ID circuit 27.

The control section 21 supplies a command to the drive circuit 22. Upon receipt of the command, the circuit 22 output a drive signal of a small magnitude. The detector circuit 23 detects this signal, which is supplied via relay 24 to the output transformer 25. The drive signal is therefore supplied from the output transformer 25 to the hand piece 1a through the contacts 26, the connector 6 and the cable 5.

Then, it is determined which type of a probe, the short probe 4a, the bent probe 4b, or the long probe 4c, is connected to the hand piece 1a, in accordance with the voltage and current which the detector circuit 23 detects. The type of the probe can be identified since the short probe 4a has an impedance Z2 (=V/I) less than the impedance $Z_1$ of the bent probe 4b and the long probe 4c; that is, $Z_1 > Z_2$ as is best be understood from FIGS. 5A and 5B wherein the impedance and frequency f are plotted on the X axis and the Y axis, respectively.

The detector circuit 23 can be, for example, a resonant frequency detector 31 which is connected between the drive circuit 22 and the switching relay 24. In this case, the probes 4a, 4b, and 4c can be identified, provided that they are so designed that they have different resonance frequencies $f_1$ and $f_2$ as is illustrated in FIGS. 7A and 7B.

The ID circuit 27 determines which hand piece, 1a or 1b, is connected to the drive unit 7, and also which probe, 4a, 4b, or 4c, is connected to the hand piece 1a or 1b. The ID circuit 27 supplies two data items to the control section 21, the first data item representing the type of the hand piece and the second data item representing the type of the probe. The section 21 determines the value of power which the drive circuit 22 is to supply to the ultrasonic oscillator 2 incorporated in the hand piece, based on the first data item supplied from the ID circuit 27. Also, the section 21 controls the switching relay 14 based on the second data item supplied from the ID circuit 27, whereby the relay 24 alters the winding ratio of the output transformer 25. To be more precise, the winding ratio of the transformer 25 is changed in accordance with the impedance of the probe are determined, thereby enabling the hand piece 1a or 1b to drive the probe which is connected to the hand piece 1a or 1b. The control section 21 controls the roller pump such that the liquid can be supplied from the liquid-supply bottle 15 to the hand piece 1a or 1b at an optimal flow rate.

Figure 8:
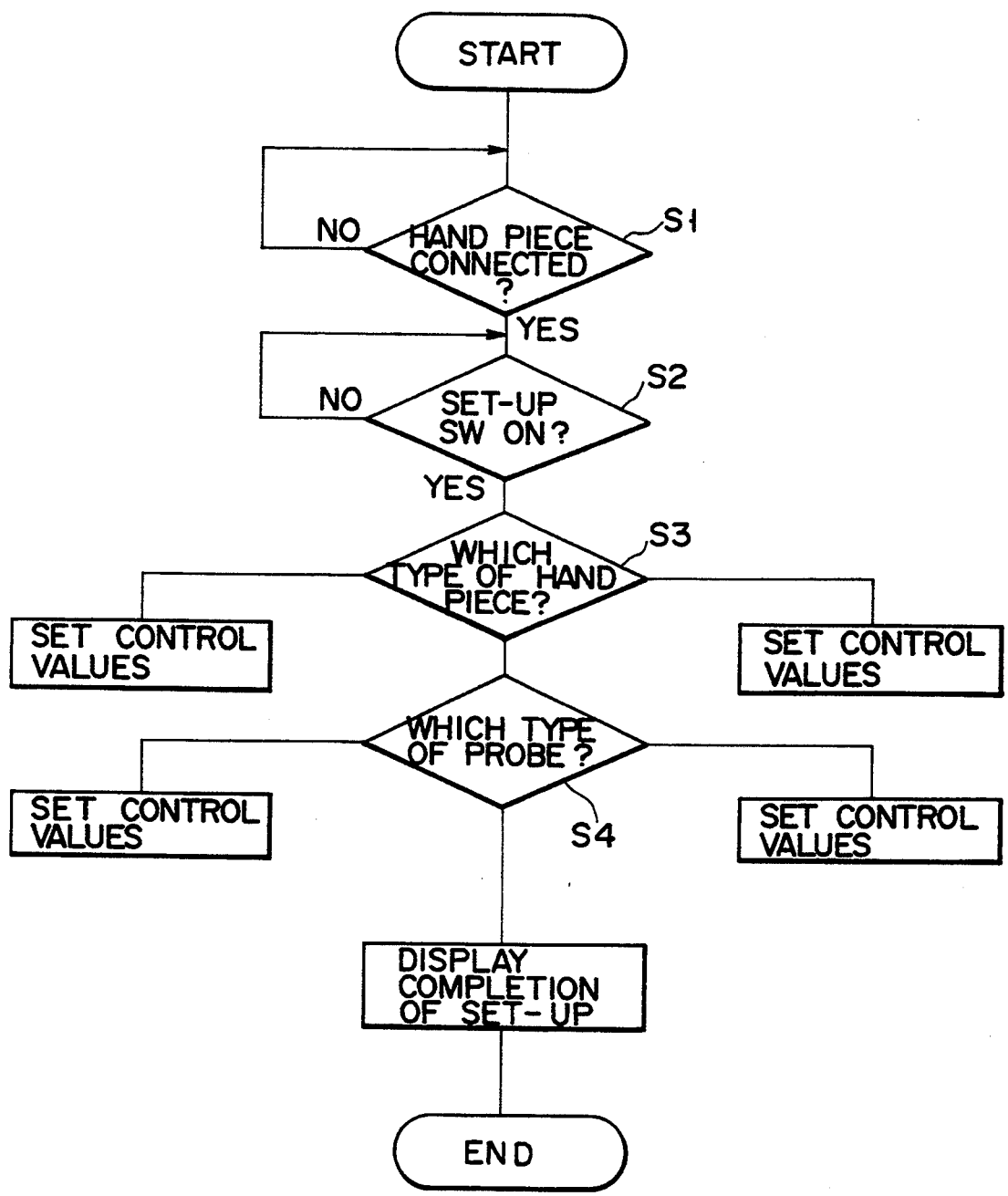

The power to supply to the ultrasonic oscillator 2, the winding ratio of the transformer 25, the flow rate of the liquid supplied to the hand piece 1a or 1b, and the like are altered in the specific routine represented by the flow chart of FIG. 8. First, when the connector 6 is plugged into the connector socket 9, the control section 21 determines in step S1 whether or not the hand piece 1a or 1b has been coupled to the drive unit 7, and the result is displayed by the display panel 30. If YES, the surgeon pushes the set-up switch 30a arranged on the panel 30. In step S2, the control section 21 determines whether or not the set-up switch 30a has been pushed. If YES in step S2, the flow goes to step S3. In step S3, the section 21 determines the type of the hand piece, and sets various values for controlling the hand piece appropriately. Then, the flow goes to step S4, in which the section 21 determines the type of the probe connected to the hand piece, the short probe 4a, the bent probe 4b, or the long probe 4c, and sets various values for driving the probe efficiently.

After all values for controlling the hand piece and the probe are determined, the control section 21 causes the display panel 30 to display the message that all control values have been set. The surgeon then operates the foot switch 17, thereby to control the application of ultrasonic waves to an affected tissue within the patient, the supply of a liquid thereto, or the removal of a fluid therefrom.

The ultrasonic treatment apparatus described above can be employed to perform various surgical operations, by using the hand pieces 1a and 1b and the probes 4a, 4b and 4c in various combinations. When the hand piece 1a is switched to the hand piece 1b, or vice versa, however, it is necessary to change the control values (e.g., the power to supply to the oscillator 2, and the flow rate of the liquid supplied to the hand piece) to those suitable for the new hand piece. To eliminate this disadvantage it is proposed to use means for storing the control values suitable for each hand piece.

Figure 9:
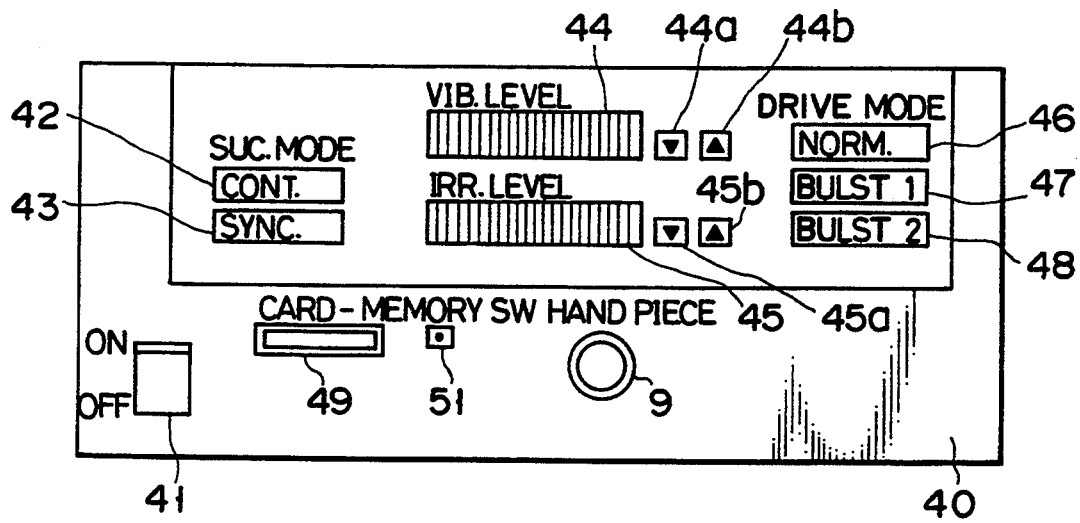

FIGS. 9 to 12 illustrate an ultrasonic treatment apparatus having such means, which is a first modification of the ultrasonic treatment apparatus described above. More specifically, the operation panel 40 of the drive unit 7, which is shown in FIG. 9, includes means for storing the control values appropriate for the hand piece 1a and also the control values suitable for the hand piece 1b. With reference to FIGS. 9 to 12, like or the same components as those of the first embodiment are denoted at the same reference numerals.

As is illustrated in FIG. 9, the operation panel 40 has a power switch 41, a continuance-mode switch 42, a synchronous-mode switch 43, two level meters 44 and 45, and three drive-mode switches, i.e., a normal switch 46, a first burst switch 47 and a second burst switch 48. The power switch 41 is operated to turn on or off the drive unit 7. The continuance-mode switch 42 is pushed to removing a fluid from a cavity continuously. The synchronous-mode switch 43 is pushed to perform fluid-removal in synchronism with the application of ultrasonic waves to an affected portion or operation of a foot switch (not shown). The level meter 44 is designed to set the amplitude of ultrasonic oscillation; it includes a down-switch 44a and an up-switch 44b. The level meter 45 is used to set a flow rate for the liquid supplied to the affected portion; it has a down-switch 45a and an up-switch 45b. When the normal switch 46 is depressed, ultrasonic waves are continuously applied to an affected portion within a patient. When the first pulse switch 47 is operated, ultrasonic waves are intermittently applied to the affected portion at a first frequency. When the second pulse switch 48 is pushed, ultrasonic waves are intermittently applied to the affected portion at a second frequency.

The operation panel 40 further has a card slot 49 and a memory switch 51. The card slot 49 allows the path of an IC memory card 50 into the drive unit 7. When the memory switch 51 is pushed, the control values set by the control section 21 are recorded in the IC memory card 50 inserted in the drive unit 7.

Figure 10:
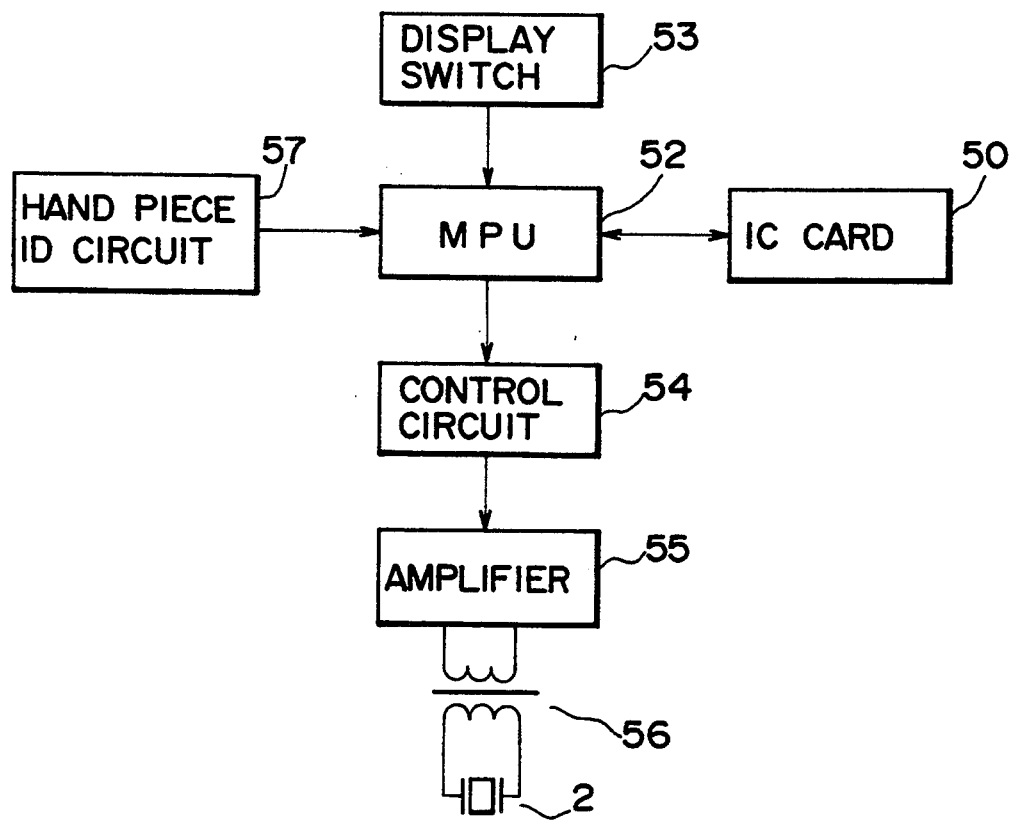

FIG. 10 is a block diagram showing the internal structure of the drive unit 7 of the second embodiment. As is shown in FIG. 10, the unit 7 comprises a microprocessor unit 52, a control circuit 54, an amplifier 55, a transformer 56, and a hand piece ID circuit 57. The microprocessor unit 52 is connected to the display switch 53 of the operation panel 40 and also to the control circuit 54. The control circuit 54 is designed to control the output of an ultrasonic oscillator 2. The circuit 54 supplies a drive signal to the amplifier 55. The amplifier 55 amplifies the drive signal. The amplified drive signal is supplied to the transformer 56. The output of the secondary winding of the transformer 56 is supplied to the ultrasonic oscillator 2, driving the oscillator 2. The IC memory card 50 is electrically connected to the microprocessor unit 52, and data can be exchanged between the card 50 and the unit 52. The hand piece ID circuit 57 is connected to the microprocessor unit 52, for supplying the unit 52 with data indicating whether a hand piece is connected to the drive unit 7, and which hand piece it is, the hand piece 1a or the hand piece 1b.

With reference to the flow chart of FIG. 11, it will now be explained how the drive unit 7 shown in FIG. 10 operates.

When the power switch 41 is turned on, it is determined, in step S1, whether a hand piece is connected to the unit 7. If NO in step S1, the control values set before the power switch 41 has been turned off are set again. If YES in step S1, the flow goes to step S2, in which it is determined whether or not the IC memory card 50 is connected to it. If YES in step S2, the microprocessor unit 52 reads from the card 50 the control values set for the hand piece by operating the operation panel 40, and sets these control values automatically. If NO in step S2, the control values set for the hand piece are read from the microprocessor unit 52 and set again automatically.

With reference to the flow chart of FIG. 12, it will be explained how the drive unit 7 operates if the power switch 41 is already on. When a hand piece is connected to the unit 7, it is determined, in step S1, whether or not an IC memory card 50 has been electrically connected to it. If YES in step S1, the microprocessor unit 52 reads from the IC memory card 50 the control values set for the hand piece by operating the operation panel 40, and set these control values again. If NO in step S1, the control values set for the hand piece are read from the microprocessor unit 52 and are set automatically.

When a surgeon connects an IC memory card to the microprocessor unit 52 and then pushes the memory switch 51, the control values set for the hand piece connected to the unit 7 by operating the operation panel 40 are automatically stored into the IC memory card 50. Once the control values have been thus stored in the IC memory card, and the card is connected to the microprocessor unit 52, any surgeon authorized to operate the ultrasonic treatment apparatus need not be bothered to operate the panel 40 to set the control values suitable for the same hand piece. Even if no IC memory card is connected to the unit 52, the control values set by operating the panel 40 are automatically stored into the microprocessor unit 52 when the memory switch 51 is pushed. Simultaneously, the control values for the hand piece which was connected to the unit 7 when the power switch 41 was turned off are also stored into the microprocessor unit 52. Further, when the hand piece is disconnected from the unit 7, and a new hand piece is connected to the unit 7, the control values suitable for the new hand piece are set automatically and are stored into the unit 52. The data representing the type of the new hand piece is also stored into the microprocessor unit 52.

Hence, whenever the hand piece is replaced by a new one, the control values appropriate for the new hand piece can be automatically set, and the surgeon need not operate the panel 40 to set these control values. This automatic setting of control values helps to increase the operation efficiency of the ultrasonic treatment apparatus. Further, in the case where two or more surgeons authorized to operate the apparatus have an IC memory card 50 each, each of them can use the apparatus with high efficiency, merely by inserting the card 50 into the drive unit 7, thereby setting the control values for the hand piece he or she is going to manipulate.

An outer memory device (not shown) may be used with the drive unit. In this case, a connector of the outer memory device may be provided instead of the card slot for the IC memory card.

The tips of probes of different types, which can be attached to the hand piece, must be vibrated at different amplitudes to emulsify different types of tissues within body cavities, each type with the highest possible efficiency. Therefore, the connecting member and vibration-transmitting member of each type of the conventional probe are made to have different vibration-magnifications, which are in turn different from those of the connecting member and vibration-transmitting member of a conventional probe of any other type. To prepare a connecting member and a vibration-transmitting member, which have different vibration-magnifications, and then to combine them into a probe results in an increase in the cost of the probe.

According to the present invention, to avoid such a cost increase, identical connecting members having the same vibration-magnification are connected with vibration-transmitting members having various vibration-magnifications and tips of various shapes, thereby fabricating probes whose tips vibrate at different amplitudes and have different shapes.

Figure 13:
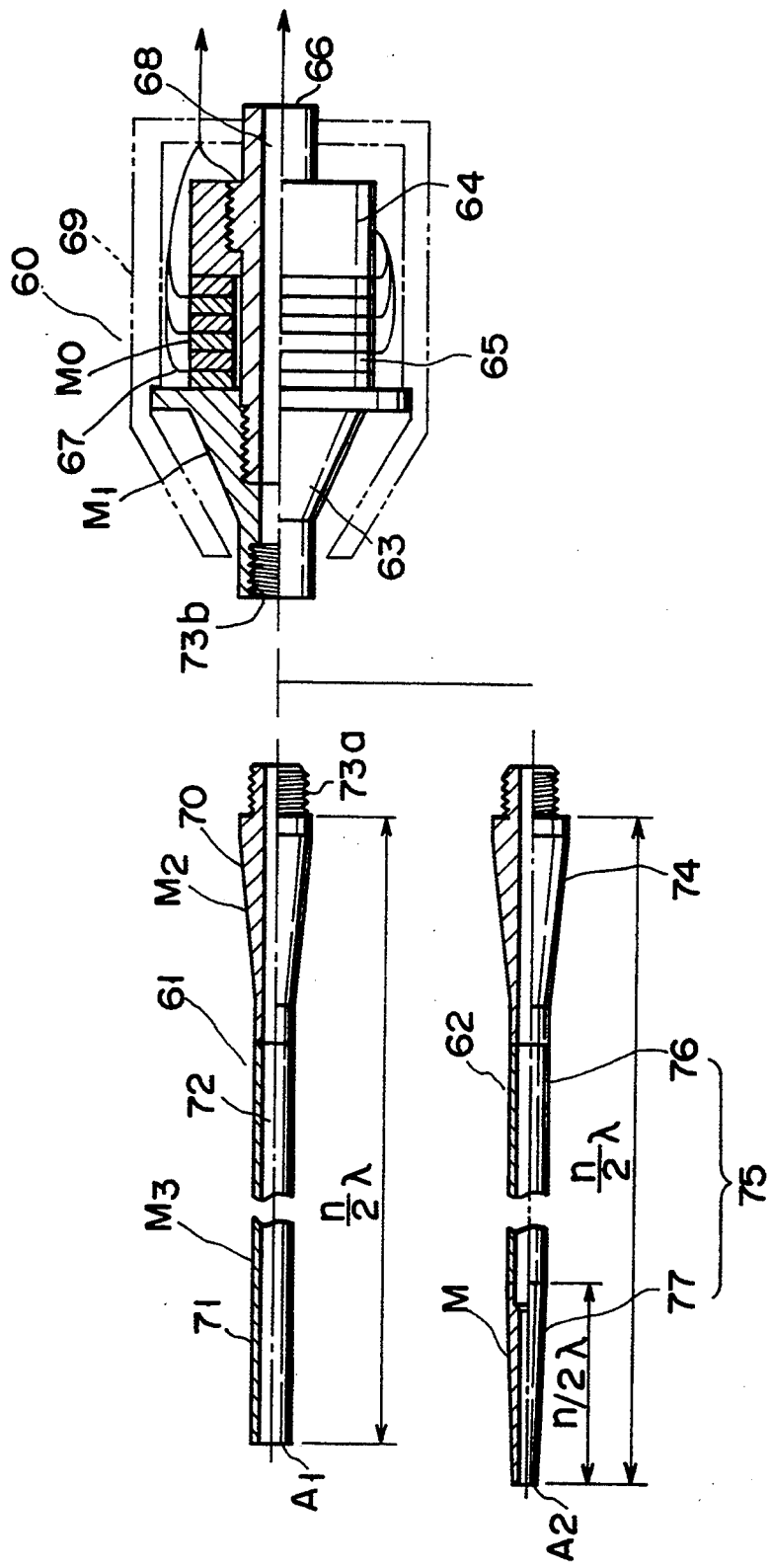
FIGS. 13 and 14 show a modification of the first embodiment.

More specifically, as is shown in FIG. 13, two probes 61 and 62 can alternatively be connected to an ultrasonic oscillator 60 contained in a hand piece 1. The oscillator 60 comprises a horn 63, a metal block 64, and a plurality of piezoelectric elements 65 clamped together between the horn 63 and the block 64, by means of a hollow bolt 66. The oscillator 60 further comprises electrodes 67 interposed among the piezoelectric elements 65 and is connected to a drive power source (not shown). The interior of the horn 63 and that of the bolt 66 define a suction path 68, which is connected to a suction pump (not shown). The ultrasonic oscillator 60 is located within the housing 69 of the hand piece 1. The ultrasonic oscillator is a resonant system. When driven, the piezoelectric elements 65 vibrate at an amplitude $A_0$, and the end of the horn 63 is vibrated at an amplitude of $A_0 \times M_1$, where $M_1$ is a vibration-magnification.

The first probe 61 comprises a connecting portion 70 and a vibration-transmitting portion 71 having vibration-magnifications $M_2$ and $M_3$, respectively. Both portions 70 and 71 have an axial through hole. The through hole of the connecting portion 70 is connected to the suction path 68 of the ultrasonic oscillator 60 when the first probe 61 is set into screw engagement with the horn 63. As is shown in FIG. 13, the proximal end of the connecting portion 70 has a male screw 73a, while the distal end of the horn 63 has a female screw 73b. Hence, the first probe 61 can be connected to, and disconnected from, the ultrasonic oscillator 60 through the horn.

If the first probe 61 is connected to the oscillator 60, the vibration of the horn 63 is transmitted to the connecting portion 70 and then to the vibration-transmitting portion 71. The vibration of the horn 63, at the amplitude $A_0 \times M_1$, is amplified $M_2$ times at the connecting portion 70, and further amplified $M_3$ times at the vibration-transmitting portion 71. As a result of this, the tip of the first probe 61 vibrates at amplitude $A_1$ which is equal to $A_0 \times M_1 \times M_2 \times M_3$.

If the tip of the probe 61 is in contact with a living tissue within a body cavity, it emulsifies the tissue. The emulsified tissues are removed from the cavity because of the negative pressure which the suction pump (not shown) generates in the suction path 68 and which acts in the through hole of the first probe 61. The vibration-transmitting portion 71 is a straight, thin-walled pipe made of a titanium alloy, and its vibration-magnification $M_3$ is 1.

Any portion of the vibration-transmitting portion 71 where a node of vibration is located is more likely to be broken than any other portion. Hence, it is important to select such a value for the vibration-magnification $M_2$ of the connecting portion 70 that said portion will not be damaged. Also important is to select such a value for the wall thickness of the portion 71 and such a titanium alloy for the material thereof, that the portion 71 will not be damaged and the tip of the probe 61 (i.e., the distal end of the portion 71) will vibrate at a desired amplitude to emulsify and remove a tissue efficiently.

As is illustrated in FIG. 13, the second probe 62 comprises a connecting portion 74 which is identical to the portion 70 of the first probe 61, and a vibration-transmitting portion 75 connected to the connecting portion 74. The portion 75 is a two-piece component, formed of a pipe 76 and a tip 77 connected to the distal end of the pipe 76. The pipe 76 and the tip 77 can be connected by welding, screwing or adhesion. The tip 77 has vibration-magnification $M_4$. It follows that the tip of the second probe 61 vibrates at amplitude $A_2$ which is equal to $A_0 \times M_1 \times M_2 \times M_3 \times M_4$. Obviously, the tip of the second probe 62 vibrates at a greater amplitude than that of the first probe 61. The second probe 62 is, therefore, suitable for use in vibrating a living tissue more vigorously.

The tip 77 has a length of $n\lambda/2$, where n is an integer, and $\lambda$ is the wavelength of the ultrasonic vibration. The probes 61 and 62 have different lengths which are generally defined as $n\lambda/2$.

Since the first probe 60 and the second probe 62 comprise a common component, i.e., the connecting member, they can be manufactured at a cost lower than in the case where their connecting portions 70 and 74 have different vibration-magnifications as in the probes hitherto used.

The tip 77 is welded to the distal end of the pipe 76 by means of TIG, laser-welding, electron-beam welding, or diffusion-welding. The second probe 62 can be subjected to age hardening in a vacuum, so as to have a greater strength.

Preferably, the vibration-transmitting member of either probe is subjected to fluid-polishing, sand-blasting, buffing, electric-field polishing, or electric-field composite polishing, thereby removing the oxide coating from the inner and outer peripheries of the vibration-transmitting member of either probe, and eliminating cracks or scars. If so surface-treated, the vibration-transmitting member will have a greater strength.

It is desirable that the connecting member and vibration-transmitting member of either probe be made of material having a small Young's module, such as a titanium alloy or an aluminum alloy (e.g., duralumin).

Figure 14:
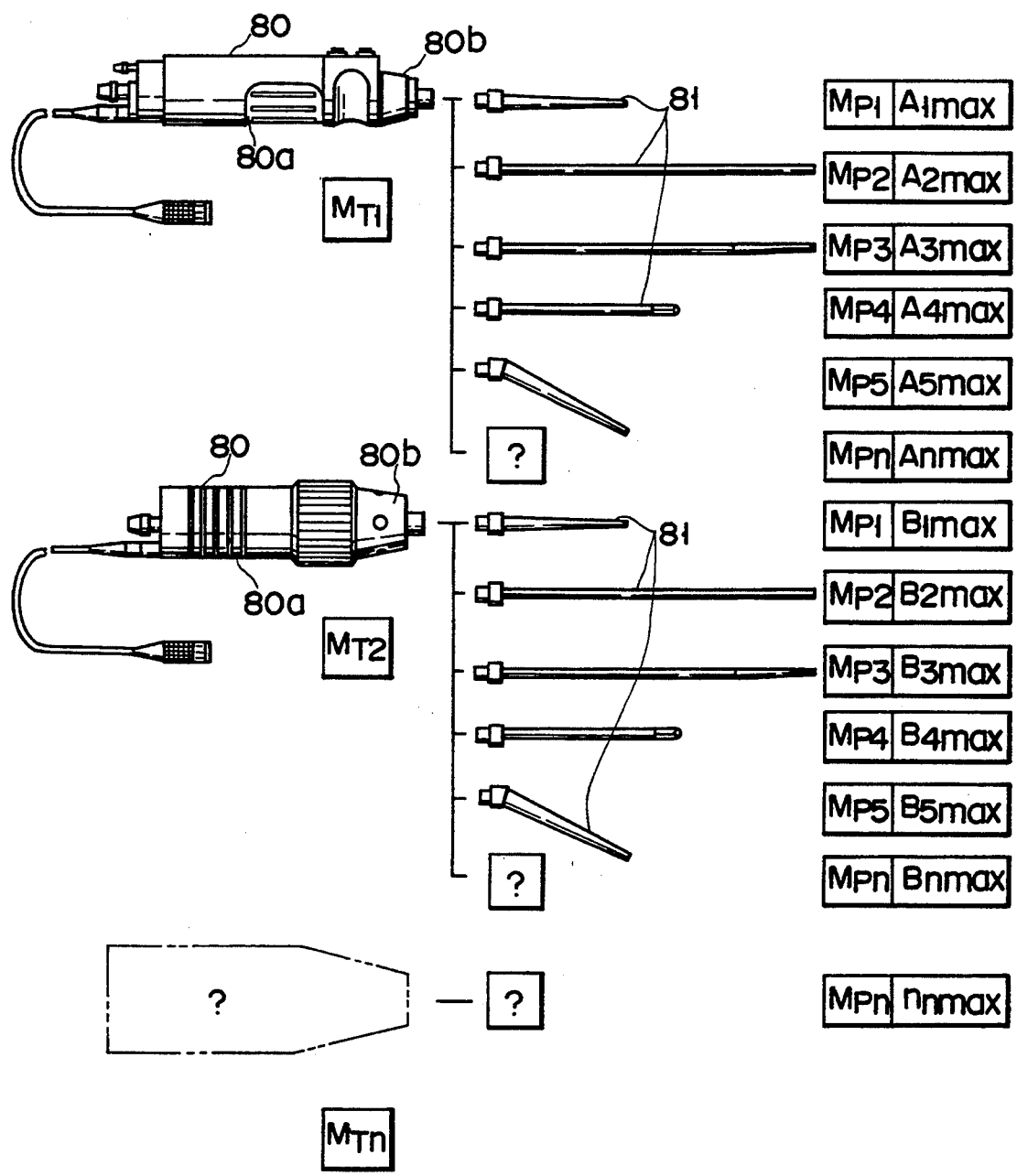

According to the invention, various types of hand pieces 80 can be alternatively used in combination of various types of probes 81, as can be understood from FIG. 14. More specifically, the hand pieces 80 are used in combination with the probes 81, in accordance with the type of the ultrasonic oscillator 80a and the type of the horn 80b, both being two major components of the hand piece 80, thereby to satisfy the equation (1) or, more generally, the equation (2):

$$\frac{A_{1max}}{MT_1 \cdot MP_1} = \frac{A_{2max}}{MT_2 \cdot MP_2} = \frac{A_{3max}}{MT_3 \cdot MP_3} = \quad (1)$$

$$\frac{A_{4max}}{MT_4 \cdot MP_4} = \frac{A_{5max}}{MT_5 \cdot MP_5} = \frac{A_{nmax}}{MT_n \cdot MP_n} = \frac{B_{1max}}{MT_1 \cdot MP_1} =$$

$$\frac{B_{2max}}{MT_2 \cdot MP_2} = \frac{B_{3max}}{MT_3 \cdot MP_3} = \frac{B_{4max}}{MT_4 \cdot MP_4} = \frac{B_{5max}}{MT_5 \cdot MP_5} =$$

$$\frac{B_{nmax}}{MT_n \cdot MP_n} = \text{constant}$$

$$\frac{M_{nmax}}{MT_n \cdot MP_n} = \text{constant} \quad (2)$$

where $M_{Tn}$ is the vibration-magnification of the horn 80b, $M_{Pn}$ is the vibration-magnification of the probe 81, and $M_{nmax}$ is the maximum amplitude at which the tip of the probe 81 should be vibrated to achieve the purpose for which the hand piece 80 and the probe 81 are employed.

In other words, a hand piece and a probe are used in combination, such that the horn 80b and the probe 81 cooperate to magnify the vibration of the ultrasonic oscillator 80a, which oscillates at a constant amplitude to vibrate the tip of the probe 81 at the maximum amplitude $M_{nmax}$. In the drive device it suffices to control the oscillator 80a to vibrate at a constant amplitude. The vibration-amplitude of the ultrasonic oscillator 80a can be set in accordance with the type of the hand piece 80.

The conventional ultrasonic treatment apparatus has suction means for removing an affected tissue incised from the inner walls of a body cavity through a probe connected to the hand piece. The suction means comprises a suction pump, a vessel for containing tissue removed from the cavity, and a control section for controlling the suction pump. The suction pump is driven even while the ultrasonic oscillator contained in the hand piece is not being driven. Hence, a negative pressure is always applied in the probe, and there is inevitably the possibility that the negative pressure may damage a normal tissue within the cavity as the probe is moved out of the cavity.

A second modification of the ultrasonic treatment apparatus, which is designed to eliminate this possibility, will be described with reference to FIGS. 15 to 17. The same components as those of the apparatus shown in FIG. 1 will be denoted at the same numerals in FIGS. 15 to 17, and will not be described in detail.

Figure 16:
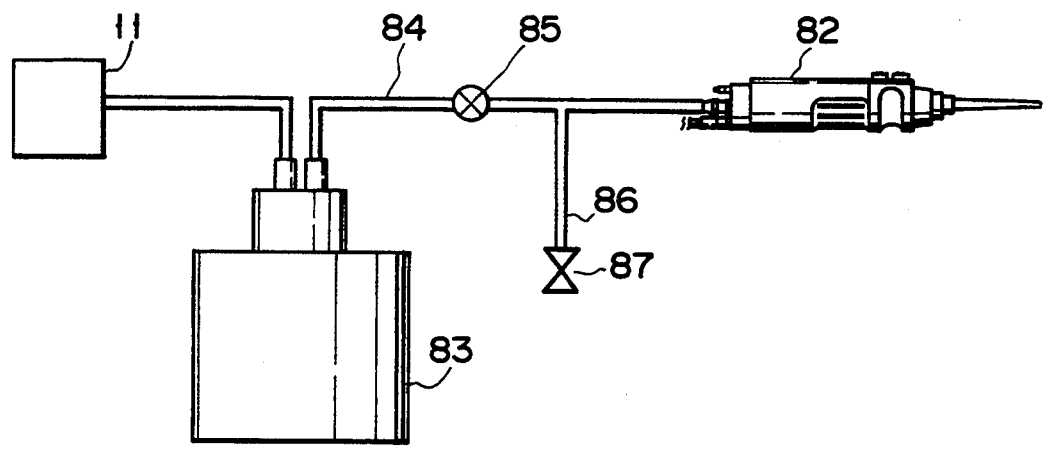

As is shown in FIGS. 15 and 16, a suction tube 84 connects a hand piece 82 and an suction tank 83. An open/close valve 85 is provided on the suction tube 84. As is shown in FIG. 16, a branch tube 86 is connected, at one end, to that portion of the suction tube 84 which is located between the hand piece 82 and the valve 85. The other end of the branch tube 86 is connected to a solenoid valve 87.

Figure 17:
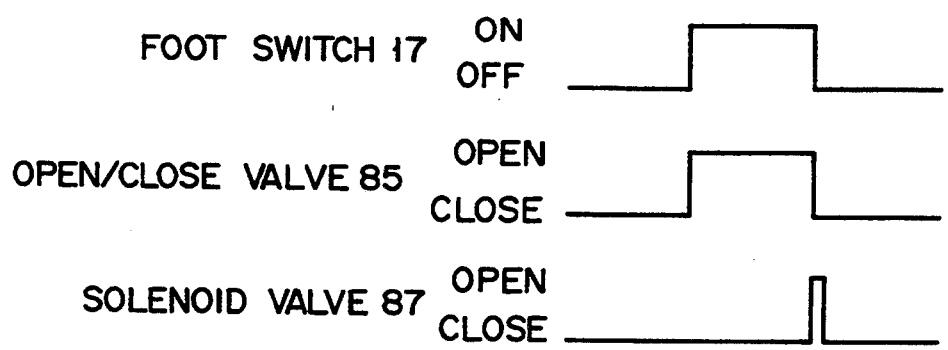

As long as a foot switch 17 is on, thus driving the ultrasonic oscillator provided within the hand piece 82, the open/close valve 85 remains open, whereas the solenoid valve 87 remains closed, as can be understood from the timing chart of FIG. 17. When the foot switch 17 is turned off, the open/close valve 85 is closed, while the solenoid valve 87 is opened and remains open for a predetermined period thereafter, as is illustrated in the timing chart of FIG. 17. As a result, the hand piece 82 is pneumatically disconnected from the tank 83, but the interior of the hand piece 82 communicates with the atmosphere for that period through the suction tube 84, the branch tube 86, and the solenoid valve 87. Thus, the negative pressure in the distal end of the hand piece 82 is released into the atmosphere. The probe attached to the hand piece 82 can therefore be quickly moved out of a body cavity, without damaging the normal tissues within the cavity.

Usually, powerful suction devices are installed in an operation room. The suction tube 84 can be connected to one of these suction devices, not to a suction pump 11 by way of the tank 83. Hence, the suction pump 11 can be dispensed with. Whether the tube 84 is connected to the suction pump 11 or the suction device, the suction can be controlled by means of the open/close valve 85. The open/close valve 85 is controlled in accordance with one of various suction modes. Among the suction modes are: a continuous suction mode, in which a negative pressure is continuously applied in the hand piece 82 as long as the foot switch 17 is on, and a simultaneous mode, in which a negative pressure is applied in the hand piece 82 only while the oscillator is being driven.

An ultrasonic treatment apparatus according a second embodiment of the present invention will now be described, with reference to FIGS. 18 to 21.

As is shown in FIG. 18, this apparatus comprises a hand piece 1 containing an ultrasonic oscillator (not shown), and a vibration-transmitting member 4 attached to the hand piece 1. The member 4 is vibrated due to the ultrasonic waves generated by the ultrasonic oscillator (not shown). The tip of the member 4, thus vibrated, is brought into contact with an affected tissue 34 on the inner wall of a body cavity, incising the tissue from the inner wall of the cavity. The hand piece 1 has a suction hole (not shown), which extends along the axis of the hand piece 1 and opens at the distal end thereof.

The proximal end of the hand piece 1 is connected a suction tank 12, with its end 13a passing through a cover 12a of the tank 12 into the suction tank 12. The suction tank 12 is connected to the inlet port 11a of a suction pump 11 by means of a tube 13b of the same type as the suction tube 13, said tube 13b passing through the cover 12a. Hence, the suction hole of the hand piece 1 is pneumatically connected to the pump 11 by the suction tube 13, the suction tank 12, and the tube 13b.

Figure 20:
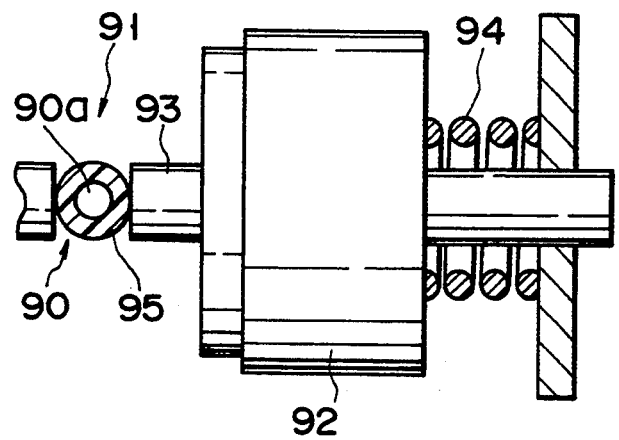
Figure 21:
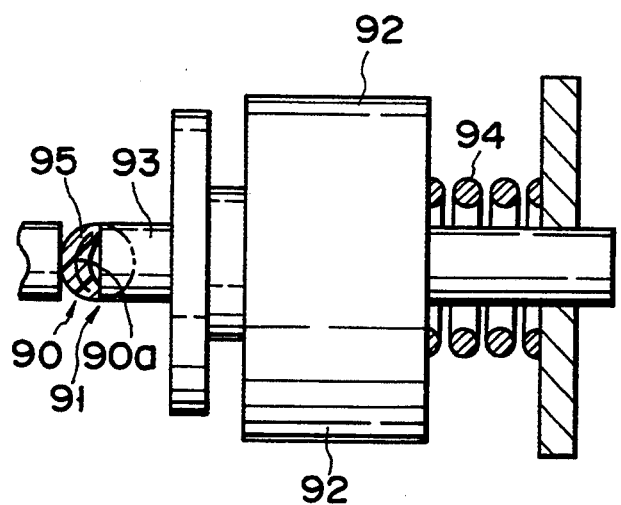

As is illustrated in FIG. 18, an open/close valve 91 is provided on the suction tube 13 for pneumatically connecting the hand piece 1 to the suction pump 11 or disconnecting the hand piece 1 therefrom. The valve 91 comprises that portion 90 of the suction tube 13 which extends between the hand piece 1 and the cover 12a of the tank 12, and a push-pull solenoid 92 which is shown in FIGS. 20 and 21. The push-pull solenoid 92 has a plunger 93 and a coil spring 94. When the solenoid 92 is energized, its plunger 93 moves backwards against the force of the coil spring 94, allowing the elastic tube 95 to regain its original shape as is shown in FIG. 20. As a result of this, the open/close valve 91 opens. When the solenoid 92 is de-energized, the coil spring 94 pushes the plunger 93 forward, thus collapsing the tube 95 used as suction tube 13, as is illustrated in FIG. 21. As a result, the open/close valve 91 is closed.

A branch tube 90b is connected, at one end, to that portion 90a of the suction tube 13 which extends between the open/close valve 91 and the suction tank 12. The other end of the branch tube 90b is connected to a release valve 96 which is a solenoid valve. When the open/close valve 91 is closed, the release valve 96 is opened, thereby to connect the portion 90a of the suction tube 13 to the atmosphere. Further, a pressure sensor 97 is connected on the tube 13b, for detecting the pressure within the tube 13b, i.e., the pressure within the suction tank 12. When the negative pressure in the tank 12 is increases above a predetermined value, it is determined that the tank 12, the suction tube 13, and/or the suction passes of the hand piece 1 and the vibration-transmitting member 4 are clogged.

A pressure-applying tube 100 is branched from that portion of the suction tube 13 which extends between the hand piece 1 and the open/close valve 91. The tube 100 is connected to the exhaust port 11b of the suction pump 11. A negative-pressure release valve 101 (i.e., a solenoid valve) is provided on the pressure-applying tube 100. A tube 11c is branched from that portion of the tube 100 which extends between the exhaust port 11b and the release valve 101, for exhausting a great part of the air from the pump 11 into the atmosphere. The remaining part of the air can, therefore, be supplied to the suction tube 13 through the valve 101. In other words, the valve 101 can apply a predetermined pressure to the suction tube 13. The valve 101 is usually closed. It is opened when the open/close valve 91 is closed, and then is closed upon lapse of a predetermined time.

The open/close valve 91, the release valve 96, and the negative-pressure release valve 101 are connected to a control circuit 102 and controlled by this circuit 102. The control circuit 102 has means for controlling the release of a negative pressure. An operation switch 103 is connected to the control circuit 102.

As can be understood from FIG. 18, all the components shown in this figure, except for the hand piece 1 and the vibration-transmitting member 4, constitute a suction system. The operation of this suction system will now be explained, with reference to the timing chart of FIG. 19.

As long as the operation switch 103 is off, the open/close valve 91 remains closed, thus pneumatically disconnecting the hand piece 1 from the suction tank 12. In this condition, the release valve 96 is opened, and the negative-pressure release valve 101 is closed.

Meanwhile, the suction pump 11 is driven. Hence, air is supplied from the atmosphere into the suction tank 12 through the release valve 96, and the load on the pump 11 is not so great as in the case where the inlet port 11a of the pump 11 is completely closed. Since the open/close valve 91 is closed, no suction force is applied in the suction path of the hand piece 1. Further, since the negative-pressure release valve 101 is closed, no compressed air can be supplied from the hand piece 1.

The surgeon inserts the vibration-transmitting member 4 into the body cavity through the endoscope channel already inserted into the body cavity, and brings the tip of the member 4 into contact with the affected tissue 34 as is shown in FIG. 18.

When the surgeon turns on the switch 103, the control circuit 102 opens the open/close valve 91 and closes the release valve 96. The negative-pressure release valve 101 remains closed. As a result, the negative pressure generated by the suction pump 11 is applied up to the tip of the vibrating-transmitting member 4 through the tube 13b, the suction tube 13, and the hand piece 1. Hence, as soon as the vibration-transmitting member 4 breaks stones or incises the affected tissue 34, the chips of stones or the tissues 34 are removed from the body cavity, are supplied through the suction tube 13, and are collected in the suction tank 12, along with the body fluids and the used perfusion liquid.

On the other hand, when the switch 103 is turned off, the control circuit 102 closes the open/close valve 91 and opens the release valve 96. As a result, the suction tube 13 is closed, and a suction force is no longer applied to the tip of the vibrating-transmitting member 4 through the tube 13b, the suction tube 13, and the hand piece 1. Further, air flows from the atmosphere into the suction tank 12 through the valve 96, the branch tube 90b, the portion 90a of the tube 13, and the end portion 13a thereof. Hence, the negative pressure in the tank 12 is maintained at a predetermined value, and no excessive loads are exerted on the suction pump 11. Because of the negative pressure maintained in the suction tank 12, a sufficient suction force can be build up before the open/close valve 91 is opened. It is therefore possible to start, at once, removing the broken stones, the affected tissues, the body fluids, etc. from the body cavity, since the negative pressure maintained in the suction tank 12 is neither too high nor too low.

The moment the switch 103 is turned off, the negative-pressure release valve 101 is opened. Thereafter, the valve 101 remains open for a predetermined period which is long enough for the tissue 34 to leave from the tip of the vibration-transmitting member 4. Hence, air is introduced from the exhaust port 11b of the pump 11 into the suction path of the hand piece 1 through the tube 100, the valve 101, and the suction tube 13, under the pressure which is slightly higher than the pressure within the body cavity. (To inflate the body cavity to make it easier for the surgeon to perform an operation, the air is supplied into the suction path of the hand piece 1 under a pressure which is, for example, 12 to 20 mmHg less than the pressure within the body cavity.) Since the negative pressure is released from the suction path of the hand piece, the tip of the vibration-transmitting member 4 can easily be removed from the tissue 34 which is attracted to the member 4. The member 4 never keeps attracting the tissue 34 even if the open/close valve 91 is closed by turning on the switch 103.

FIGS. 22 and 23 illustrate the open/close valve used in the suction system incorporated in a first modification of an ultrasonic treatment apparatus according to the second embodiment. This open/close valve 105 is a rotary solenoid, not a push-pull solenoid as in the second embodiment illustrated in FIG. 18. As is shown in FIGS. 22 and 23, the rotary solenoid 105 has a plate-shaped rotor 106. The rotor 106 is rotated between two positions. In the first position indicated by the solid lines in FIG. 23, the rotor 106 collapses a elastic tube 95 used as a suction tube, thereby closing the suction tube. In the second position indicated by the broken lines in FIG. 23, the rotor 106 releases the tube 95, whereby a fluid can pass through the suction tube. When set in the first position, the rotor 106 applies a force to the suction tube in the axial direction of the rotor 106, and the rotary solenoid needs to have but the torque smaller than in the case where it applies the force in any other direction.

FIGS. 24 and 25 illustrate the open/close valve 107 used in the suction system incorporated in a second modification of an ultrasonic treatment apparatus according to the second embodiment. This open/close valve 107 is an electric motor, not the rotary solenoid 105 of the type used in the first modification, shown in FIGS. 22 and 23. As is shown in FIGS. 24 and 25, a plate-shaped rotor 106 is connected to the shaft of the motor 107. The rotor 106 is rotated between two positions. In the first position indicated by the solid lines in FIG. 25, the rotor 106 collapses an elastic tube 95 used as a suction tube, thereby closing the suction tube. In the second position indicated by the broken lines in FIG. 25, the rotor 106 releases the tube 95, whereby a fluid can pass through the the suction tube. When set in the first position, the rotor 106 applies a force to the suction tube in the axial direction of the rotor 106. Thus, the electric motor 107 needs to have but a torque smaller than in the case where it applies the force in any other direction.

Figure 26:
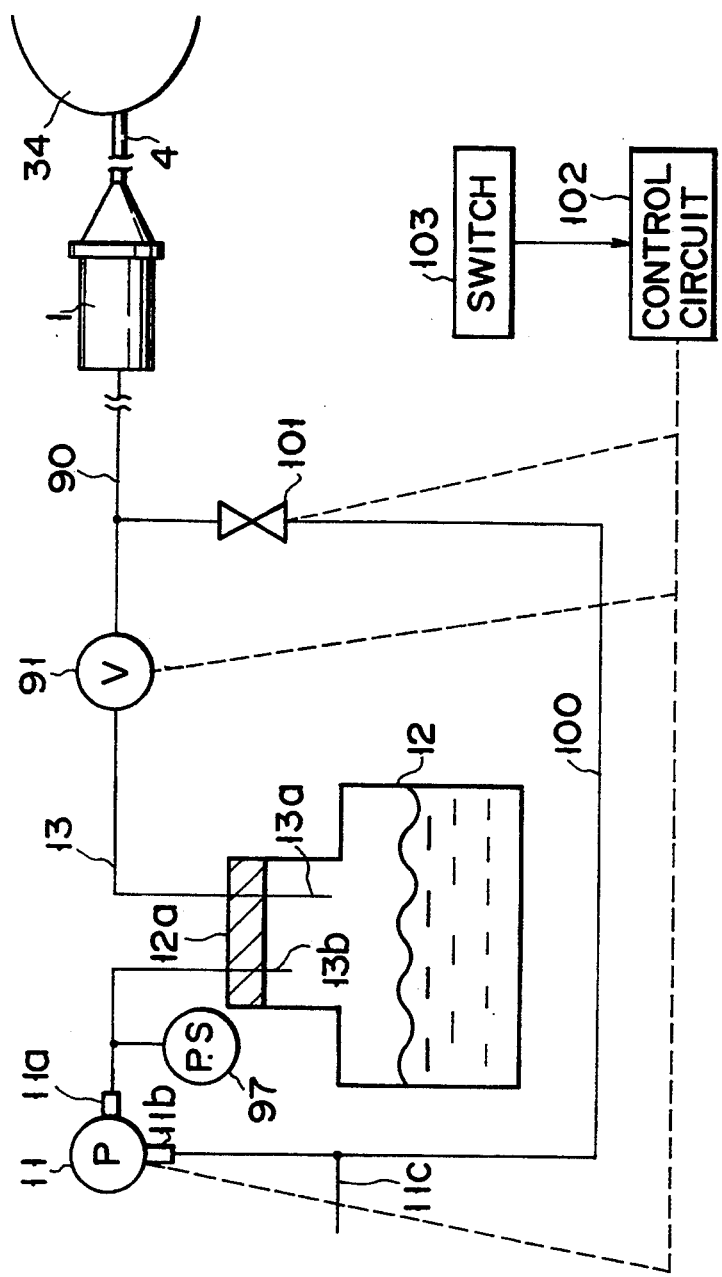
FIGS. 26 and 27 illustrate a third modification of the second embodiment.
Figure 27:
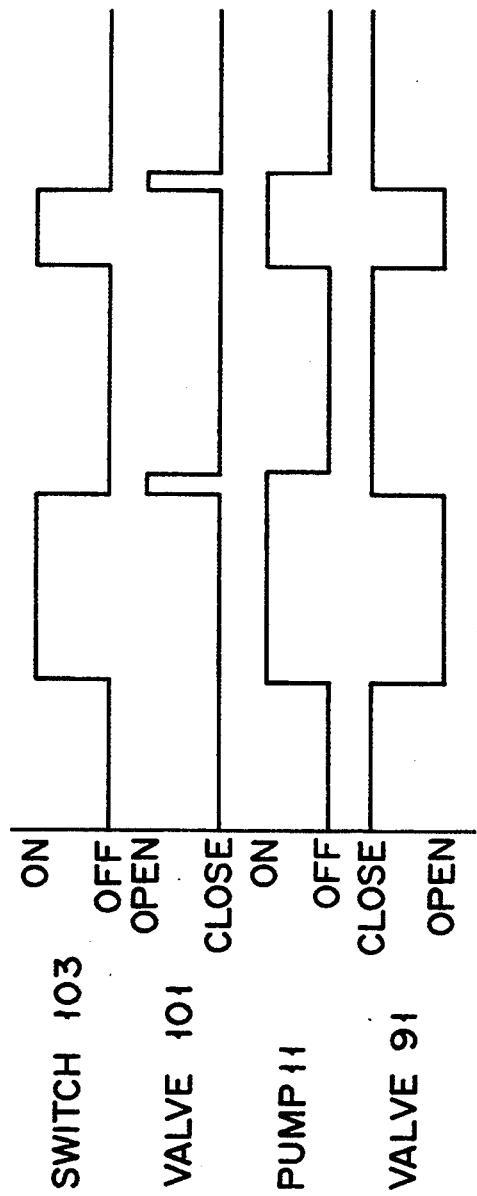

FIGS. 26 and 27 show a third modification of the second embodiment. The third modification is similar to the second embodiment illustrated in FIG. 18, but is different in that the control circuit 102 controls the suction pump 11, too. More specifically, as is evident from the timing chart of FIG. 27, the circuit 102 opens the negative-pressure release valve 91 upon lapse of a predetermined period after the surgeon turns off the switch 103, and then closes the negative-pressure release valve 91 and, at the same time, stops the suction pump 11. Since the negative-pressure release valve 101 is opened after the open/close valve 91 is closed, the pump 11 is connected to the hand piece 1 by the pressure-applying tube 100, the valve 101, and the suction tube 13. Hence, even after the open/close valve 91 has been closed, air is supplied from the exhaust port 11b of the pump 11 to the suction path of the hand piece 1 under a pressure which is slightly higher than the pressure within the body cavity. As a result of this, the negative pressure is released from the suction path of the hand piece, and the tip of the vibration-transmitting member 4 can easily be removed from the tissue 34 which is attracted to the member 4.

Even after the suction pump 11 is stopped, an appropriate negative pressure, neither too high nor too low, is maintained in the suction tank 12. Therefore, a sufficient suction force is build up before the open/close valve 91 is opened. Hence, it is possible to start, at once, affected tissues, body fluids, etc., from the body cavity.

Figure 28:
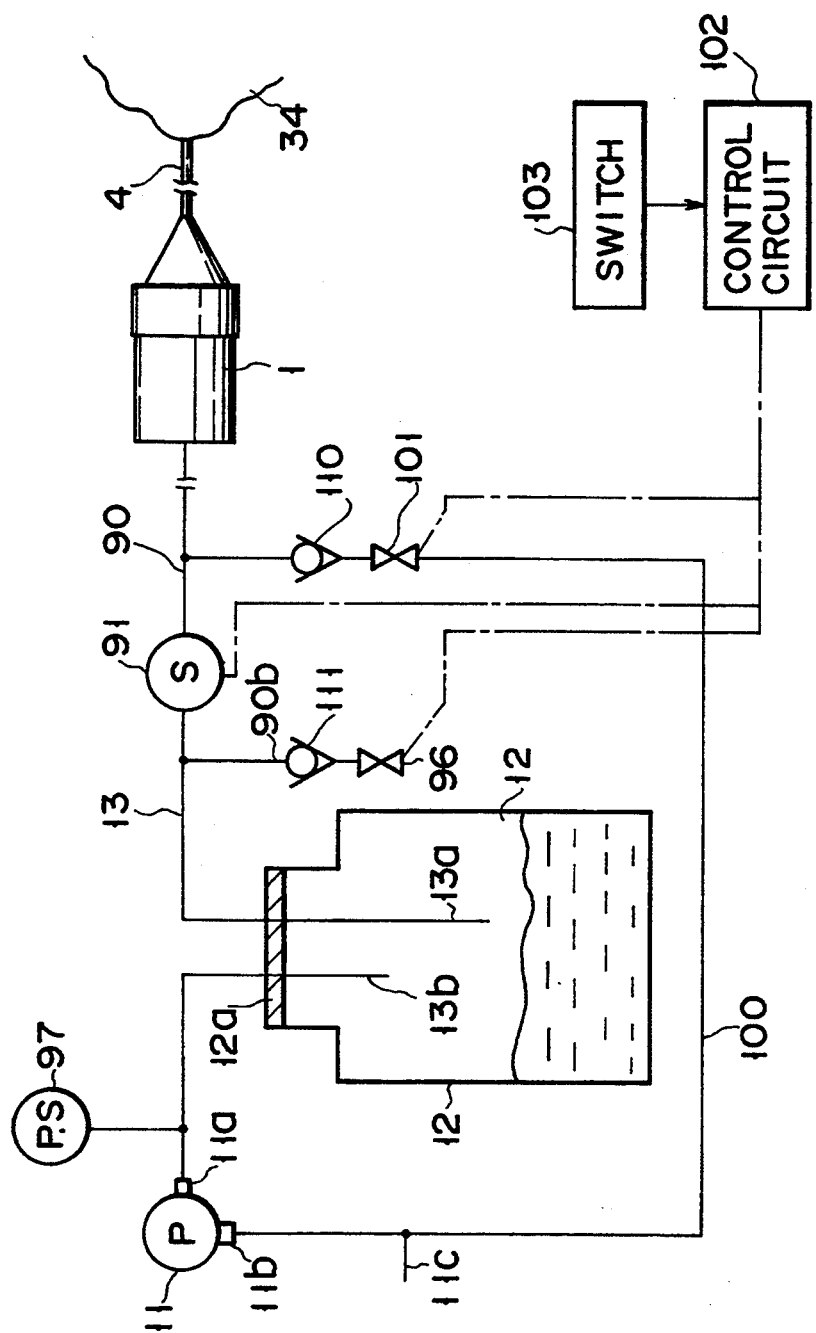
FIG. 28 shows the suction system used in a fourth modification of the second embodiment.

FIG. 28 shows the suction system incorporated in a fourth modification of the second embodiment. This suction system is similar to the suction system shown in FIG. 18, but is different in two respects. First, a check valve 110 is connected between the suction tube 13 and the negative-pressure release valve 101, allowing air to flow in one direction only, that is, from the suction pump 11 to the hand piece 1. Second, a check valve 111 is provided on the branch tube 90b connecting the release valve 96 to the suction tube 13, thereby to prevent any fluid flowing from the suction tube 13 into the release valve 96.

The check valves 110 and 111, blood, body fluids, tissues, or the like, if flowing to them, prevent the blood, body fluids, or the like from flowing into the release valve 96 or into the negative-pressure release valve 101. This greatly helps to prevent malfunction of the valve 96 or 101. Also, does this prevent the corrosion of the valves 96 and 101, prolonging the lifetime thereof. Further, since no foreign matters flow into the pressure-applying tube 100 through the valve 96 or 101, there is no risk that the tube 100 is clogged.

Figure 29:
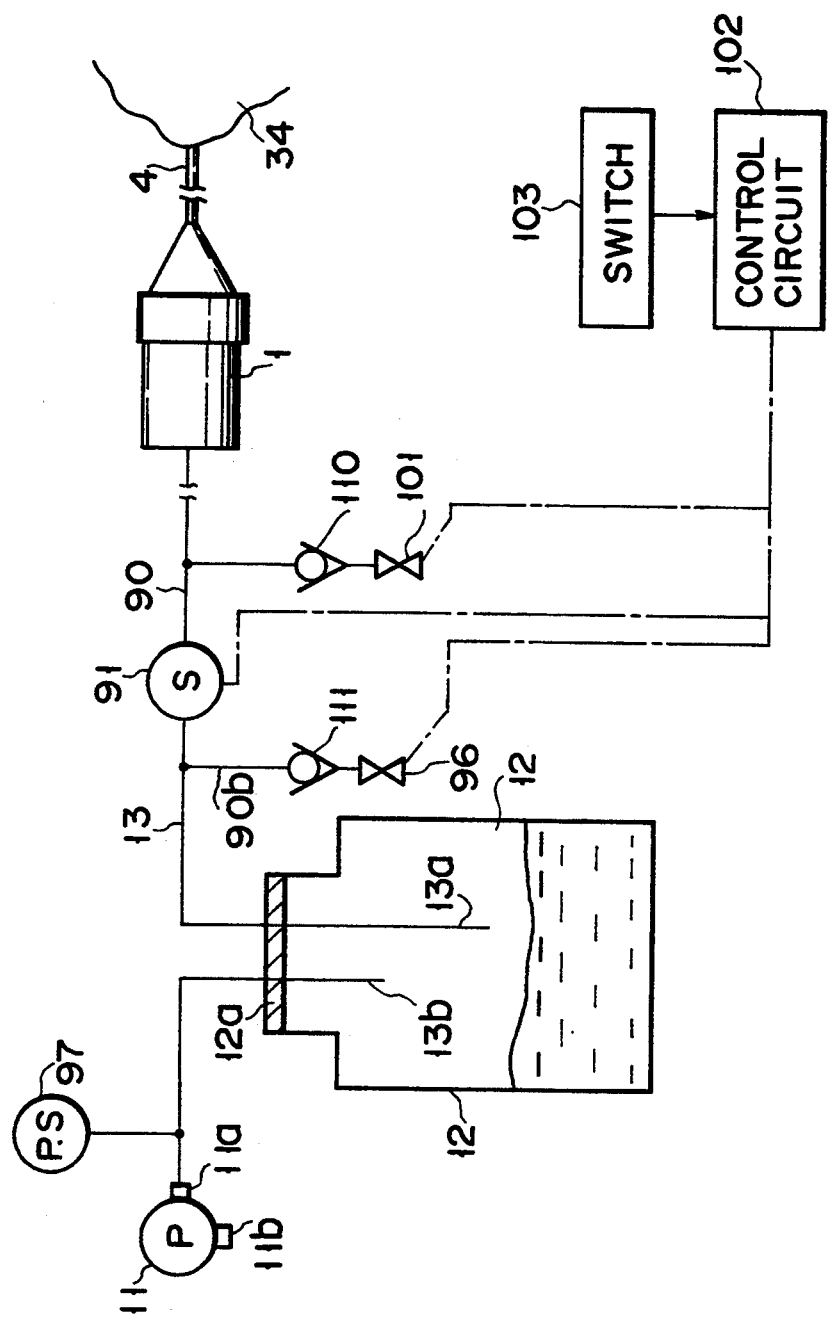
FIG. 29 shows the suction system used in a fifth modification of the second embodiment.

FIG. 29 shows the suction system incorporated in a fifth modification of the second embodiment. This suction system is identical to the system shown in FIG. 28, except that there are no component corresponding to the pressure-applying tube 100. The negative-pressure release valve 101 can be opened to the atmosphere. Also, the exhaust port 11b of the suction pump 11 is opened to the atmosphere. When the open/close valve 91 is closed, thus stopping the application of the negative pressure to the suction path of the hand piece, the control circuit 102 opens the negative-pressure release valve 101 for a predetermined period. During this period, the negative pressure is released from the hand piece 1 into the atmosphere. The predetermined period must be long enough to release the negative pressure completely from the hand piece 1.

The suction system of the fifth modification is simple in comparison with the system illustrated in FIG. 28, and can yet achieve the same advantage. With this system of FIG. 29 it is possible to connect the negative-pressure release valve 101 to a compressor (not shown) by means of a pressure-applying tube (not shown).

FIGS. 30 and 31 illustrate an endoscope 114 which can be used in combination with the ultrasonic treatment apparatus according to the present invention. As is shown in FIG. 30, the endoscope 114 comprises an operation section 115 and an insertion section 116 which are integrally formed. An objective unit 117 is connected to the operation section 115. The insertion section 116 is inserted through a sheath 118. The proximal end of the sheath 118 is fastened to the operation section 115 in watertight fashion. A water-supplying port 120 is made in the proximal end portion of the sheath 118.

A tool-guiding channel 121 passes straight through the insertion section 116. The channel 121 is formed of a distal section 121a and a proximal section 121b. The proximal section 121b has an inside diameter greater than that of the distal section 121a, and can receive the distal-end portion of a probe sheath 122 of the ultrasonic treatment apparatus. A seal member 123 is removably attached to the distal end of the channel 2, achieving watertight sealing between the channel 121 and the probe sheath 122. A cock 124 is provided in the proximal section 121b of the tool-guiding channel 121. The cock 124 has a core 125 which allows the passage of the probe sheath 122. The core 125 collapses when the sheath 122 is pulled from it, thereby closing the distal section 121b of the channel 121.

The hand piece 1 of the ultrasonic treatment apparatus comprises an ultrasonic oscillator 2 and a cover 126 covering the oscillator 2. The cover 126 is coaxially connected to the probe sheath 122. An ultrasonic probe 4 is connected to a horn 3, which in turn is connected to the ultrasonic oscillator 2. A liquid-supplying port 127 is coupled to the distal-end portion of the cover 126. A seal member 128 is set in the distal-end portion of the cover 126, for blocking a perfusion liquid flowing from the port 127 into the ultrasonic oscillator 2.

When the proximal section 121b of the tool-guiding channel 121 is inserted into the proximal-end portion of the probe sheath 122, the ultrasonic oscillator 2 is inserted into the distal section 121a of the channel 121, as is illustrated in FIG. 31. The channel 121 and the sheath 122 are coaxial with each other. The distal section 121 has the same inside diameter as the probe sheath 122. The channel 121 and the sheath 122 need not be completely coaxial, provided that the ultrasonic probe 4 does not vibrate. Further, the inside diameters of the distal section 121 and the sheath 122 need not be exactly the same.

To use the endoscope in combination with the ultrasonic treatment apparatus, the distal-end portion of the probe sheath 122 is inserted into the proximal section 121b of the channel 121, this connecting the apparatus with the endoscope. Then, the ultrasonic probe 4 is coaxially coupled to the distal section 121a of the tool-guiding channel 121. Since the probe sheath 122 has the same inside diameter as the distal section 121a of the channel 121, there will be no play of the probe 4 in the tool-guiding channel 121.

The seal member 123, which is mounted on the circumference of the sheath 122, prevents the perfusion liquid supplied through the port 120 or 127 into the tool-guiding channel 121, from leaking from the endoscope or the hand piece 1. The ultrasonic probe 4 has a though hole extending along the axis of the probe 4. It is through this hole that the incised tissues, the broken stones, and the like are removed from a body cavity, together with the perfusion liquid.

FIG. 32A is a sectional view showing a first modification of the junction between the hand piece 1 and the endoscope 114. This junction is suitable for use in the case where a high-frequency current is supplied through the ultrasonic probe 4 to a tool attached to the distal end of the probe 4, thereby to harden an affected tissue existing in a body cavity. To protect the surgeon against an electric shock, the the pipe 130, which forms the tool-guiding channel 121 and the probe sheath 122 are made of electrically insulative material such as ceramics or plastics. An O-ring 131 is mounted on the distal-end portion of the probe sheath 122. The O-ring 131 fills the gap between the sheath 122 and the inner circumference of the proximal end of the channel 121, not only holding the sheath 122 steadily, but also accomplishing reliable watertight sealing between the channel 121 and the sheath 122. Hence, neither the cock 124 nor the core 125 needs to be high-precision ones, which helps to reduce the manufacturing cost of the endoscope. Further, even if the O-ring 131 is made of inexpensive metal, it can prevent leakage of a high-frequency current.

FIG. 32B illustrates a second modification of the junction. In this modification, too, the pipe 130 which forms the tool-guiding channel 121 is made of electrically insulative material. Further, the main body 124a and core 125 of the cock 124 are made of electrically insulative material, too. Since not only the channel 121, but also the cock 124 is electrically insulative, the surgeon is protected from an electric shock while a high-frequency current is flowing through the ultrasonic probe 4.

FIG. 32C shows a third modification of the junction, which is characterized in that the probe sheath 122 has a thin portion 132 which is located in the proximal end portion of the channel 121 when the sheath 122 is inserted in the channel 121. An O-ring 133 is mounted on the thin portion 132, filling the gap between thin portion 132 and the inner circumference of the channel 121. The hand piece 1 can be moved, with a small force, thus moving the ultrasonic probe 4 back and forth, for a distance equal to or shorter than the length of the thin portion 132. When the surgeon further pushes the sheath 122 forward, the O-ring 133 is clamped between the inner circumference of the channel 121 and the thick portion of the sheath 122, making it hard for the surgeon to move the sheath 122 forward unless he or she applies a greater force.

Figure 32D:
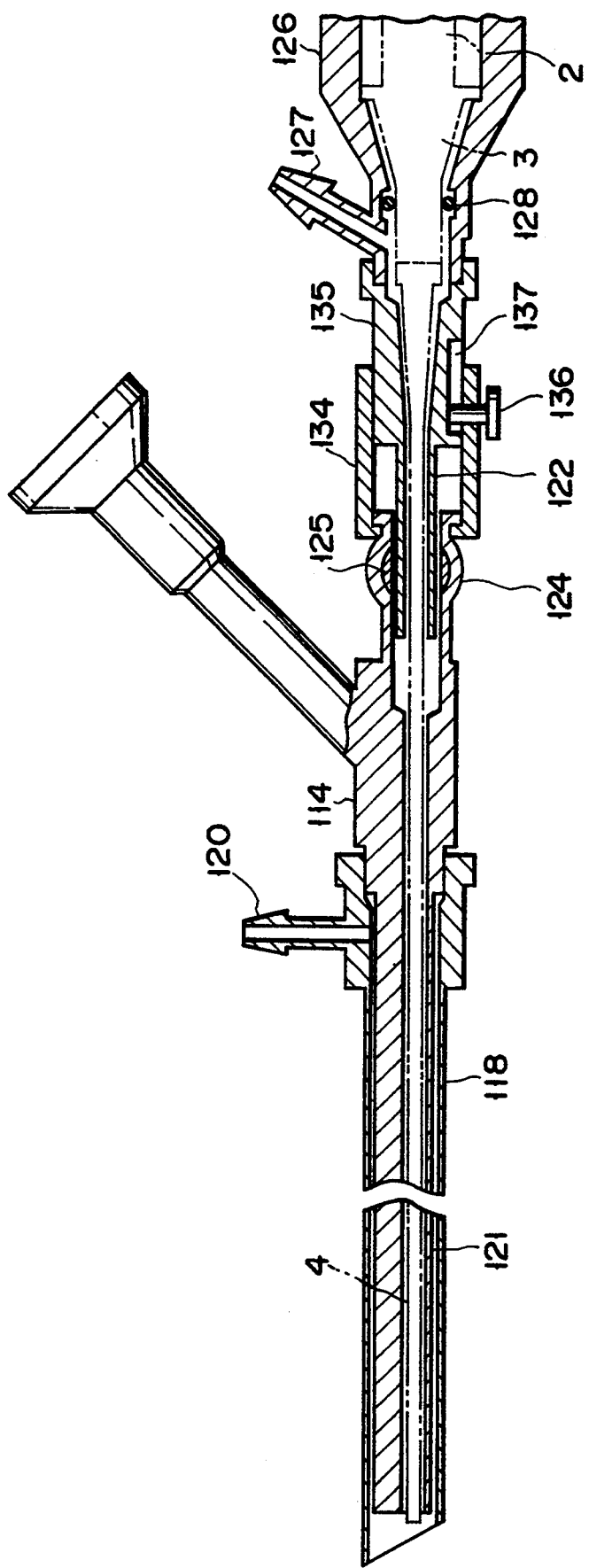
FIG. 32D is a sectional view showing a fourth modification of the junction.

FIG. 32D shows a fourth modification of the junction, which is characterized by a hollow cylindrical guide 134 connected to the proximal end of the tool-guiding channel 121. The guide 134 guides the probe sheath 122 smoothly, without a play, only back and forth to move the ultrasonic probe 4 in the same direction. The guide 134 has a pin 136 protruding into a guide groove 137 made in the outer circumference of the proximal portion 135 of the sheath 122 and extending parallel to the axis of the sheath 122. The sheath 122 can therefore be moved until the pin 136 abuts on either end of the guide groove 137. Hence, the ultrasonic probe 4 can be moved back and forth through the endoscope 114 for a distance equal to the length of the guide groove 137, not excessively beyond that distance.

FIG. 33A to 33C shows a fifth modification of the junction, which is characterized in various respects. First, a tool-guiding channel 121 is located in an endoscope 114. Second, a cock 124 is connected to the proximal end of the tool-guiding channel 121. Third, a rubber cap 123 is connected to the proximal end of the cock 124 for watertight sealing. Fourth, a sheath 122 and a probe 4 are inserted into the channel 121 through the rubber cap 123. Fifth, an O-ring 133 is mounted on the proximal end of the channel 121 and located near the cock 124. Further, the probe 4 is fastened to an ultrasonic oscillator 2.

The sheath 122 is secured to the hand piece 1 by a connecting sheath 135. When the hand piece 1 is moved back and fourth to move the probe 4 in the same direction, the probe 4 and the sheath 122 move together, back and forth, in the tool-guiding channel 121 of the endoscope 114. Since the rubber cap 132 and the O-ring 133 always contact the probe sheath 122, thus preventing the perfusion liquid from leaking outside as it is supplied from the water-supplying port 120 to the tool-guiding channel 121. When the probe 4 is not inserted into the channel 121 of the endoscope 114, a lever 129 fastened to the cock 124 is rotated, thus rotating the core 125 to the closed position. As a result, the tool-guiding channel 121 remains watertight.

As is illustrated in FIG. 33B, a guide 134 is connected to the proximal end of the main body 114a of the endoscope 114. The guide 134 holds the sheath 135, thus controlling the movement of the sheath 135 such that the probe 4 remains coaxial with the channel 121 all the time the probe 4 is moved back and forth. The guide 134 is fixed to the main body 114a. Instead, it can be removably connected to the main body 114a.

As is shown in FIG. 33C, the connecting sheath 135 has a square cross section, and fitted in the hole 134a made in the guide 134. Since the hole 134a also has a square cross section, the probe 4 cannot rotate while it is moved back and forth.

A stopper 136a is connected to the proximal end of the guide 134. The stopper 136a abuts on the distal end of a groove 137 made in the outer circumference of the sheath 135, thereby preventing the probe 4 from slipping out of the endoscope 114.

A stepped portion 135a is formed at the front of the probe sheath 122, and a stepped portion 123a is formed at the rear of the rubber cap 123. The probe 4 can be moved forward until the stepped portion 135a abuts on the stepped portion 124a, preventing an excessive forward movement of the prove 4.

FIGS. 34A and 34B illustrate a sixth modification of the junction, which is designed for connecting the endoscope 114 and the straight long probe 4c or the tapered long probe 4d. When the straight long probe 4c is used, a prove sheath 119a is removably attached to a hand piece 1, surrounding the probe 4c, as is shown in FIG. 34A. The sheath 119a has an axial hole whose shape is complementary to that of the straight long probe 4. When the tapered long probe 4d is used, a longer probe sheath 119b is removably connected to the hand piece 1, surrounding the probe 4d, as is shown in FIG. 34B. The sheath 119b has an axial hole whose shape is complementary to that of the tapered long probe 4d. No matter whether the probe 4c or the probe 4d is used, the distal-end portion of the probe is located at the same position when the probe is moved most forward, as is evident from FIGS. 34A and 34B.

FIG. 35A and 35B illustrate a seventh modification of the junction of the guide 134 and the sheath 135. In this modification, a guide groove 137 is made in one side of the sheath 135 and extending parallel to the axis of the sheath 135, and the guide 134 has a pin 236 projecting into the guide groove 137. Therefore, as is shown in FIG. 35B, the sheath 122 can neither rotate or move back or forth for a distance longer than the guide groove 137.

FIGS. 36 and 37 illustrate a modification of the endoscope. This modified endoscope is characterized in two respects. First, the insertion section 116 comprises an outer tube 140, an inner tube 130 contained in the outer tube 140 for guiding the ultrasonic probe 4, an optical channel 139 contained in the tube 140 and extending parallel to the tube 130, and relay lenses 138 held in the channel 139 and spaced apart from one another. Second, optical fibers 141 extend through the outer tube 140, filling up the space defined by the inner circumference of the tube 140, the tube 130, and the optical channel 139.

FIG. 38 and 39 show a second modification of the endoscope. In this modified endoscope, the insertion section 116 comprises a tube 130 serving as tool-guiding channel 121, an optical channel 139 containing relay lenses 138, and two tubes 142 containing optical fibers 141 for transmitting illumination light. The tube 130, the optical channel 139, and the tubes 142 are bound together by means of adhering, soldering, or welding. The tube 130 is made of electrically insulative material, and a high-frequency current flows through the ultrasonic probe 4 extending through the tube 130. Hence, it is advisable that the tube 130 be adhered to the optical channel 139 and the tubes 142 after the channel 139 and the tubes 142 have been bound together by either soldering or welding.

Figure 40:
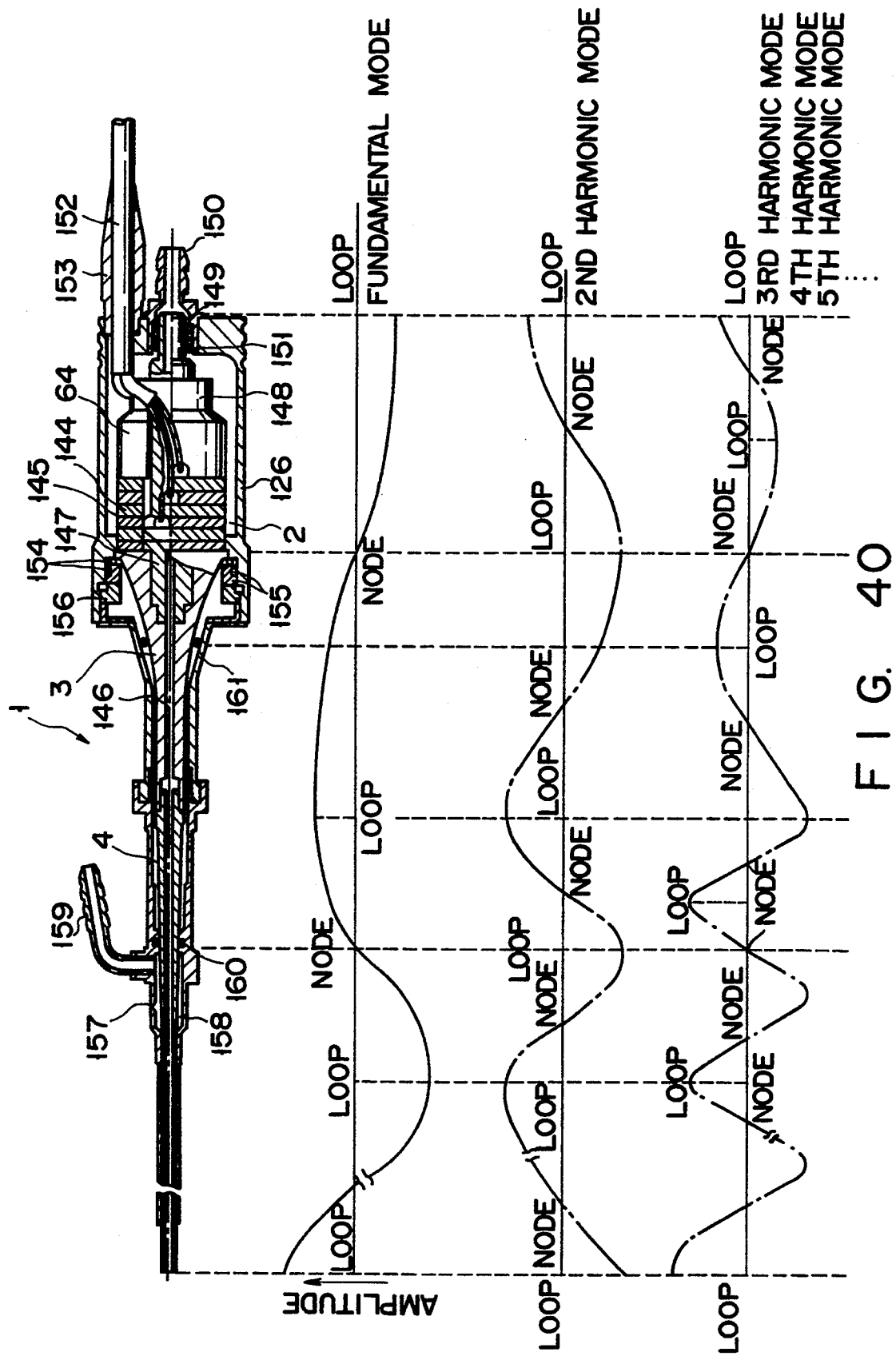
FIG. 40 illustrates a hand piece incorporated in an ultrasonic treatment apparatus according to a third embodiment of the invention, and also the various vibration modes in which the hand piece can be operated.

FIG. 40 shows an ultrasonic treatment apparatus according to a third embodiment of the invention. To be specific, this figure shows the hand piece 1 of the apparatus and also the various vibration modes in which the hand piece 1 can be operated.

As is shown in FIG. 40, the hand piece 1 comprises an ultrasonic oscillator 2, a horn 3 connected to the ultrasonic oscillator 2, and a probe or vibration-transmitting member 4 connected to the horn 3. The oscillator 2 is located within a cover 126 which serves as a grip. The oscillator 2 comprises a plurality of piezoelectric elements 144 and a plurality of electrodes 145 interposed among the elements 144. The horn 3 can amplify the vibration of the ultrasonic oscillator 2. The horn 3, piezoelectric elements 144, electrodes 145, and the metal block 64 are aligned coaxially and have concentric holes. Thee holes form a passage. A bolt 147 having an axial through hole extends through this passage. The distal end of the bolt 147 is set in screw engagement with the horn 3. A nut 148 is mounted on the proximal end of the bolt 147, so that the piezoelectric elements 144 and the electrodes 145 are firmly fastened together between the horn 3 and the metal block 64.

A hollow cylindrical member 149 is integrally formed with the proximal end of the bolt 147. The member 149 protrudes through the screw hole made in the proximal end wall of the cover 126. A connector 150 is set in screw engagement with the screw hole of the cover 126. O-rings 151 are mounted on the hollow cylindrical member 149, achieving watertight sealing between the member 149 and the cover 126. A suction tube (not shown) is connected to the proximal end of the connector 150.

A power-supplying cord 152 is connected to the electrodes 145 for applying a high-frequency voltage on the piezoelectric elements 144. The cord 152 passes through a straight protective tube 153 which has a distal-end portion set in screw engagement with the end wall of the cover 126.

The ultrasonic oscillator 2, thus assembled, is secured to the cover 126 by means of a seal 155 and a fastening member 156. The seal 155 has an O-ring 154 which accomplishes sealing between the horn 3 and the cover 126.

A front cover 157 is connected to the distal end of the cover 126. Extending through the front cover 157 is the vibration-transmitting member 4. A space is provided between the member 4 and the inner circumference of the front cover 157. To supply a perfusion liquid into this space, a liquid-supplying tube (not shown) is attached to the water-supplying port 159 mounted on the intermediate portion of the front cover 157. An O-ring is mounted on that portion of the vibration-transmitting member 4 which is more proximal than the port 159.

Further, in the third embodiment, a second O-ring 161 is mounted on the outer circumference of the horn 3, resiliently connecting the horn 3 to the cover 126, as is illustrated in FIG. 40.

In the hand piece 1, the ultrasonic vibration generated by the oscillator 2 and propagating in the axial direction of the hand piece 1 is magnified by the horn 3. The ultrasonic vibration, thus magnified, is applied to the vibration-transmitting member 4. The tip of the member 4 is vibrated, and can therefore cut or emulsify an affected tissue or can break stones in a body cavity.

The ultrasonic oscillator 2 can vibrate in various modes which are represented in the graph, i.e., the lower half of FIG. 40. As may be understood from the graph, the oscillator 2 has indefinite number of vibration modes. Among these vibration modes are: the fundamental mode; the second harmonic mode in which ultrasonic waves have half the length of those in the fundamental mode; the third harmonic mode in which ultrasonic waves have a third of the length of those in the fundamental mode; and the fourth harmonic mode in which ultrasonic waves have a quarter of the length of those in the fundamental mode. The O-ring 154 of the seal ring 155 and the first O-ring 160, which support the cover 126 and the front cover 157, respectively, are located at two nodes of the fundamental vibration mode. The waves of the even-numbered harmonic modes (e.g., the waves of the second and fourth harmonic modes), whose loops are located at the O-rings 154 and 160, are prevented from moving, and the vibration of the even-numbered harmonic modes are relatively weak.

As is evident from FIG. 40, the second O-ring 161 is located at the loop of ultrasonic vibration of the third harmonic mode, which resiliently connects the horn 3 to the front cover 157. Hence, the second O-ring 161 suppresses the displacement of the waves of the third harmonic mode, whereby the vibration of the third harmonic mode is weak. The second O-ring 161 is located between a loop and a node of the fundamental-mode vibration, the displacement of these waves is far form nil. The fundamental-mode vibration is therefore intense. Further, the second O-ring 161 is made of elastic material. Therefore, the fundamental-mode vibration is not attenuated at all.

As has been explained, the vibrations of the second, third and fourth harmonic modes are much more suppressed than the fundamental-mode vibration. The vibrations of the fifth harmonic mode and that of any lesser harmonic mode are very weak, and consume but a fraction of the electric energy supplied to the ultrasonic oscillator 2.

Hence, the vibration-transmitting member 4 is vibrated largely in the fundamental mode, and the power wasted by the vibrations of the harmonic modes is very little. The ultrasonic treatment apparatus shown in FIG. 40 can therefore be said to be energy-efficient. In addition, the piezoelectric elements 144 (i.e., the vibrating elements) of the oscillator 2 require but very little power, and the apparatus is safe in terms of electric shock.

Figure 41:
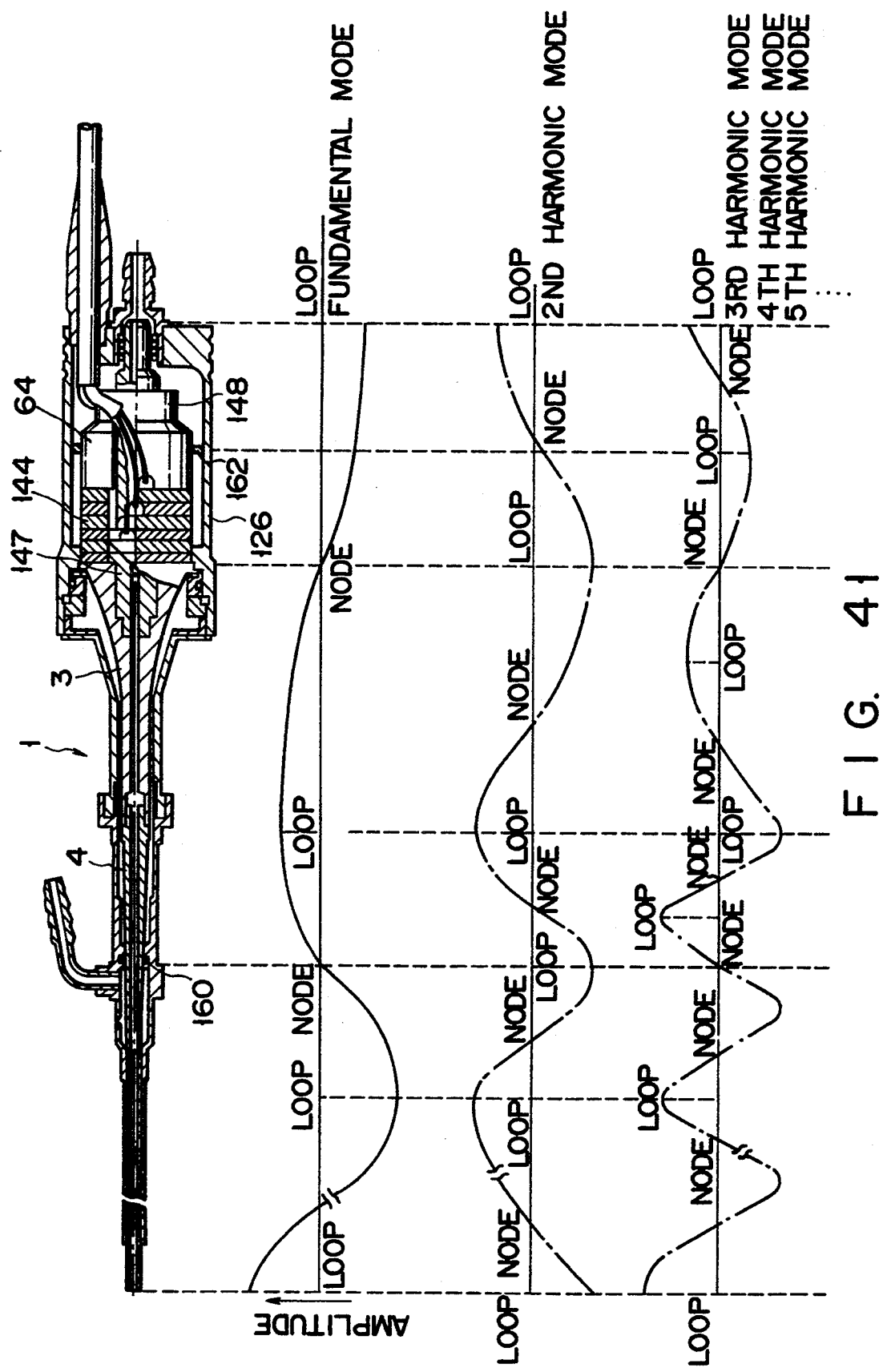
FIG. 41 shows a modification of the hand piece shown in FIG. 40, and the various vibration modes in which the modified hand piece can be operated.

FIG. 41 shows a modification of the hand piece shown in FIG. 40 and the various vibration modes of this modified hand piece. The same components as those of the hand piece of FIG. 40 are designated at the same numerals in FIG. 41 and will not be described in detail.

The hand piece 1 shown in FIG. 41 is characterized by an elastic ring 162 protruding inwards from the inner circumference of the cover 126. The ring 162 is located at that loop of the ultrasonic vibration of the third harmonic mode which exists in the metal block 64. Since the ring 162 is mode of elastic material, it does not prevent an axial movement of the metal block 64, but allows the block 64 to move a little along its axis. Hence, the elastic ring 162 also serves to reduce the intensity of the waves of the third harmonic mode.

Figure 42:
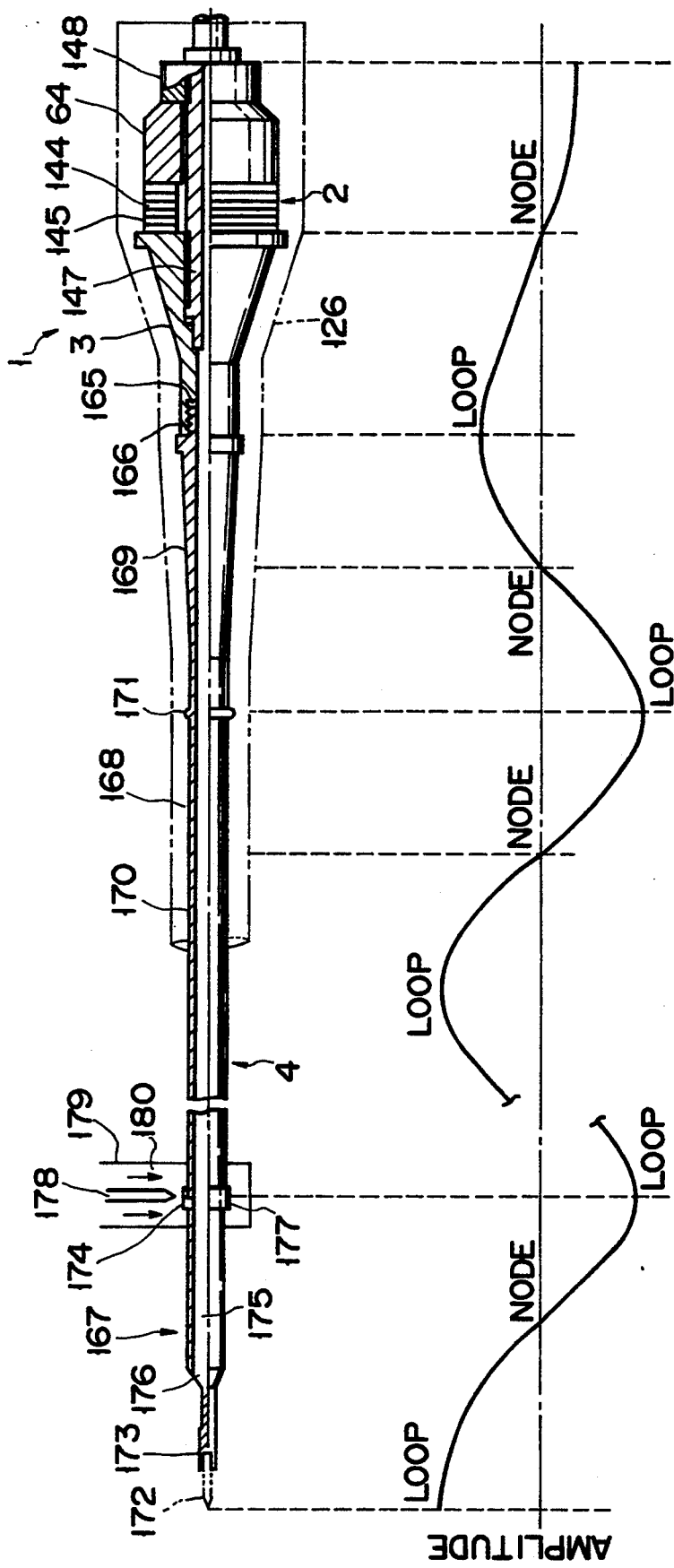
FIG. 42 is a partially sectional view showing a hand piece incorporated in an ultrasonic treatment apparatus according to a fourth embodiment of the invention, and also shows the waveform of the ultrasonic vibration of the hand piece.

FIG. 42 illustrates the hand piece 1 incorporated in an ultrasonic treatment apparatus according to a fourth embodiment of the invention. It also shows the waveform of the ultrasonic vibration the hand piece generates.

As is shown in FIG. 42, the hand piece 1 comprises an ultrasonic oscillator 2, a horn 3, and a probe or a vibration-transmitting member 4 for transmitting the ultrasonic vibration generated by the oscillator 2. The oscillator 2 comprises a plurality of piezoelectric elements 144 and a plurality of electrodes 145 interposed among the elements 144. The horn 3 is connected to the oscillator 2 for amplifying the the vibration of the oscillator 2. The horn 3, piezoelectric elements 144, electrodes 145, and the metal block 64 are aligned coaxially and have concentric holes. Thee holes form a passage. A bolt 147 having an axial through hole extends through this passage. The distal end of the bolt 147 is set in screw engagement with the horn 3. A nut 148 is mounted on the proximal end of the bolt 147, so that the piezoelectric elements 144 and the electrodes 145 are firmly fastened together between the horn 3 and the metal block 64.

The horn 3 has a female screw 165 on its distal-end portion. The vibration-transmitting member 4 has a male screw 166 on its proximal-end portion. The proximal-end portion of the member 4 is put in screw engagement with the distal-end portion of the horn 3.

The vibration-transmitting member 4 has a tool holder 167 and a tubular shaft 168. The shaft 168 is formed of a proximal member 169 and a tubular member 170. The proximal member 169 has been made by either machining or sintering. The members 169 and 170 are coupled together by means of, for example, tungsteninert-gas (TIG) welding, thus forming a first junction 171.

The tool holder 167 holds a treatment tool 173 having a blade 172 at the tip. The proximal-end portion 174 of the tool holder 167 is a hollow cylinder having an outside diameter equal to or slightly greater than that of the tubular member 170. The proximal-end portion 174 of the tool holder 167 has an axial passage 175, which opens at the distal end 176. The proximal-end portion 174 is inserted into or abuts on the distal end of the tubular member 170, and is coupled to the tubular member 170 by means of, for example the TIG welding, thus forming a second junction 177.

The passage 175 of the tool holder 167 communicates with the passage formed in the shaft 168, whereby the passages of the tool holder and shaft 168 define a path. This path can be used as either a liquid-supplying path for supplying a perfusion liquid toward the opening 176, or a suction path for removing incised tissues, broken stones, or the like from a body cavity.

As has been described, the tool holder 167 and the shaft 168 are connected at the second junction 177 by means of, for example, the TIG welding. It will briefly be explained how to connect the holder 167 and the shaft 168. First, a welding torch 178 is placed near the second junction 177 as is shown in FIG. 42. Then, a hollow cylindrical shield 179 is positioned, surrounding the torch 178, to prevent oxidation of the vibration-transmitting member 4 which is made of titanium alloy. Inert gas, such as argon gas (Ar), is supplied into the shield 179 in the direction of the arrows shown in FIG. 42. The torch 178 is lighted, and the flame is applied to the second junction 177, while the inert gas is continuously supplied to the junction 177 through the hollow cylindrical shield 179. The abutting ends of the tool holder 167 and the shaft 168 are fused together because of the heat applied from the torch 178.

As is evident from FIG. 42, the junction between the horn 3 and the member 4, the first junction 171, and the second junction 177 are located at the loops of the ultrasonic vibration of the vibration-transmitting member 4. As is generally known in the art, less stress is applied to those portion of any member which are located at the loops of ultrasonic vibration, than to those portions which are located at the nodes of the vibration. Hence, a relatively small stress acts on the junction between the horn 3 and the member 4, the first junction 171, and the second junction 177—all being mechanically weak. This helps to prevent damage to these junctions.

The ultrasonic oscillator 2 has a length of $\lambda/2$, where $\lambda$ is the wavelength of the fundamental-mode vibration. The vibration-transmitting member 4 has a length of $n/\lambda$, where n is an integer. Therefore, the cutter 172 is located at a loop of the ultrasonic vibration.

Like the shaft 168, the tool holder 167 is made by machining or sintering. Both the tool holder 167 and the shaft 168 are covered by the cover 126 as is indicated by the two-dot, one-dash lines in FIG. 42.

Figure 43:
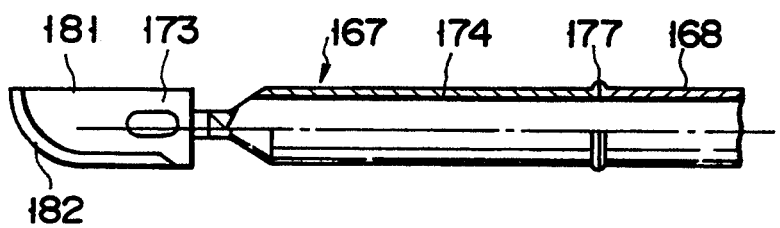
FIG. 43 is a partially sectional view showing the treatment tool attached to the hand piece illustrated in FIG. 42.
Figure 44:
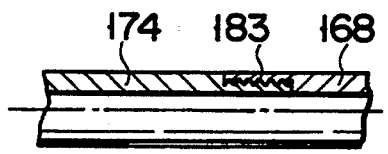
FIG. 44 is a partially section view showing the junction between the treatment tool and the vibration-transmitting member of the hand piece.

As is shown in FIG. 43, the treatment tool 173 is comprised of a shaft and a knife 181. The knife 181 is removably attached to the shaft, and has a sharp blade 182. The proximal end 174 of the tool holder 167 is welded to the shaft 168, at the second junction 177. Instead, as is shown in FIG. 44, the proximal end 174 can be attached to the shaft 168 by means of screw engagement. This method of connecting the holder 167 with the tubular shaft 168 makes it easy for the surgeon to exchange various knives, one with another.

The knife 181, which is attached to the vibration-transmitting member 4 is vibrated when the ultrasonic oscillator 2 is driven. Therefore, the knife 181 can cut tissues better than any knife which is not subjected to ultrasonic vibration.

Six treatment tools which can be used, in place of the tool 173 shown in FIG. 43, will be described, with reference to FIGS. 45A to 45G.

Figure 45A:
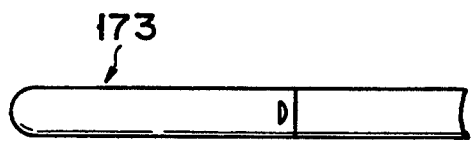
FIGS. 45A to 45F are side views of first to sixth treatment tools which can be attached to the vibration-transmitting member shown in FIG. 44.

FIG. 45A shows a first modification of the treatment tool 173, which is a scoop for separating a tissue from others, without cutting the tissue.

Figure 45B:
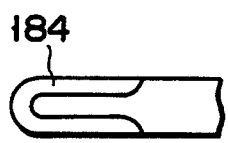

FIG. 45B illustrates a second modification of the tool 173, which is a doubled-edged knife having a blade 184 extending both sides and the tip. With this tool the surgeon can cut an affected tissue from the normal ones.

Figure 45C:
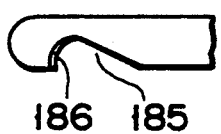

FIG. 45C shows a third modification of the tool 173, which has a U-notch 185 in one side. A blade 186 is formed at the front-end portion of the U-notch 185. An another blade can also be formed at the tip end of the tool. With this tool, the surgeon can easily hitch an affected tissue and cut it away from the normal ones.

Figure 45D:
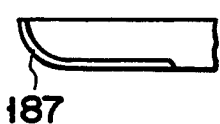

FIG. 45D shows a fourth modification of the tool 173, which is more slender than the tool 173. This treatment tool has a blade 187 at the tip, which can cut tissues well.

Figure 45E:

FIG. 45E illustrates a fifth modification of the treatment tool 173, which has a concave tip 188 with a blade 189. This tool enables the surgeon to hold an affected tissue and cut it by pressing it with the blade 189.

Figure 45F:
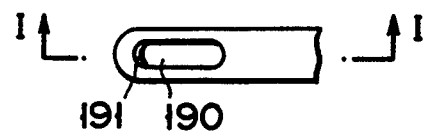
Figure 45G:
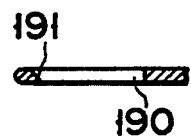
FIG. 45G is a sectional view of the sixth tool, taken along line I—I in FIG. 45F.

FIGS. 45F and 45G shows the sixth modification of the treatment tool 173, which has a through hole 190 and a blade 191 formed at the front end of the hole 190. With this tool, the surgeon can easily cut a projecting tissue.

Four more modifications of the treatment tool 173 will be described, with reference to FIGS. 46A to 46H. Each of these tools has a sharp blade portion 192 and a dull blade portion 193. The sharp blade portion 192 is used to incise tissues. The dull blade portion 193 is used for peeling an affected tissue from normal ones, without cutting the affected tissue. Once attached to the vibration-transmitting member 4, the tool can be used to perform two different types of surgical operations. The use of the two-purpose tool saves the surgeon time for replacing one single-purpose tool with another single-purpose tool. Therefore, the treatment tools shown in FIGS. 46A to 46H help to enhance the efficiency of surgical operations.

As in the fourth embodiment of the invention, each of the treatment tools shown in FIGS. 45A to 45G and FIGS. 46A to 46H can be formed of a shaft and a knife. In this case, the knife can be removably attached to the shaft. Further, a high-frequency power supply can be connected to the treatment tool, in which case the surgeon can use the tool as an electric knife, to cut an affected tissue easily, without causing bleeding.

FIGS. 47 and 48 illustrate the hand piece 1 used in an ultrasonic treatment apparatus according to a fifth embodiment of the present invention. As FIG. 47 shows, the hand piece 1 comprises a Langevin-type ultrasonic oscillator 2 located within an outer cover 69, and a horn 3 integrally connected to the distal end of the oscillator 2, for amplifying the vibration of the oscillator 2. The Langevin-type oscillator 2 comprises piezoelectric elements 65 and electrodes 67, which are alternately arranged. The elements 65 and the electrodes 67 are clamped between the horn 3 and a metal block 64. A flange 3a is integrally formed with the circumference of the horn 3, and located near a node of the ultrasonic vibration of the oscillator 2.

The Langevin-type ultrasonic oscillator 2 is held within an inner cover 195 in the form of a hollow cylinder. The horn 3 has its flange 3a secured to the distal end of the inner cover 195. More precisely, the inner cover 195 has, at its distal end, a flange 195a projecting inwards, and this flange 195a abuts on the flange 3a of the horn 3. A fastening ring 196 is fitted, in screw engagement. in the distal-end portion of the inner cover 195, thus fastening the flanges 3a and 195a together. Hence, the Langevin-type oscillator 2 is held in place within the inner cover 195.

A hollow bolt 66 extends though an axial hole made in the oscillator 2 and horn 3 and protrudes from the proximal end of the oscillator 2. The proximal end of the bolt 66 is connected, in watertight fashion, to a suction port 150 which passes through, and is secured to, the rear wall of the inner cover 195. The hollow bolt 66 define a suction path (not shown) which extends through the oscillator 2 and the horn 3. A suction tube (not shown, either) is connected to the port 150.

The inner cover 195 containing the oscillator 2 is rotatably fitted in a space 197 within the outer cover 69. Two O-rings 198 are mounted on the inner cover 195, sealing the gap between the outer cover 69 and the inner cover 195. These O-rings 198 generate friction between the outer cover 69 and the inner cover 195, such that the inner cover 195 cannot be rotated with a relatively small force.

The electrodes 67 of the ultrasonic oscillator 2 are connected to a power supply (not shown) by the lead wires 152a of a power-supply cord 152 which passes through the rear wall of the inner cover 195.

As is evident from FIGS. 47 and 48, the outer cover 69 has a bulging portion, in which a liquid-supplying path 199. The bulging portion serves as grip portion of the hand piece 1. The liquid-supplying path 199 communicates, at one end, with the distal opening 199a of the outer cover 69 and, at the other end, with a tube connector 200 which passes through the rear wall of the outer cover 69. A liquid-supplying tube (not shown) is connected to the connector 200.

A vibration-transmitting member 4 (i.e., a probe) is connected to the distal end of the horn 3. More precisely, the member 4 has a threaded proximal end, which is set in screw engagement with the distal end of the horn 3. A tool 173 is integrally formed with the tip of the vibration-transmitting member 4. The tool 173 is a blade whose shape is asymmetrical with respect to the axis of the vibration-transmitting member 4. The member 4 has an axial through hole (not shown) which communicates with the suction path formed in the oscillator 2 and the horn 3. The distal end of this axial through hole opens at the tool 173.

Even after the vibration-transmitting member 4 has been partly inserted into the distal-end portion of the horn 3, the inner cover 195 can be rotated, with a relatively large force, with respect to the outer cover 69, thereby to rotate the vibration-transmitting member 4 with respect to the outer cover 69, i.e., the grip of the hand piece 1. The position of the member 4 with respect to the grip remains unchanged due to the friction the O-rings 198 exert between the covers 69 and 195, unless the surgeon rotates the inner cover 195 with a large force. Hence, the surgeon can turn the tool 173 having a special shape, to any position he or she likes, while gripping the hand piece 1 in the same position. The hand piece 1 shown in FIGS. 47 and 48 has high operating efficiency.

FIG. 49 shows a first modification of the hand piece illustrated in FIGS. 48 and 48. This modification is characterized in four respects. First, a single O-ring 198 is mounted on the distal-end portion of the inner cover 195, sealing the gap between the inner circumference of the outer cover 69 and the outer circumference of the inner cover 195. Second, an annular groove 202 is cut in the outer circumference of the proximal-end portion of the inner cover 195, and a fastening screw 203 passes through the outer cover 69 in screw engagement therewith, and protrude into the annular groove 202. The screw 203 is turned tight, thereby fastening the inner cover 195 to the outer cover 69. Third, as is evident from FIG. 49, a hook-shaped tool 173 is integrally formed with the vibration-transmitting member 4. Fourth, a liquid-supplying path 199, which is formed in. the bulging portion of the outer cover 69 and extends parallel to the axis of the hand piece 1, opens at distal end to the interior of the outer cover 69 and communicates with the space surrounding the horn 3. Except for the four structual features, the hand piece 1 shown in FIG. 49 is identical to the hand piece illustrated in FIGS. 47 and 48.

Figure 50:
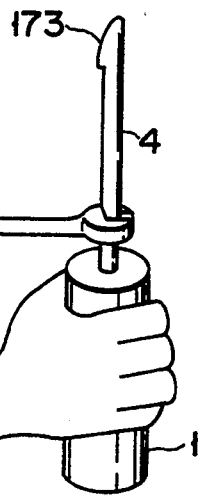
FIG. 50 is a perspective view explaining how to attach a vibration-transmitting member to the hand piece.

In order to connect the vibration-transmitting member 4 to the distal end of the horn 3, the fastening screw 203 is turned, fastening the inner cover 195 to the outer cover 69. Since the inner cover 195 can no longer be rotated or displaced with respect to the outer cover 69, it is easy to connect the member 4 with the horn 3, by turning the former into screw engagement with the latter. Generally, the member 4 is fastened to the horn 3 by turning the member 4 with a spanner, while holding the outer cover 69, as is illustrated in FIG. 50. In the case of the hand piece 1 shown in FIG. 49, the member 4 can be fitted into screw engagement with the horn 3, merely by turning the member 4 by hand.

In addition, once the fastening screw 203 is loosened in the annular groove 202, the inner cover 195 can be rotated with respect to the outer cover 69. This helps to increase the operating efficiency of the hand piece 1.

Figure 51:
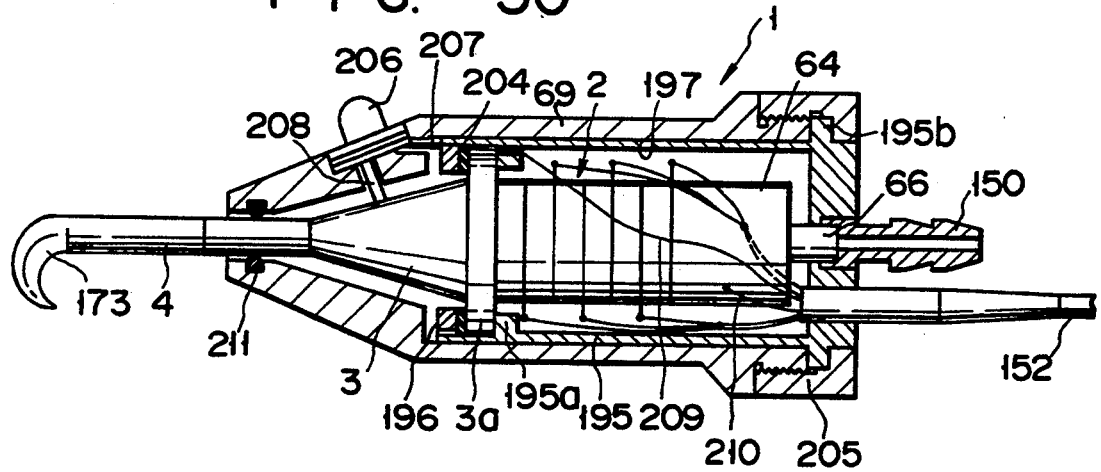
FIGS. 51 and 52 are longitudinal sectional view and enlarged partial view showing a second modification of the hand piece illustrated in FIGS. 48A and 48B.
Figure 52:
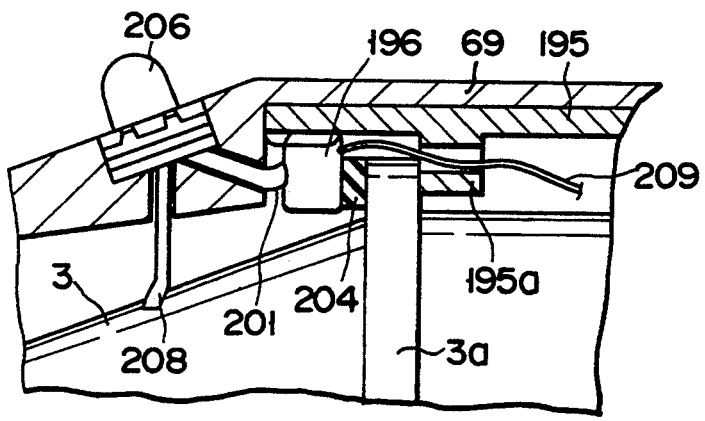

FIGS. 51 and 52 illustrate a second modification of the hand piece illustrated in FIGS. 47 and 48.

The second modification is different from the hand piece shown in FIGS. 47 and 48 in four respects. First, an electrically insulative member 204 is interposed between the flange 3a of the horn 3 and the flange 195a of the inner cover 195. Second, a flange 195b is integrally formed with the proximal end of the inner cover 195, and a fastening ring 205 is connected, in screw engagement, to the proximal end of the outer cover 69, thus abutting the flange 195b and securing the inner cover 195 to the outer cover 69. Third, an electric switch 206 is amounted on the distal-end portion of the outer cover 69, for turning on and off the ultrasonic oscillator 2 held within the inner cover 195. Fourth, an O-ring 211 is fitted in an annular groove cut in the inner circumference of the distal-end portion of the outer cover 69, sealing the gap between the outer cover 69 and the vibration-transmitting member 4.

The electrically insulative member 204 is made of elastic material such as rubber and electrically isolates the horn 3 from the fastening ring 196 which is made of metal. The fastening ring 205 can be turned until it is removed from the outer cover 69, releasing the flange 195b of the inner cover 195. Once the ring 205 is removed from the cover 69, the inner cover 195 can be pulled out of the outer cover 69.

As is shown in FIG. 52, the electric switch 206 has two brushes 207 and 208, which function as anode and cathode, respectively. The first brush 207 contacts with the fastening ring 196, whereas the second brush 208 contacts the horn 3. A first lead wire 209 is connected to the fastening ring 196 which contacts the first brush 207. The horn 3, which is made of metal, is electrically connected to the metal block 64 by the hollow bolt 66. A second lead wire 210 is connected, at one end, to the second brush 207 and, at the other end, to the metal block 64. The lead wires 209 and 210, either coated with an insulation layer, are bundled together and combined with the wires forming the power-supply cord 152.

The same components as those of the hand piece shown in FIGS. 47 and 48 are denoted at the same numerals in FIGS. 51 and 52, and are not described in detail.

In order to connect the vibration-transmitting member 4 to the distal end of the horn 3, the fastening ring 205 is turned and connected to the outer cover 69, in screw engagement therewith, thereby fastening the inner cover 195 to the outer cover 69. Once the inner cover 195 is thus fastened to the outer cover 69, it is easy to attach the member 4 to the horn 3.

If the fastening ring 205 is turned loose, the inner cover 195 can then be rotated with respect to the outer cover 69. Hence, the member 3 can be rotated to any desired position with respect to the outer cover 69 which functions as grip. After rotating the member 3 to the desired position, the surgeon may turn the ring 205 tight, thereby setting the member 3 in that position. This helps to enhance the operating efficiency of the hand piece 1, despite that the tool 173 integrally formed with the member 4 has a special shape.

In whichever direction the inner cover 195 is rotated through whatever angle with respect to the outer cover 69, the first brush 207 and the second brush 208 remain in contact with the fastening ring 196 and the horn 3, respectively, thus maintaining the electrical connection between the switch 206 and the power supply (not shown). When the inner cover 195 is rotated, the lead wires 209 and 210 also rotate in the same direction, and never entangle with each other. The system for connecting the switch 206 to the power supply is relatively simple and small, and the hand piece 1 is, therefore, relatively small.

Figure 53:
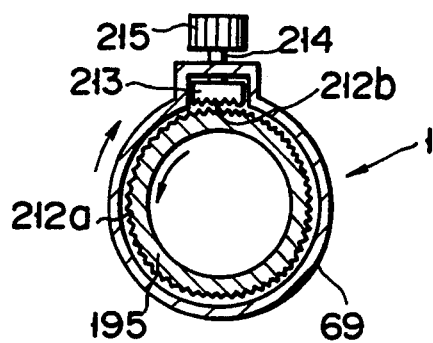
FIG. 53 is a cross-sectional view of a third modification of the hand piece shown in FIGS. 48A and 48B.

FIG. 53 illustrates a third modification of the hand piece shown in FIGS. 47 and 48.

The third modified hand piece 1 is characterized by holding means which is designed to hold the inner cover 195 at a desired position with respect to the outer cover 69. The holding means comprises a plurality of parallel grooves 212a made in the outer circumference of the inner cover 195, a stopper 213, a screw 214, and a dial 215. The stopper 213 is located in a bulging portion of the outer cover 69 and has teeth 212b engageable with the grooves 212a. The screw 214 passes through a hole made in the the bulging portion and put in screw engagement therewith. The screw 214 is connected, at the lower end, with the stopper 213 and, at the top end, to the dial 215.

When the dial 215 is turned in one direction, the screw 214 moves downwards, and so does the stopper 213. When the teeth 212b of the stopper 213 go into engagement within the grooves 212a of the inner cover 195, the stopper 213 holds the inner cover 195, which can no longer rotate with respect to the outer cover 69.

Conversely, when the dial 215 is turned in the opposite direction, the screw 214 moves upwards, and so does the stopper 213. When the teeth 212b of the stopper 213 come out of engagement with the grooves 212a, the inner cover 195 can be rotated with respect to the outer cover 69. The inner cover 195 is rotated such that the vibration-transmitting member 4 assume a desired position with respect to the outer cover 69 which functions as grip.

Thereafter, the dial is turned until the teeth 212b of the stopper 213 engage with the grooves 212a of the inner cover 195, thereby holding the inner cover 195 with respect to the outer cover 69. This helps to enhance the operating efficiency of the hand piece 1, despite that the tool 173 integrally formed with the member 4 has a special shape.

Figure 54:
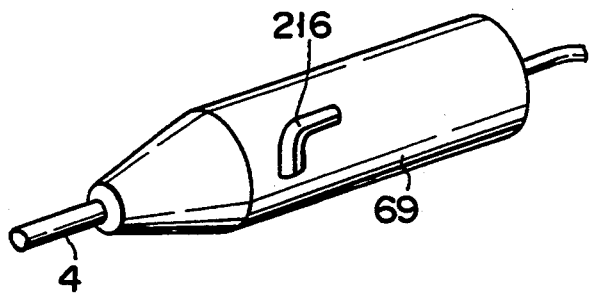
FIGS. 54 to 56 are perspective views of three other modifications of the hand piece shown in FIGS. 48A and 48B.
Figure 55:
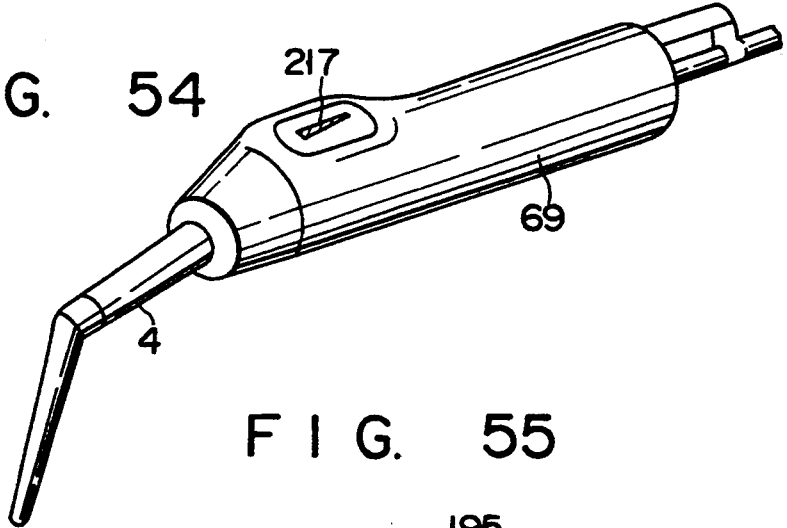
Figure 56:
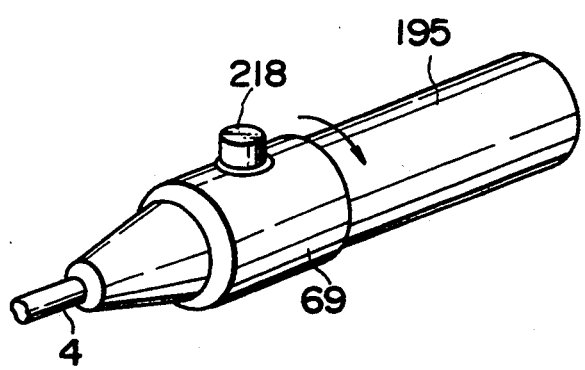
Figure 68:
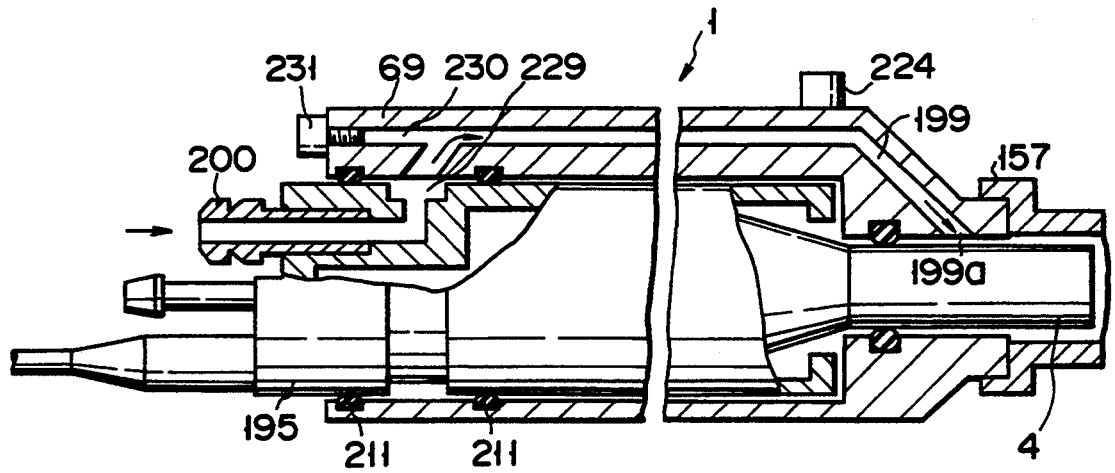
FIG. 68 is a sectional view schematically showing a first modification of the hand piece shown in FIG. 64.

FIGS. 54 to 56 illustrates three modifications of the hand piece 1, each comprising an outer cover 69 having a specific shape.

The modified hand piece shown in FIG. 54 has a finger rest 216 protruding from the outer circumference of the outer cover 69.

The modified hand piece illustrated in FIG. 55 has an elongated leak hole 217 made in the outer cover 69. The hole 217 is partly covered by a finger, such that the negative pressure within the suction path of the hand piece is adjusted in accordance with the opening of the leak hole 217.

The modified hand piece shown in FIG. 56 is characterized in that the outer cover 69 surround only part of the inner cover 195, not covering the entire inner cover 195, and that the outer cover 69 has a switch 218.

In the hand pieces shown in FIGS. 54, 55, and 56, the outer cover 69 may have a cap to which a liquid-supplying tube is connected as in the fifth embodiment illustrated in FIGS. 47 and 48. If this is the case, the cap can be rotated with respect to the inner cover 195.

FIGS. 57 to 63 illustrate various types of electrodes 67 which can be incorporated in the ultrasonic oscillator 2, and to which lead wires 152a are connected to the piezoelectric elements, not by soldering but by mechanical means.

Since these electrodes 67 are firmly held to the piezoelectric elements, reliable connection is maintained unlike in the case where they are soldered to the piezoelectric elements. Since the electrodes 67 are not connected to the elements, not by soldering, the piezoelectric elements are not thermally influenced at all. In addition, for the same reason, the electrodes 67 can be smaller than in the case they are soldered to the piezoelectric elements.

The electrode 67 shown in FIGS. 57 and 58 has a cross-shaped projection 219. As FIG. 58 shows, the projection 219 is bent, extending parallel to a lead wire 152a. The horizontal arms 219a of the cross-shaped projection 219 are bent around and clamp an exposed end of the lead wire 152a.

The electrode 67 shown in FIGS. 59 and 60 has a straight projection 220. As FIG. 60 shows, this projection 220 is bent around an exposed end of a lead wire 152a, thus clamping the tip of the wire 152a. Obviously, it is easier to manufacture this electrode 67 than the electrode illustrated in FIGS. 57 and 58.

The electrode 67 shown in FIGS. 61, 62 an 63 has a short projection 221. A fastening member 222 made of metal, best shown in FIG. 63, is prepared. The member 222 has a bent portion 222a at one end, and a cross-shaped portion 222b at the other end. The bent portion 222a is placed around the short projection 221 and pressed, thus clamping the projection 221. The arms of the cross-shaped portion 222b are bent around and clamp an exposed end of a lead wire 152a. No part of the electrode 67 is bent, the electrode 67 remains strong mechanically.

FIGS. 64 to 67 illustrate the hand piece incorporated in an ultrasonic treatment apparatus according to a sixth embodiment of the invention.

As is shown in FIG. 64, this hand piece 1 comprises an ultrasonic oscillator 2, a horn 3 connected to the distal end of the oscillator 2, and a vibration-transmitting member 4 connected to the distal end of the horn 3. Both the oscillator 2 and the horn 3 are located within an inner cover 195, which in turn is provided within an outer cover 69. The outer cover 69 can be rotated with respect to the inner cover 195, and thus functions as a rotatable grip. A hollow-cylindrical sheath 157 is connected to the distal end of the outer cover 69. The vibration-transmitting member 4 extends through this sheath 157, defining an annular space 223 between it and the inner circumference of the sheath 157. A hand switch 224 is mounted on the outer circumference of the distal-end portion of the outer cover 69, for turning on and off the ultrasonic oscillator 2.

FIG. 67 schematically shows the wiring system of the hand switch 224. As is evident from this figure, the switch 224 is connected to a pair of outer slip rings 225 by two wires 227a. The slip rings 225 are connected to a pair of inner slip rings 226. The rings 226 are connected to two conductors 227b which are insulated from each other and bound together, forming a power-supply cord 228. The cord 228 extends through the proximal-end portion of the inner cover 195 as is illustrated in FIG. 64, and is connected to a power supply (not shown) provided for the ultrasonic oscillator 2. As is shown in FIG. 65, the inner slip rings 226 are amounted on the inner cover 195, and the outer slip rings 225 surround the inner slip rings, respectively. Either inner slip ring 226 has curving projections 226a set in sliding contact with the inner circumferences of the outer slip rings 225. Hence, however the outer cover 69 is rotated, either inner slip ring 226 remains electrically connected to the associated outer slip ring 225.

The hand piece 1 further comprises a water-supplying system for supplying water to the vibration-transmitting member 4, thereby to cool the member 4. As is shown in FIG. 64, the system comprises a water passage 199 extending through a bulging portion of the outer cover 69. Both ends of the passage 199 incline inwards. The distal end 199a of the passage 199 opens at the inner circumference of the distal-end of the outer cover 69, whereas the proximal end of the passage 199 opens at the inner circumference of the proximal-end portion of the outer cover 69. The distal end of the passage 199 is directed to the vibration-transmitting member 4. The distal end 199a of the passage 199, which functions as water outlet port, be located on the same side as the water passage 199 with respect to the outer cover 69, as is desired in view of the operating efficiency of the hand piece 1.

A water-supplying connector 200 is mounted to the proximal end of the inner cover 195. The connector 200 is connected by a path made in the inner cover 195 to an annular groove 229 cut in the outer circumference of the inner cover 195. The annular groove 229 communicates with the distal end of the water passage 199. Hence, the connector 200 is connected to the water passage 199, no matter how the outer cover 69 is rotated with respect to the inner cover 195. O-rings 211 are mounted on the inner cover 195, sealing the gap between the covers 69 and 195, preventing leakage of water.

FIGS. 68 to 71 illustrate a first modification of the hand piece shown in FIGS. 64 to 67. As can be understood from FIG. 68, this hand piece 1 is characterized by a hole 230 made in the distal-end portion of the outer cover 69. The hole 230 extends from the distal end of the cover 69 to the water passage 199. A closing member 231, e.g. a plug, a cap, or a screw, is set in screw engagement with the distal end of the hole 230. The hole 230 is straight and coaxial with the water passage 199. When the closing member 231 is removed, the hole 230 allows a slender brush (not shown) to have easy access to the interior of the passage 199, making it possible to wash the water passage 199.

Figure 69:
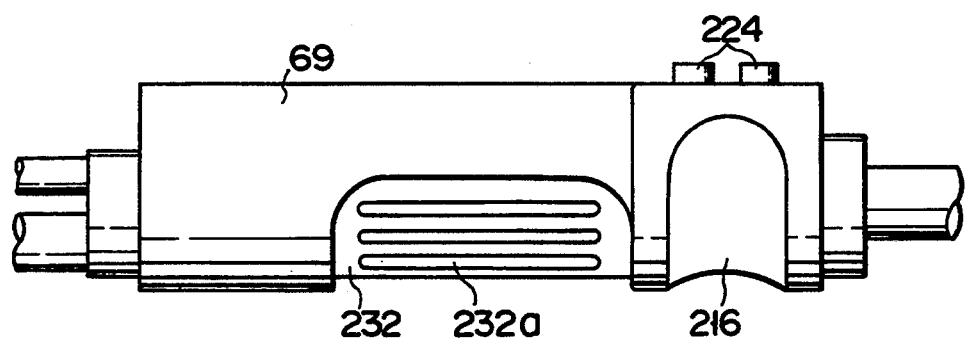
FIGS. 69 to 71 illustrate the other cover of the first modification of the hand piece shown in FIG. 64.
Figure 70:
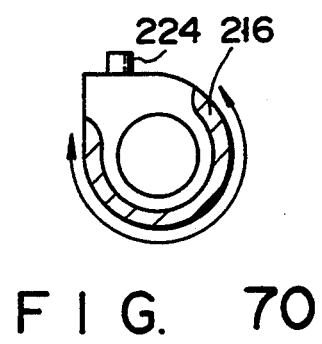
Figure 71:
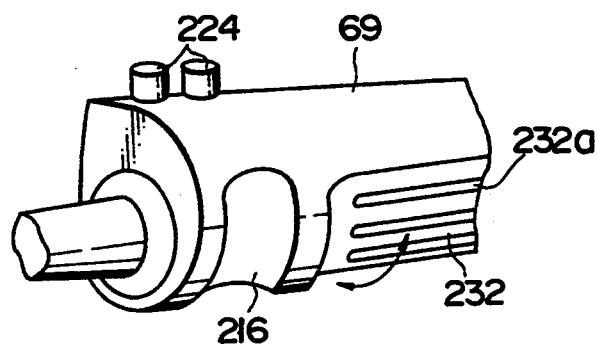

FIGS. 69 and 70 are a side view and a cross sectional view, both showing the hand piece 1. As is evident from these figures, the outer cover 69 has a finger rest 216 formed in the circumference of its distal-end portion and located close to the hand switch 224. Also, the cover 69 has a recess 232 formed in the circumference of its intermediate portion. Parallel grooves 232a are cut in the bottom of the recess 232 for steady gripping of the and piece 1. The outer cover 69 is divided into two parts, at the bordering between the finger rest 216 and the recess 232. These parts can be rotated relative to each other. Alternatively, the outer cover 69 is a single piece, as is illustrated in FIG. 71. In either case, the finger rest 216 and the recess 232 help to achieve steady gripping of the hand piece 1 and easy locating of the hand switch 224.

With the hand piece 1 used in the sixth embodiment (FIGS. 64–67), and the modifications thereof (FIGS. 68–70 and FIG. 71), a surgeon can rotate the outer cover 69 with respect to the inner cover 195, thus setting the hand switch 224 at any desired position. The surgeon can recognize the position of the water passage 199 (unseen from outside) from the position of the hand switch 224, no matter how much he or she has rotated the outer cover 69. This is because the passage 199 and the switch 224, which are formed in and on the bulging portion, respectively, move in the same way as the outer cover 69 is rotated.

Most surgeons hold the hand piece 1 in such a way that the hand switch 224 takes an upper position so that they can push the switch 224 with ease. Hence, the water passage 199 also takes an upper position while the surgeon is holding the hand piece 1 that way. In this condition, the water supplied from an external water source flows through the water-supplying connector 200, the annular groove 229 and the water passage 199. Since the passage 199 is at the upper position, the water flows downward through the inclined distal-end portion of the passage 199 and is forcefully applied onto the vibration-transmitting member 4 from the distal end of the passage 199. Then, the water flows fast to the distal end of the member 4 through the annular space 223 formed between the member 4 and the inner circumference of the sheath 157, efficiently cooling the vibration-transmitting member 4.

Since both the water passage 199 and the hand switch 224 take upper positions in most cases while the hand piece 1 is used, the switch 224 can easily be operated, and the member 4 can be water-cooled with high efficiency.

FIGS. 72 and 73 illustrate a second modification of the hand piece 1 shown in FIGS. 64 to 67 which is incorporated in the sixth embodiment of the invention. This modified hand piece 1 comprises a single cover 69, which is, so to speak, a combination of an outer cover and an inner cover. As is shown in FIG. 72, a hollow-cylindrical cover 232 is rotatably connected to the distal end of the cover 69, surrounding the vibration-transmitting member 4. Further, a hollow-cylindrical sheath 157 is secured to the distal end of the rotatable cover 232, and surrounds the member 4. It is on this sheath 157 that the hand switch 224 is mounted for turning on and off the ultrasonic oscillator 2 located within the cover 69. The switch 224 is electrically connected to a power supply (not shown) by means of such slip rings as are used in the hand piece shown in FIG. 67. Alternatively, the switch 224 can be connected to the power supply by any other means that seems suitable.

As is shown in FIGS. 72 and 73, the hand piece 1 has a water-supplying system for supplying water to the vibration-transmitting member 4, thereby to cool the member 4. This system comprises a water-supplying connector 200 which is mounted to the rotatable cover 232, located near the close to the hand switch 224, and extending into the interior of the cover 232 in the radial direction thereof. The connector 200 has an axial through hole which junctions as water passage 199 and opens, at its distal end 199a, to the interior of the cover 232.

To use the hand piece 1 shown in FIG. 72, the surgeon or his or her assistant connects a hose 16, at one end, to that end of the connector 200 which protrudes from the outer circumference of the rotatable cover 232, and at the other end, to a water source (not shown), as is illustrated in FIG. 73. Then, the surgeon holds the hand piece 1, rotating the cover 232 and placing the switch 224 at an upper position so that he or she can easily push the switch 224. The connector 200, located near the switch 224, is automatically placed at the upper position, too. Water is then supplied from the water source; it flows through the hose 16 into the connector 200. Since the passage 199 extends downwards, the water flows through the passage 199 downward onto the vibration-transmitting member 4. Then, it flows fast to the distal end of the member 4 through the annular space 223 formed between the member 4 and the inner circumference of the sheath 157, efficiently cooling the vibration-transmitting member 4.

Like the hand piece of FIGS. 64 to 67, the modified hand piece 1 shown in FIGS. 72 and 73 is advantageous in that the switch 224 can easily be operated, and the member 4 can be water-cooled with high efficiency. Also is it advantageous in that the rotatable cover 232 is small, helping to minimize the hand piece 1 as a whole.

FIGS. 74 and 75 illustrate a third modification of the hand piece shown in FIGS. 64 to 67. Like the second modification (FIGS. 72 and 73), the third modified hand piece 1 comprises a single cover 69 which is, so to speak, a combination of an outer cover and an inner cover. The cover 69 is not rotatable, unlike its counterpart used in the second modification. The cover 69 is a hollow cylinder having a large-diameter hole in its distal-end portion. The hand piece 1 has a hollow-cylindrical sheath 157, whose proximal-end portion is is fitted in the large-diameter hole of the cover 69, such that the sheath 157 can rotate with respect to the cover 69. Two O-rings 211 are mounted on the proximal-end portion of the sheath 157, achieving watertight sealing between the cover 69 and the sheath 157. That portion of the sheath 157 which is adjacent to the proximal-end portion is thicker than any other portion. A hand switch 224 is mounted on this thick portion of the sheath 157. The switch 224 is electrically connected to a power supply (not shown) by means of such slip rings as are used in the hand piece shown in FIG. 67. Alternatively, the switch 224 can be connected to the power supply by any other means that seems suitable.

A water-supplying connector 200 is mounted to the cover 69 and communicates with a passage 234 made in the cover 69. The passage 234 opens to an annular groove 199 cut in that outer circumference of the proximal-end portion of the sheath 157. The groove 199 is located between the O rings 211. A radial hole 199a is made in the bottom of the groove 199 and opens to the interior of the sheath 157. This hole 199a is located near the hand switch 224.

To use the hand piece 1 shown in FIGS. 74 and 75, the surgeon rotates the hollow-cylindrical sheath 157, thus placing the hand switch 224 at an upper position so that he or she can easily push the switch 224. The annular groove 199, which is located near the switch 224, is automatically placed at the upper position, too. Water is then supplied from the water source into the cap 200. The water further flows through the passage 234 formed in the cover 69 into the annular groove 199 made in the outer circumference of the sheath 157, and hence flows into the interior of the interior of the sheath 157 through the radial hole 199a is made in the bottom of the groove 199. Since the hole 199a extends downwards, the water flows through the hole 199a downward onto the vibration-transmitting member 4. Then, it flows fast to the distal end of the member 4 through the annular space 223 formed between the member 4 and the inner circumference of the sheath 157, efficiently cooling the vibration-transmitting member 4.

Like the hand piece of FIGS. 64 to 67, the third modified hand piece 1 shown in FIGS. 74 and 75 is advantageous in that the switch 224 can easily be operated, and the member 4 can be water-cooled with high efficiency.

In addition, since the water-supplying cap 200 is connected to the cover 69 and positioned remote from the hand switch 224, it does not hinder the positioning of the hand switch 224.

Figure 76:
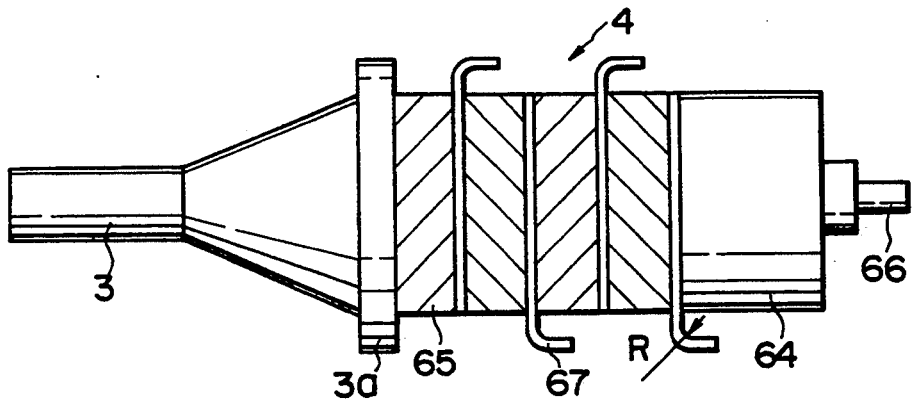
FIGS. 76 to 80 illustrate others modifications of the hand piece.

FIG. 76 shows an ultrasonic oscillator 4 which can be incorporated in the hand piece 1 of any embodiment described above. This oscillator 4 comprises four piezoelectric elements 65 and three electrodes 67—all clamped between a flange 3a of a horn 3 and a metal block 64. The electrodes 67 are interposed among the piezoelectric elements 65. The horn 3, the elements 144, electrodes 145, and the metal block 64 are aligned coaxially and have concentric holes. These holes form a passage. A bolt 66 having an axial through hole extends through this passage. The distal end of the bolt 147 is fastened to the horn 3. The metal block 64, which functions as a nut, is mounted on the proximal end of the bolt 66, so that the elements 144 and the electrodes 145 are firmly fastened together between the horn 3 and the block 64.

Each of the electrodes 67 has a projection which is bent and curved with a curvature R. Hence, the impedance of the ultrasonic oscillator 4 is lower than otherwise, and a relatively low voltage is sufficient for driving the oscillator 4. Applied with a low voltage only, the oscillator 4 neither is liable to dielectric breakdown nor has a great leakage current. The ultrasonic oscillator 4 is, therefore, safe for both the surgeon and the patient.

FIGS. 77 to 80 illustrate other modifications of the hand piece 1.

Figure 77:
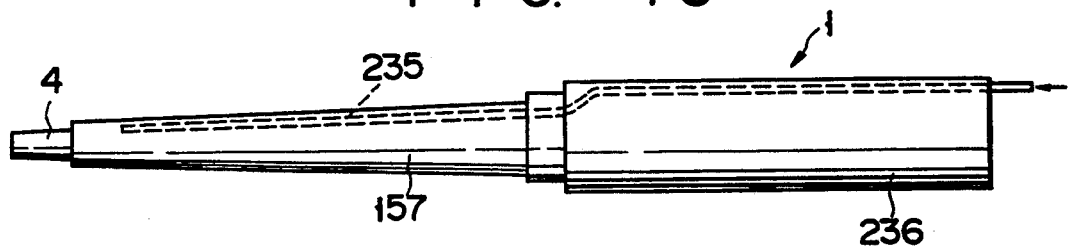

The hand piece 1 shown in FIG. 77 has no members which may limits the view field. A water-supplying tube 236 is not located outside a main body 236 or a hollow-cylindrical sheath 157, but within the main body 236 and the sheath 157. More specifically, the tube 236 extends parallel to the axis of the main body 236, through a gap between a probe 4 (i.e., a vibration-transmitting member) and the hollow-cylindrical sheath 157. The water-supplying pipe 235 does not protrude from the distal end of the sheath 157.

Figure 78:
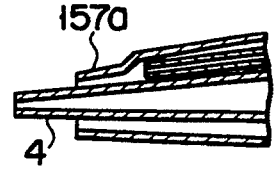

The hand piece 1 illustrated in FIG. 78 is identical to the hand piece shown in FIG. 77, except that the hollow-cylindrical sheath 157 has a thin portion 157a at the distal end.

Both hand pieces of FIGS. 77 and 78 provide surgeons with a sufficient view field since the water-supplying pipe 235 is located within the sheath 157, and no members are located outside the main body 236 or the sheath 157. In addition, the surgeon can easily insert the sheath 157 into a body cavity since the distal-end portion of the sheath 157 is not only thin but tapered toward its tip.

Figure 79:
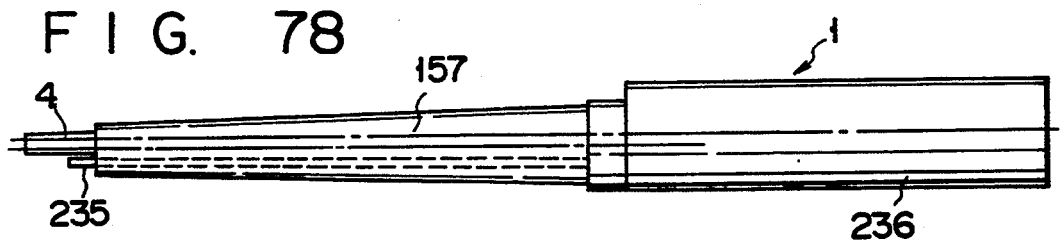
Figure 80:
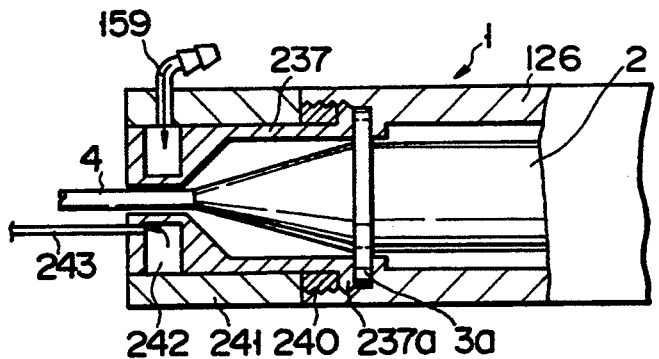

The hand piece 1 shown in FIG. 79 is identical to the hand pieces illustrated in FIGS. 77 and 78, except for two respect only. First, the water-supplying pipe 235 protrudes from the distal end of the hollow-cylindrical sheath 157. Second, the probe 4 is positioned with its axis not aligned with that of the hollow-cylindrical sheath 157. Hence, the distal end of the sheath 157 can have a diameter slightly greater than the sum of the diameters of the probe 4 and the pipe 235. The hand piece 1 shown in FIG. 80 is characterized in that a manifold 237 can easily be attached to and detached from a casing 126 containing an ultrasonic oscillator 2. A stepped portion is formed in the inner circumference of the casing 126. A flange 3a abuts on this stepped portion, and the manifold 237 is inserted in the casing 126, with its flange 237a put in contact with the flange 3a. A nut 240 is set in screw engagement with the female screw cut in the inner circumference of the casing 126, whereby the flange 3a and the proximal end of the manifold 237 are fitted and fixed within the casing 126. A cover 241 is mounted on the distal-end portion of the manifold 237. A water-supplying cap 159 is connected to the cover 241. An annular groove 242 is made in the outer circumference of the manifold 237. The groove 242 communicates with the cap 159 through a hole made in the cover 241. A water-supplying tube 243 is connected, at its proximal end, to the distal end of the manifold 237 and communicates with the annular groove 242. The distal end of the tube 243 is located at the distal end of a hollow-cylindrical sheath (not shown) connected to the cover 241. Hence, water can be supplied to the distal end of the sheath through the cap 159, the annular groove 242, and the tube 243.

Since the water-supplying tube 243 is located below the probe 4, the manifold 237 need not be rotated to have a specific position with respect to the casing 126 even if the oscillator 2, the manifold 237, and the sheath are not coaxial with the casing 126. In other words, the hand piece 1 shown in FIG. 80 can easily be assembled.

FIGS. 81 and 82 illustrate a hand piece which is identical to the hand piece of FIG. 80, except that the water-supplying pipe 235 can be detached from the manifold 237.

The hand piece 1 shown in FIG. 81 is similar to the hand piece of FIG. 77 in that the water-supplying tube 243 extends from the main body 236, passing through the gap between the probe 4 and the hollow-cylindrical sheath 157. The water-supplying tube 243 is attached to the manifold 237 as is shown in FIG. 82. More precisely, an elastic cylinder 244 formed of O-rings is fitted in a hole made in the distal end of the manifold 237. The proximal-end portion of the tube 243 is inserted in the elastic cylinder 244. Due to the spring force of the elastic cylinder 244, the tube 243 is held in watertight fashion.

The water-supplying tube 243 can be removably connected to the manifold 237 in another way, as is illustrated in FIG. 83. To be more specific, a joint tube 237a is fitted in a hole made in the distal end of the manifold 237, and the tube 243 is removably connected to the joint tube 237a. The proximal end 243a of the water-supplying tube 243 can be sharply tapered as is illustrated in FIG. 84. Alternatively, the proximal-end portion 243b of the tube 243 can be gently tapered as is shown in FIG. 85. In either case, the end of the water-supplying tube 243 is gradually thinner toward the manifold 237, and the tube 243 can easily be connected to, and disconnected from, the manifold 237. Hence, the surgeon, or his or her assistant can replace the tube 243 with a new one quite easily, whenever necessary.

FIGS. 86 and FIGS. 87A and 87B illustrate a hand piece for use in an ultrasonic treatment apparatus according to a seventh embodiment of the present invention.

As can be understood from FIGS. 86 and 87A, the flange 3a integrally formed with the horn 3 of an ultrasonic oscillator 2 has two notches 246 made in its circumference and opposing diametrically. A stop ring 247 is mounted on the circumference of the flange 3a. The stop ring 247 has two projections 248 protruding from its inner circumference and fitted in the notches 246 of the flange 3a. The ring 247 also has two arcuate projections 249 extending from the proximal end of the ring 247, opposing diametrically with each other, and located at angular interval of 90° with respect to the projections 248. These arcuate projections 249 are fitted in the two gaps 251 defined by a pair of arcuate projections 250 formed on the inner circumference of the distal-end portion of a cover 69, with two arcuate rubber members 252 clamped between the are mounted on the stop ring 247 and the arcuate projections 250. A fastening ring 254 is fitted in the distal end of the cover 69, in screw engagement, with a rubber ring 253 sandwiched between the stop ring 247 and the fastening ring 254. Thus, the flange 3a is secured to the cover 69 and supported by the arcuate rubber members 252 and the rubber ring 253.

An ultrasonic oscillator 2 is incorporated into the cover 69 as will be explained as follows. First, the arcuate rubber members 252 are placed on the arcuate projections 250. Next, the stop ring 247 is fitted on the flange 3a, with the projections 248 inserted in the notches 246 of the flange 3a. Then, the ultrasonic oscillator 2 is inserted into the cover 69 from the distal end thereof, until the projections 249 of the stop ring 247 are fitted in the two gaps 251 defined by the arcuate projections 250. Hence, the oscillator 2 can no longer rotate with respect to the cover 69. The rubber ring 253 is inserted into the cover 69 and placed on the front of the stop ring 247. The fastening ring 254 is fitted in the distal end of the cover 69, in screw engagement therewith, thereby clamping the arcuate rubber members 252 between the arcuate projections 250 and the flange 3a, and the rubber ring 253 between the flange 3a and the fastening ring 254. As a result, the ultrasonic oscillator 2 is held firmly within the cover 69.

The ultrasonic oscillator 2 can move back and forth, though a little, because of the elasticity of the rubber members 252 and the rubber ring 253. However, it cannot rotate at all, not only because the projections 248 of the stop ring 247 are fitted in the notches 246 of the flange 3a, but also because the projections 249 are fitted in the gaps 251 defined by the projections 250.

Since the flange 3a of the oscillator 2 is held in the cover 69 by means of the rubber members 252 and the rubber ring 253, no parts of the oscillator 2 contact the cover 69. Hence, the rubber members 252 and the rubber ring 253 absorb, but no more than a fraction of the vibration of the oscillator 2, far less than the vibration which the cover 69 should absorb if the flange 3a were in contact with the cover 69 which is much more passive than the rubber members 252 and the rubber ring 253. Obviously, the hand piece shown in FIG. 86 has high energy-efficiency. Further, since the ultrasonic oscillator 2 cannot rotate at all with respect to the cover 69, the hand piece is easy to manipulate. Still further, the hand piece can assembled with ease, since the oscillator 2 is held coaxially with the cover 69 in a specific position with respect to the cover 69 by fitting the fastening ring 254 in the distal end of the cover 69, clamping the flange 3a between the rubber members 252 and the rubber ring 253.

Figure 88:
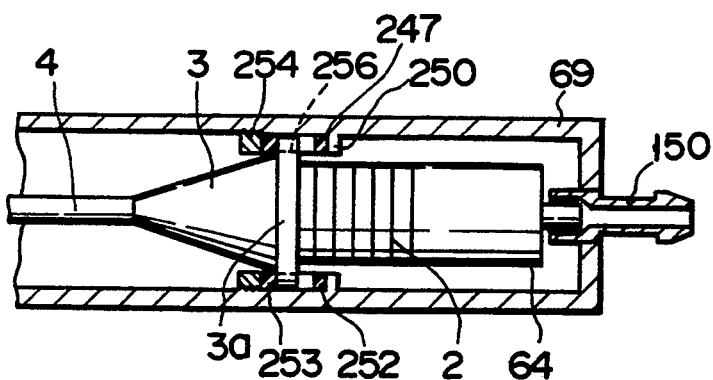
FIG. 88 and FIGS. 89A and 89B illustrate a first modification of the hand piece shown in FIG. 86.
Figure 89A:
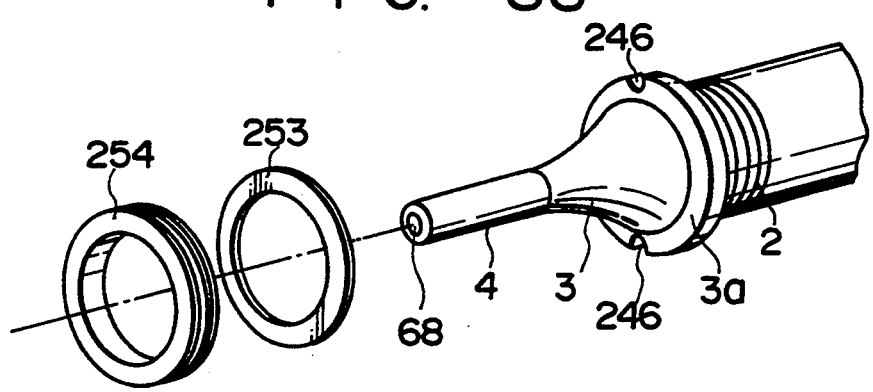
Figure 89B:
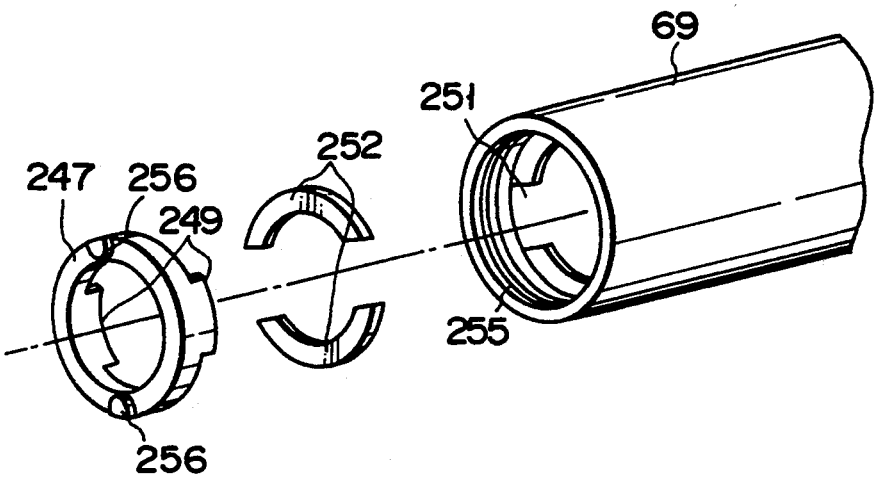

FIGS. 88 and FIGS. 89A and 89B illustrate a first modification of the hand piece shown in FIGS. 86 and FIGS. 87A and 87B. This hand piece is characterized in two respects. First, the stop ring 247 has two projections 256 protruding from the front, which are fitted in the notches 246 of the flange 3a. Second, the stop ring 247 is clamped between the flange 3a and the arcuate the stop ring 247 and the arcuate projections 250. The modified hand piece has the same advantages as the hand piece shown in FIGS. 86 and FIGS. 87A and 87B.

Figure 90:
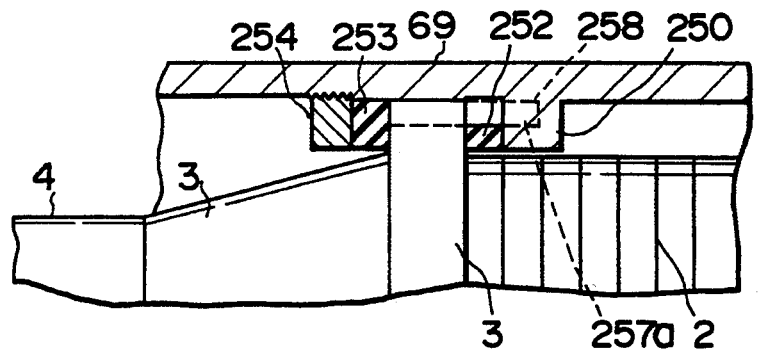
FIG. 90 is a sectional view showing a part of a second modification of the hand piece shown in FIG. 86.

FIG. 90 shows a second modification of the hand piece illustrated in FIGS. 86 and FIGS. 87A and 87B. As can be understood from FIG. 90, this hand piece has two fastening pins 257 (only one shown), instead of a fastening ring. The pins 257 protrude from the rear side of the flange 3a and inserted in two holes 258 (only one shown) made in the arcuate projections 250 of the cover 69, whereby the ultrasonic oscillator 2 is unable to rotate and takes a specific position with respect to the cover 69. The second modified hand piece, too, has the same advantages as the hand piece shown in FIGS. 86 and FIGS. 87A and 87B.

Figure 91A:
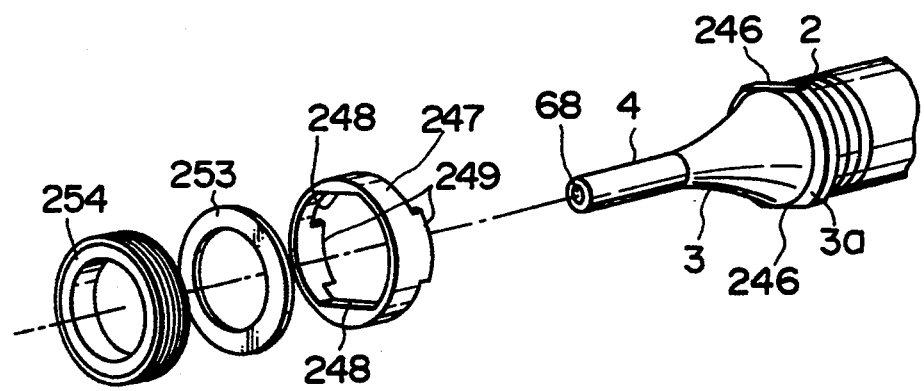
FIGS. 91A and 91B are exploded perspective views of the hand piece shown in FIG. 90.
Figure 91B:
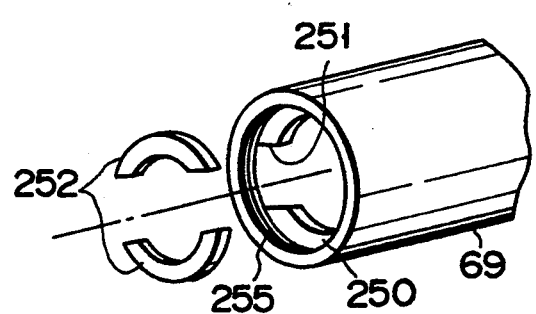

FIGS. 91A and 91B illustrate a third modification of the hand piece shown in FIGS. 86 and FIGS. 87A and 87B. The third modified hand piece is characterized in the two respects. First, the flange 3a integrally formed with the horn 3 has two flat surfaces 246 on the circumference and is smaller than that of the hand piece shown in FIGS. 86 and 87A and 87B, the flat surfaces 246 being located symmetrically with respect to the center of the flange 3a. Second, the stop ring 247 has two thick portions 248 which are located symmetrically with respect to the axis of the ring 247, each thick portion 248 having a flat inner surface contacting the corresponding flat surface 246 of the flange 3a. This modified hand piece not only has the same advantage as the hand piece of FIGS. 86 and FIGS. 87A and 87B, but also is smaller than the hand piece of FIGS. 86 and FIGS. 87A and 87B.

Figure 92:
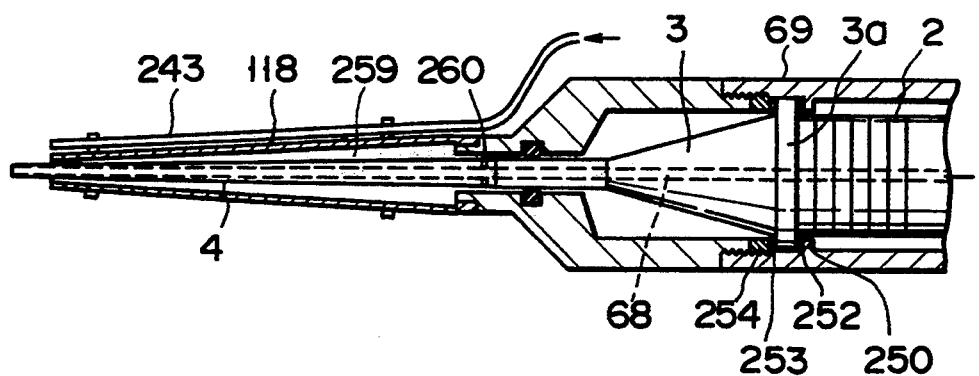
FIG. 92 is a sectional view showing a hand piece designed to supply a perfusion liquid.

FIG. 92 illustrates a hand piece which is designed for use in an ultrasonic treatment apparatus of the present invention and which can supply a perfusion liquid. As this figure shows, the hand piece comprises an ultrasonic oscillator 2, a horn 3 connected to the oscillator 2, and a vibration-transmitting member 4 connected to the horn 3. The hand piece has an axial suction path 68 extends through the oscillator 2, the horn 3, and the member 4. The proximal end of the path 68 is connected to a suction pump (not shown) by a suction tube (not shown, either). When the suction pump is driven, the tissue emulsified by the member 4 or stones broken by the member 4 can be removed from a body cavity through the suction path 68 and the suction tube. The vibration-transmitting member 4 is tapered toward its distal end, and extends through a hollow-cylindrical sheath 118 which is tapered toward its distal end. The annular space 259 between the member 4 and the sheath 118 communicates with a leak hole 260 which is made in the proximal portion of the member 4 and communicates with the suction path 68. A water-supplying tube 243 is arranged outside the sheath 118, extending substantially parallel to the sheath 118 to the distal end of the sheath 118. A perfusion liquid can therefore be supplied to the distal end of the sheath 118 through the tube 243.

When the suction pump is driven, a negative pressure is exerted in the annular space 259 which communicates with the suction path 68 through the leak hole 260. Part of the perfusion liquid, which has been supplied to the distal end of the member 4, is applied to a treatment tool attached to the member 4, thus washing the tool. The liquid used for this washing is removed from the body cavity, together with the incised or emulsified tissue, through the annular space 259. In the meantime, the rest of the perfusion liquid supplied to the distal end of the member 4 is made to flow into, and keeps flowing through, the annular space 259 due to the negative pressure exerted in the space 259. While flowing through the space 259, the liquid cools the vibration-transmitting member 4 undergoing ultrasonic vibration and thus generating heat. Both the incised or emulsified tissue and the perfusion liquid further flow through the leak hole 260 into the suction path 68. If the leak hole 260 is formed at the portion near the loop of the vibration on the vibration-transmitting member 4 where the stress becomes minimum, the member 4 may have a strong strength. With the hand piece shown in FIG. 92, the perfusion liquid can wash the treatment tool and cool the vibration-transmitting member 4, with high efficiency.

Figure 93:
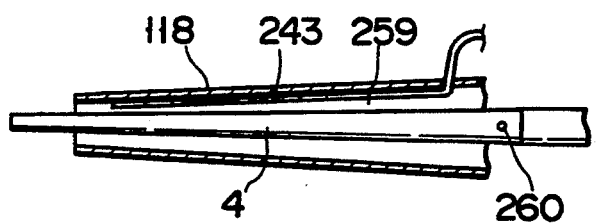
FIG. 93 shows a part of a modification of the hand piece shown in FIG. 92.

FIG. 93 shows a modification of the hand piece shown in FIG. 92. In this modified hand piece, the water-supplying tube 234 is located within the sheath 118, extending through the annular space 259 between the vibration-transmitting member 4 and the hollow-cylindrical sheath 118. Not only can the modified hand piece wash the treatment tool and cool the member 4, as the hand piece shown in FIG. 92, but also can it be manipulated more easily since there are no members protruding from the outer circumference of the hollow-cylindrical sheath 118.

FIG. 94 illustrates a hand piece which can adjust a suction pressure. As this figure shows, a ring 261 is rotatably mounted on a cover 69. A water-supplying tube 243 is connected to the ring 261, for supplying a perfusion liquid into a body cavity. The ring 261 has a pressure-adjusting hole 263 having a thick portion 262 which opens to the atmosphere. The hole 263 is connected by a pressure-adjusting tube 264 to the branch 165 of a suction cap 150 connected to a suction path 68 of an ultrasonic oscillator 2.

When the surgeon closes the thick portion 262 of the pressure-adjusting hole 263, with his or her finger, air supply into the hole 263 is stopped from the atmosphere and the suction force in the hole 263 is increased. More precisely, the smaller the opening of the thick portion 262, the less air flows into the hole 263, and the greater the suction force. Moreover, since the water-supplying tube 243 is connected to the ring 261, and the ring 261 has the pressure-adjusting hole 263, the surgeon can move the tube 243 and the hole 263 to desired positions, merely by rotating the ring 261. As the ring 161 is rotated, the water-supplying tube 243 and the pressure-adjusting tube 264 are moved around the cover 69, together with each other. Hence, the tubes 243 and 264 do not contact or entangle at all.

FIG. 95 shows a modification of the hand piece illustrated in FIG. 94. A rod-shaped member 266 is used in place of the ring 261. The member 166 is located outside the cover 69 and extends parallel to the axis thereof. The member 166 is mounted on the cover 69 and can rotate around the cover 69. The member 266 has a water-supplying hole 267 and a pressure-adjusting hole 271. The water-supplying hole 267 extends along the axis of the member 166. The pressure-adjusting hole 271 also extends along the axis of the member 166. The proximal end of the hole 271 is connected to the branch 270 of a suction tube 13 which communicates with the suction path 68 of the ultrasonic oscillator. The hole 271 has a large-diameter portion 268 at the other end 269.

When the surgeon closes the thick portion 268 of the pressure-adjusting hole 271, with his or her finger, thus stopping air supply into the hole 271 from the atmosphere and increasing the suction force in the suction path 68. More precisely, the smaller the opening of the thick portion 268, the less air flows into the hole 271, and the greater the suction force. Moreover, since both the pressure-adjusting hole 271 and the water-supplying tube 267 are formed in the rod-shaped member 266, the surgeon can move the tube 267 and the hole 271 to desired positions, merely by rotating the rod-shaped member 266. As the member 266 is rotated, the water-supplying hole 267 and the pressure-adjusting hole 271 are moved around the cover 69, together with each other. Hence, the water-supplying path and the pressure-adjusting path do not cross or entangle at all.

FIG. 96 illustrates a hand piece incorporated in an ultrasonic treatment apparatus according to an eighth embodiment of the invention. This hand piece has an ultrasonic oscillator 2 comprising a horn 3, a metal block 64, and piezoelectric elements clamped between the horn 3 and the block 64. The horn 3, the piezoelectric elements, and the metal block 64 are aligned coaxially and have concentric holes. These holes form a passage. A bolt 66 having an axial through hole, or a suction path 68, extends through this passage. The distal end of the bolt 66 is fastened to the horn 3. The metal block 64, which functions as a nut, is mounted on the proximal end of the bolt 66, so that the piezoelectric elements are firmly fastened together between the horn 3 and the block 64. The oscillator 2, thus assembled, is located within a cylindrical cover 69. A suction cap 150 passes into the space 69a between the block 64 and the rear wall of the cover 69, through a hole 273 made in the rear wall of the cover 69, not coaxial with the cover 69. The distal end of the bolt 66 protrudes into the space 69a and inserted in the suction cap 150. Two O-rings 272 are mounted on the distal end of the bolt 66, providing watertight connection of the bolt 66 and the suction cap 150. Hence, the suction path 68 is connected to the cap 150. A suction tube 13 is connected to the proximal end of the suction cap 150. A tube 274 is fitted in a hole made in the rear wall of the cover 69. An electric cord 152 passes through the tube 274 into the cover 69, and is connected to the ultrasonic oscillator 2 for supplying electrical signals thereto.

Since the suction cap 150 is not coaxial with the cover 69, a sufficiently large space is provided for accommodating the electric cord 152, in spite of the relatively small outside diameter of the cover 69. The cover 69 can therefore be smaller than otherwise. In addition, since there are no members protruding from the outer circumference of the cover 69, which serves as a grip, the hand piece is easy to manipulate.

FIG. 97 shows a first modification of the hand piece of FIG. 96. This modified hand piece is characterized in three respects. First, a fastening ring 275 is fitted in a hole made in the rear wall of the cover 69. Second, the suction cap 150 passes and is fitted in the fastening ring 275. Third, a connection tube 276 made of silicone rubber or the like connects the suction cap 150 with the bolt 66 which defines the suction path 68. As can be understood from FIG. 97, the cap 150 and the connection tube 276 constitute a smooth suction path which facilitates the passage of whatever removed from a body cavity. No caps need to be used which are not coaxial with the cover 69. Further, the vibration of the oscillator 2 is not transmitted to the cover 69 because the connection tube 276, made of elastic material, absorbs the vibration of the metal block 64 of the oscillator 2.

Figure 98:
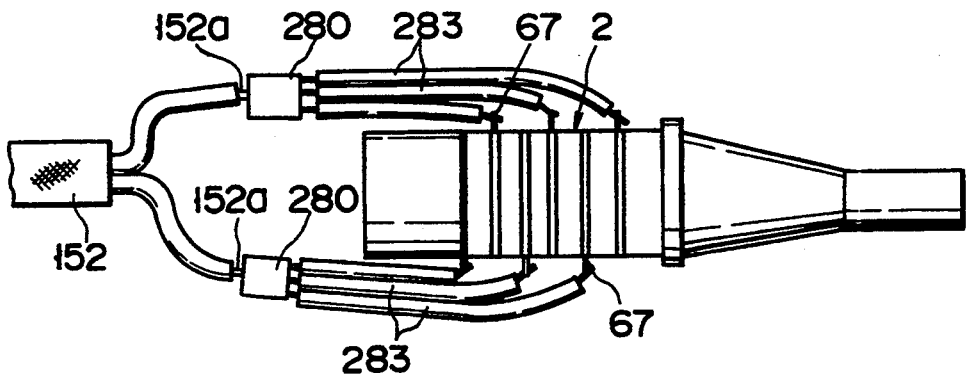
FIGS. 98 and 99 illustrate a hand piece having an improved electrical connector having two connection terminals.
Figure 99:
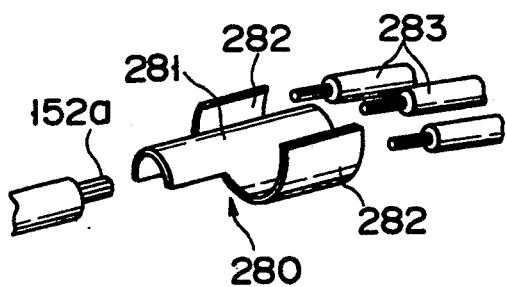

FIGS. 98 and 99 show a hand piece which has an improved connector coupling an electric cord 152 to the the electrodes 67 of an ultrasonic oscillator 2. The connector has two terminals 280. As is shown in FIG. 99, either terminal 280 consists of a long tube half 281 and two short tube halves 282. The short tube halves 232 are integrally formed with the sides of the long tube half 281, so that the terminal 280 has a waving cross section. The wires 152a of the cord 162 and three lead wires 283 are connected to the terminal 280 in the following manner.

First, the wires 152a are placed on one end of the long tube half 281, while the three lead wires 283 are placed on the other end of the half 281 and the short tube halves 282, respectively. Then, the long tube half 281 and the short tube halves 282 are collapsed. As a result of this, the cord 152 is fastened to the first end of the long tube half 281, whereas the three lead wires 283 are fastened to the second end of the tube half 281 and the two short tube halves 282, respectively. This method of connecting the cord 152 to the lead wires 283 is easier than than soldering which has hitherto been employed. Moreover, the connection accomplished by this method is firm and strong, and there is no possibility that the wires 286 are disconnected from the cord 152 despite of the vibration of the ultrasonic oscillator 2.

FIGS. 100 to 105 show a hand piece having an improved wiring system within a hollow-cylindrical cover 69. As is shown in FIG. 100, two circular recesses 284 are formed in the outer circumference of the distal portion of the cover 69, and two switches 286 are set in these recesses 284. These switches 286 are used to turn on and off the ultrasonic oscillator 2 held within the cover 69. As is is shown in FIG. 102, a screw 285 is cut in the circumference of either circular recess 284. As is best shown in FIG. 103, either switch 286 comprises a stationary contact 286a, a movable contact 286b, and a rubber contact 287. The stationary contact 286a is fixed on the bottom of the circular recess 284. The movable contact 286b is connected to the lower end of the rubber contact 287. The rubber contact 287 is made of elastic material such as silicone rubber and has a flange 289 extending sideways from the lower end. An O-ring 290 is integrally formed with the circumference of the flange 289. A holding member 192 is set in the circular recess 284, in screw engagement with the screw 285. The holding member 192 has two bottomed holes 291 in the upper surface, a center hole 293 and an annular groove 194 in the lower surface. The operating portion 288 of the rubber contact 287 passes through the center hole 293, and the O-ring 290 of the rubber contact 287 is fitted in the annular groove 194. Hence, either switch 286, which comprises a relatively small number of components, is connected to the cover 69 in watertight seal.

As is illustrated in FIG. 100, a connector 295 is attached to the rear wall of the cover 69. Lead wires 296 are connected, at one end, to the connector 295. They extend through a guide path 297 made in the circumferential wall 69 of the cover 69. The guide path 297 opens, at one end, to the interior of the cover 69, and communicates, at the other end, with the circular recesses 284 in which the switches 286 are fitted. The lead wires 296 are connected to the connecting terminals 286a of the switches 286.

Since the lead wires 296 pass through the guide path 297 made in the circumferential wall 96a of the cover 69, they are free of the vibration of the ultrasonic oscillator 2 and protected against disconnection. The lead wires 296 are thin, and the guide path 297 is therefore slender, not rendering the circumferential wall 69a thick. Hence, the cover 69, which serves as a grip, has a relatively small diameter and is easy to grip.

Alternatively, the lead wires 296 can be guided through a through hole 299 made in the flange 3a of the horn (not shown) of the oscillator 2, as is illustrated in FIG. 101 and FIG. 104. In this case, the cover 69 can be made thinner. Instead of the through hole 299, a U-notch 300 can be made in the circumference of the flange 3a, as is illustrated in FIG. 105, for guiding the lead wires 296 from the connector 295 to the switches 286. The switches 286 can also be used to turn on and off the power supply unit (not shown) for supplying a high-frequency cauterizing current.

Figure 106:
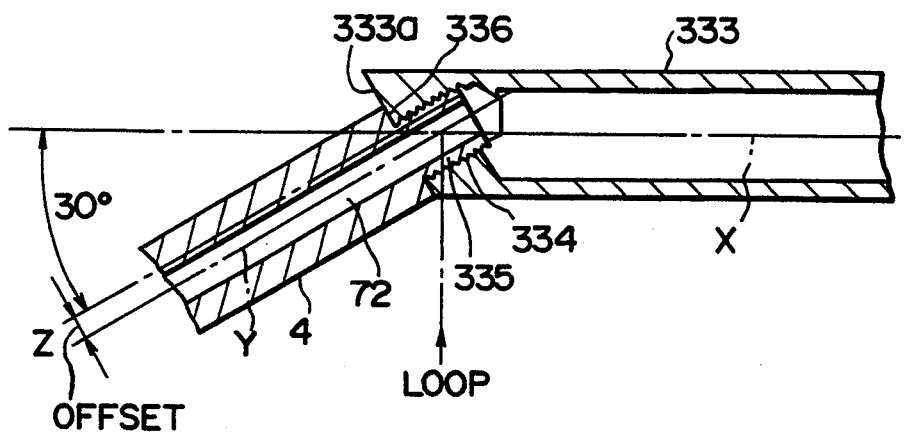
FIG. 106 is a sectional view showing a main part of a hand piece incorporated in an ultrasonic treatment apparatus according to a ninth embodiment of the present invention.

FIG. 106 shows a hand piece incorporated in an ultrasonic treatment apparatus according to a ninth embodiment of the invention. This hand piece is characterized in that the distal-end portion 333 of the horn 3 has an end face inclined at, for example, 60° to the axis X of the horn 3. In the end face 333a, a screw hole 334 is formed which extends at right angles to the end face 333. The axis Y of the screw hole 334 is set off by distance Z from the axis X of the horn 3, and intersects with the axis X of the horn 3. A probe 4 is connected to the distal-end portion 333 of the horn 3, with its proximal end 335 fitted in the screw hole 334 in screw engagement. Since the proximal end 335 is coaxial with the probe 4, the probe 4 is coaxial with the screw hole 334. Hence, the axis Y of the probe 4 crosses the axis X of the horn 3 at a point within the horn 3, where a loop of the ultrasonic vibration exits. It follows that the loop of vibration is located more proximal than the end face 333a of the horn 3.

Since the axis Y of the screw hole 334 is set off below the axis X of the distal-end portion 333 of the horn 3, the screw hole 334 is long enough to hold the probe 4 steadily, despite that the horn 3 is relatively slender. Since the end face 333a is inclined at 60° to the axis X of the horn 3, the probe 4 inclines at 30° to the horn 4, and its axis Y intersects with the axis X of the horn 3 at a point within the horn 3, where a loop of the ultrasonic vibration is located. Hence, the probe 4 can transmits the vibration with high efficiency, though it is inclined at a great angle to the horn 2.

Figure 107:
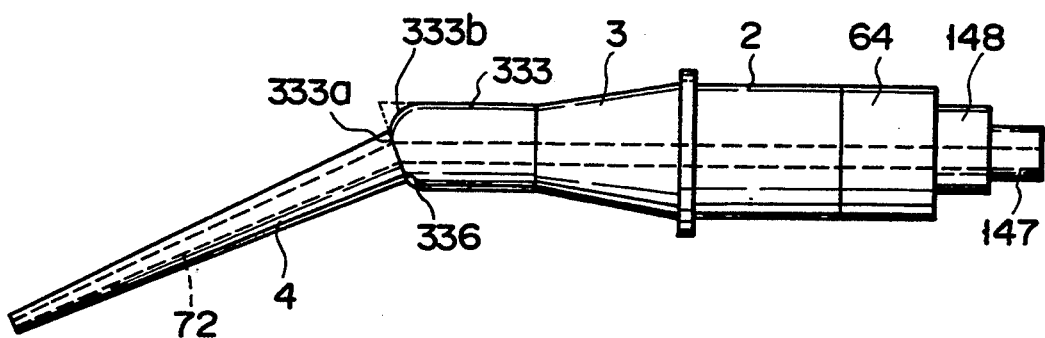

FIGS. 107 and 108 illustrate a first modification of the hand piece shown in FIG. 106. The projecting part of the distal-end portion 333 of the horn 3, which is indicated by the two-dot, one-dash line, is cut away, forming a rounded part 333b. Now that the projecting part has been cut away, the surgeon has a broader view field and can more safely manipulate the hand piece. In addition, since the proximal end of the probe 4 contacts, in its entirely, the end face 333a of the horn 3, the probe 4 can transmits the ultrasonic vibration with high efficiency.

FIG. 109 shows a second modification of the hand piece illustrated in FIG. 106. The projecting part of the distal-end portion 333 of the horn 3, which is indicated by the two-dot, one-dash line, is cut away and machined, forming three rounded parts 333c. Hence, the hand piece has the same advantages as the hand piece of FIGS. 107 and 108. That is, the surgeon has a broader view field and can more safely manipulate the hand piece, and the probe 4 can transmit the ultrasonic vibration with high efficiency.

Figure 110:
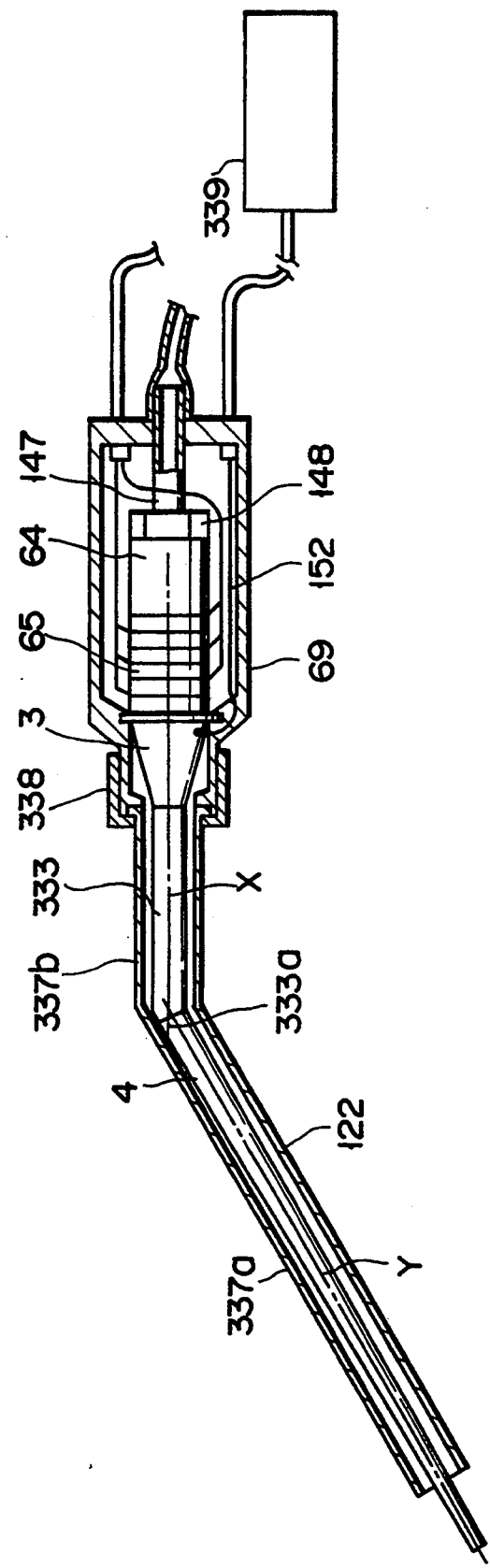
FIG. 110 is a sectional view illustrating a third modification shown in FIG. 106.

FIG. 110 shows a third modification of the hand piece illustrated in FIG. 106. This hand piece is characterized by a hollow-cylindrical cover 69 and a hollow-cylindrical sheath 122. The cover 69 covers piezoelectric elements 65 and a horn 3, except for the distal-end portion of the horn 3. The sheath 122 covers the distal-end portion of the horn 3 and a probe 4, except for the distal-end portion of the probe 4. Both the cover 69 and the sheath 122 are made of electrically insulating material. The sheath 122 is formed of two pipes 337a and 337b which are coupled together, end to end, and inclined to each other. Alternatively, the sheath 122 may be made of flexible material in one body. The sheath 122 is a bent member and removably connected to the cover 69 by means of a fastening ring 338.

A high-frequency power cord 152 extends through the cover 69, having one end connected to the horn 3 and the other end connected to a connector fitted in the rear wall of the cover 69. The connector is connected to a high-frequency power unit 339 provided outside the hand piece. Except for this feature, the third modified hand piece is identical to the hand piece shown in FIG. 106.

In the third modified hand piece, the high-frequency current generated by the power unit 339 is supplied to the horn 3 and the probe 4 through the high-frequency power cord 152. Hence, the distal end of the probe 4 serves as a high-frequency treatment electrode. Although not shown, the hand piece has an electrode. This electrode is connected to the body surface of a patient, so that a high-frequency current flows to it from the distal of the probe 4, thereby coagulating the blood oozing from the tissue being treated within a body cavity, in order to stop bleeding.

The high frequency current flowing through the cord 152, the horn 3 and the probe 4 does not leak to anything other than the affected tissue being treated. This is because the cover 69 covering the piezoelectric elements 65 and part of the horn 3 is made of electrically insulating material, and the sheath 122 covering the probe 4 and the remaining part of the horn 3 is also made of electrically insulating material. Hence, neither the patient nor the surgeon is protected from electric shocks. In view of this, the hand piece shown in FIG. 110 is safe.

FIGS. 111 and 112 illustrates a hand piece for use in an ultrasonic treatment apparatus according to an tenth embodiment of the invention.

As is shown in FIG. 111, the hand piece comprises a grip 10 having a cover 69, an ultrasonic oscillator 2 held within the cover 69, a horn 3 connected connected to the oscillator 2, and a vibration-transmitting member, for example a probe 4, connected to the horn 3. A power-supplying cord 152 is connected to the ultrasonic oscillator 2. The horn 3 amplifies the ultrasonic vibration generated by the oscillator 2, and the amplified vibration is transmitted to the probe 4.

The probe 3 is covered by a hollow-cylindrical sheath 118. The sheath 118 has its proximal end connected to the cover 69 by a connector 341. The sheath 118 is coaxial to the probe 3 and surrounds the probe 3, not contacting the probe 4. The distal-end portion of the probe 4 protrudes from the distal end of the sheath 118.

As is shown in FIG. 112, the annular space between the probe 4 and the sheath 118 forms a path 158 for supplying a liquid such as sterile water or a physiological saline solution from a liquid-supplying cap 159. The cap 159 is connected to a liquid supplying cap 159 by a liquid-supplying tube. The cap 159 is connected to the connector 341.

The probe 4 consists of a metal pipe, the interior of which serves as a suction path 68. The distal-end portion of the probe 4 is tapered. The probe 4 is removably coupled to the distal end of the horn 3, and any probe of a different type can be coupled to the distal end of the horn 3, instead.

The suction path 68 communicates with a suction cap 150 through a suction path 68 formed in the horn 3 and the oscillator 2. The suction cap 150 is connected to a suction pump (not shown) by a suction tube 13. Hence, the suction pump can apply a suction force to the suction path 69 through the suction tube 13.

As is shown in FIG. 112, the sheath 118 is gently tapered toward its distal end. It is made of resin, such as fluoroplastic resin, and is therefore flexible. Its wall thickness is small and uniform.

The hand piece shown in FIGS. 111 and 112 is used in the following manner. First, the probe 4 and the sheath 118 are inserted into a body cavity containing an affected tissue which is to be treated. A liquid, such as sterile water or physiological saline solution, is supplied through the liquid-supplying cap 159, and the liquid-supplying path 158, and is applied onto the affected tissue from the distal end of the sheath 118. The probe 4 is cooled with the liquid, and the affected tissue is cleaned with the liquid. The liquid used in the cavity is drawn through the suction path 69 formed in the probe 4, by virtue of the suction force applied to the suction path 69 from the suction pump (not shown) through suction tube 13 and the suction cap 150.

In the meantime, the ultrasonic vibration of the oscillator 2 is transmitted to the distal end of the probe 4. When the distal end of the probe 4 is brought into contact with the affected tissue, it incises or emulsifies the tissue. The tissue incised or emulsified is removed from the body cavity, along with the used liquid, through the suction path 69, the suction cap 150, and the suction tube 13, by virtue of the suction force generated by the suction pump (not shown).

The hollow-cylindrical sheath 118, which covers the probe 4, is made of a flexible resin. It is gently tapered toward its distal end, and has a small and uniform wall thickness. The sheath 118 can be manufactured by molding, easily and at low cost. Its wall thickness is about 0.2 to 0.4 mm. Since its wall can be formed very thin by molding, the sheath 118 can have a small diameter over its entire length. Hence, the sheath 118 does not hinder the observation of the affected tissue. Moreover, since the sheath 118 is flexible, it can easily be positioned coaxial with the probe 4 during the assembling of the hand piece. In addition, since the sheath 118 is made of fluoroplastic resin, it is heat-resistant and remains intact at 200° or more. Therefore, even if the probe 4 generates an excess of heat while undergoing ultrasonic vibration, the sheath 118 will be neither deformed or damaged, and the surgeon can perform the treatment or operation very safely.

FIG. 113 shows a first modification of the hand piece illustrated in FIGS. 111 and 112. This modified hand piece is characterized by the use of an arcuate probe 4 and an arcuate sheath 118. The sheath 118 surrounds the probe 4, is positioned coaxial therewith, and is bent with the same curvature as the probe 4.

FIG. 114 shows a second modification of the hand piece illustrated in FIGS. 111 and 112. The second modified hand piece is characterized by the use of bent probe 4 and a bent sheath 118. The probe 4 is bent an a predetermined angle, and so is the sheath 118 which surrounds the probe 4 and is positioned coaxial therewith.

In the hand pieces shown in FIGS. 111 and 112, FIG. 113, and FIG. 114, the sheath 118 can be made of transparent material, such as a fluoroplastic resin. If this is the case, the distal end of the probe 4 can be been from outside even if the distal-end portion of the probe 4 is placed behind the sheath 118, thereby enhancing the operating efficiency of the hand piece. The sheath 118 can be made of materials other than fluoroplastic resin. For example, it can be made of silicone resin or nylon, or the like.

Figure 115:
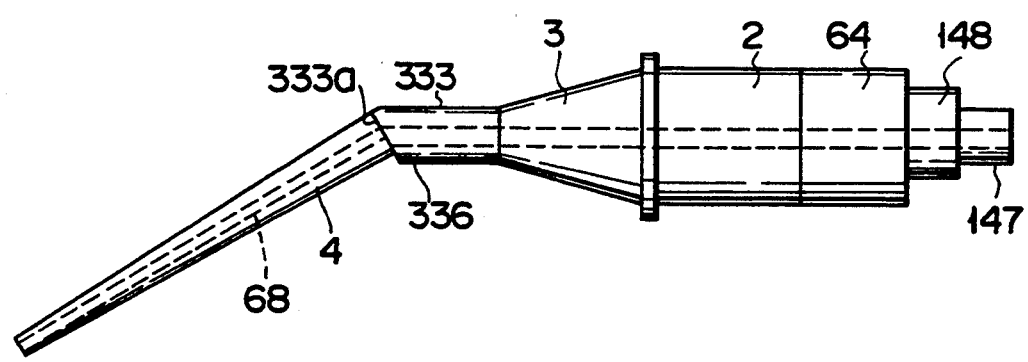

FIGS. 115 to 117 show a hand piece for use in an ultrasonic treatment apparatus according to an eleventh embodiment of the invention.

This hand piece comprises a horn 3 having a hollow-cylindrical distal-end portion 333. The end face 333a of the portion 333 is inclined downward. A probe 4 is connected to the end face 33a, with its distal end set in screw engagement with a screw hole made in the distal end of the horn 3. The probe 4 is inclined to the horn 3. The horn-shaped edge 342 protruding from the end face 33a is cut away, and the end face 333 has a cross section identical to that of the proximal end 336 of the probe 4. In addition, the upper edge of the end face 33a of the distal end portion 333 almost coincides with the upper edge of the proximal end face 336 of the probe 4. The probe 4 is connected to the horn 3, inclined to the axis of the horn 3, and there are no stepped joints between the horn 3 and the probe 4. Since the horn-shaped edge 342 protruding from the end face 33a is cut away, the surgeon has a broader view field and can more safely manipulate the hand piece.

FIG. 118 illustrates a modification of the hand piece shown in FIGS. 115 to 117, wherein the probe 4 is connected to the horn 3 in a different way. The horn-shaped edge 342 is cut slantwise. In other words, the upper edge of the end face 333a of the horn 3 is cut off. The probe 4 is welded to the horn 3, with its end face 336 abutting on the end face 333a of the horn 3. The upper edge of the horn 3 is therefore in the same level as the upper edge of the probe 4. With this modihand piece, too, the horn-shaped edge 342 protruding from the end face 33a is cut away, and the surgeon has, therefore, a broader view field and can more safely manipulate the hand piece.

One or more intermediate vibration-transmitting members (not shown) can be connected between the horn 3 and the probe 4. In this case, each intermediate vibration-transmitting member must have a length of an integral multiple of λ/2, where λ is the wavelength of the ultrasonic vibration generated by the oscillator 2. The joint between any intermediate vibration-transmitting member and the probe 4 can be one having the same structure as the joint used in the hand piece shown in FIGS. 115 to 117. Due to the use of the intermediate vibration-transmitting members, the probe 4 can have deeper access into a body cavity.

Figure 119:
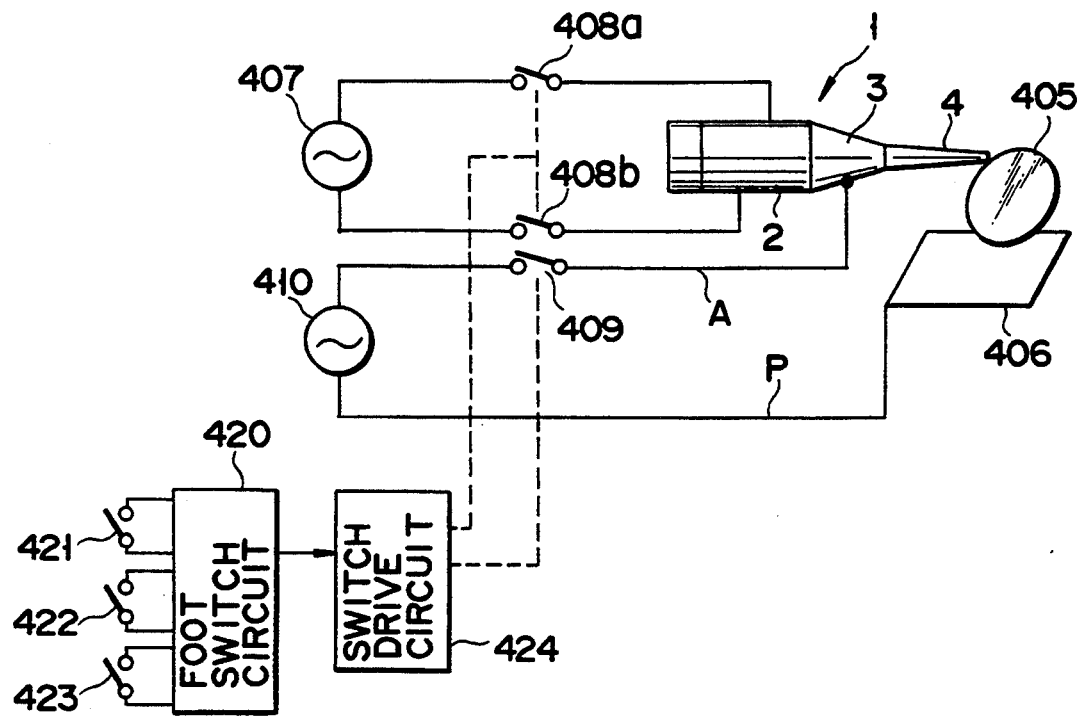
FIGS. 119 and 120 illustrate an ultrasonic treatment apparatus, each related to a 12th embodiment of the present invention, the former being a block diagram of the ultrasonic treatment apparatus, and the latter a switch timing chart.
Figure 120:
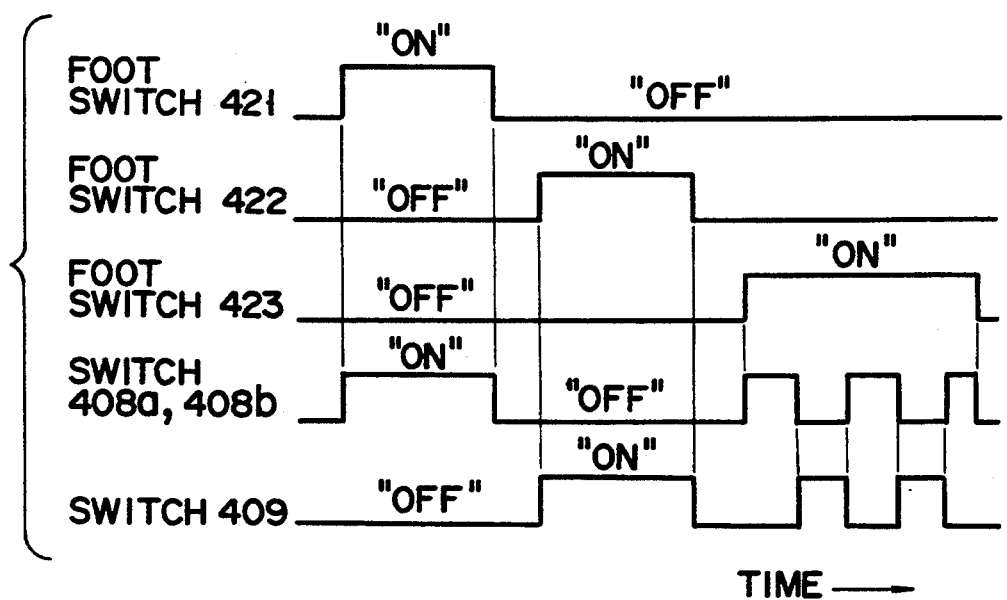

Now, the 12th embodiment of the ultrasonic treatment apparatus according to the present invention is described hereunder. With reference to FIG. 119, a hand piece 1 incorporates an ultrasonic oscillator 2. The ultrasonic oscillator with a plurality of piezoelectric elements laminated one over another transduces electric energy to mechanical energy of vibration.

Further, the hand piece 1 has an ultrasonic conductor comprising a horn 3 and a probe 4, wherein ultrasonic oscillations from the ultrasonic oscillator 2 are amplified by the horn 3 and subsequently transmitted from the probe 4 to a tissue 405 in the area to receive treatment. A patient-side electrode 406 is a brought into and held in contact with the tissue 405 to induce the ultrasonic oscillations thereto.

Meanwhile, an ultrasonic drive circuit 407 generates an ultrasonic signal to drive the ultrasonic oscillator. Coupled to an output terminal of the ultrasonic drive circuit 407 via switches 408a and 408b is said ultrasonic oscillator 2.

Further, the hand piece 1 is connected to one of output terminals of a high-frequency drive circuit through an active cord A and a switch 409. The patient-side electrode 406 is coupled to the other of the output terminals of the high-frequency drive circuit 410 by way of a patient-side cord P. The high-frequency drive circuit 410 generates a high-frequency signal for high-frequency cauterization. The high-frequency drive circuit (410), active cord A, patient-side cord P, and patient-side electrode 406 make up a high-frequency cautery means to feed a high-frequency cauterizing signal to the probe 4.

Coupled to a foot switch circuit 420 are a plurality of foot switches 421, 422, and 423, as well as a switch drive circuit. The foot switch circuit 420 feeds a control signal to the switch drive circuit 424 in response to an on or off condition of each of the foot switches 421, 422, and 423. Following the control signal from foot switch circuit 420, the switch drive circuit actuates said switch 408a and 408b.

Therefore with the foot switch circuit 420 and the switch drive circuit 424 applied, it is feasible that high-frequency cauterization by said high-frequency cautery means, and actuation of said ultrasonic drive circuit 407 are selectively effected or alternately implemented.

This embodiment goes into run, wherein initiating the routine for due treatment by manipulating a control section (omitted from being illustrated) actuates the ultrasonic drive circuit 407, whereby not only an ultrasonic signal is generated therefrom but also a high-frequency signal is formed by the high-frequency drive circuit. Depressing the foot switch 421 under this condition actuate the foot switch circuit (420) and switch drive circuit 424, whereby the switches 408a and 408b turn on. With the switches 408a and 408b on, the ultrasonic signal from the ultrasonic drive circuit 407 is fed to the ultrasonic oscillator 2 of the hand piece 1. This results in driving the ultrasonic oscillator 2, with ultrasonic oscillation to ensue, which is subsequently transmitted to the tissue 405 in the area to undergo treatment via the horn 3 and probe 4, whereby it enables to undertake ultrasonic treatment.

Likewise depressing the foot switch 422 actuates the foot switch circuit 420 and switch drive circuit 424, with a switch 409 turning on thereby. With the switch 409 on, a high-frequency signal output from the high-frequency drive circuit 410 flows into the tissue 405 due to experience treatment through the horn 3, probe 4, and patient-side electrode, thereby enabling to give the tissue 405 the treatment of high-frequency cauterization.

Also depressing the foot switch 423 actuates the foot switch circuit 420 and the switch drive circuit 424, whereby the switches 408a, 408b, and 409 turn on alternately. When the switches 408a and 408b turn on, the ultrasonic signal is fed to the ultrasonic oscillator 2 which is thereby energized, producing ultrasonic oscillations that are then transmitted to the tissue 405 to be given treatment, whereby ultrasonic treatment is effected therein. With the switch 409 on, the high-frequency signal flows in the tissue 405 to receive treatment, thereby high-frequency cautery treatment is implemented therein.

Alternate effectuation of ultrasonic treatment and high-frequency cautery treatment enables to maximize the effect of each category of the above-remarked treatment.

For example, in case where a blood vessel is cut by accident, with bleeding to follow, at the stage of incising an undesired tissue such as a tumor or the like in the performance of ultrasonic treatment, it is practicable to take some measures for immediate stoppage of bleeding and coagulation.

Figure 121:
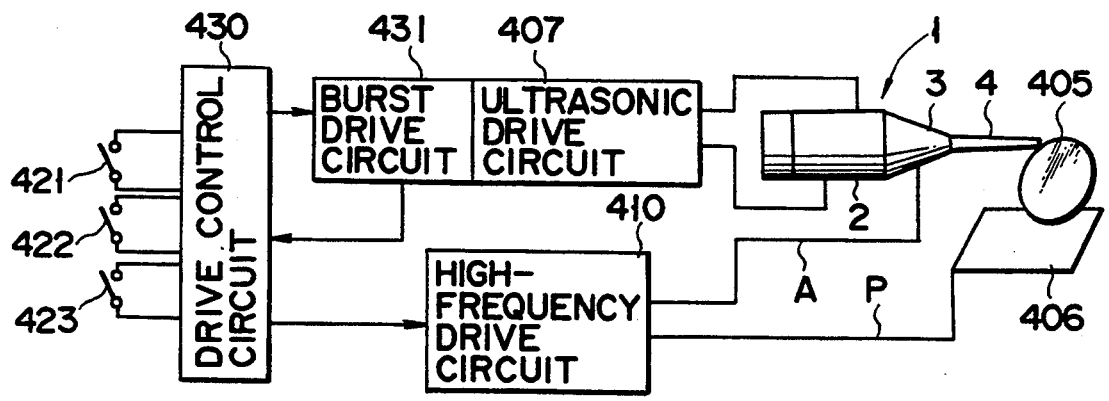
FIGS. 121 through 124 illustrate an ultrasonic treatment apparatus related to a first modification of the 12th embodiment, FIGS. 121 being a block diagram of the ultrasonic treatment apparatus, and FIGS. 122 through 124 each a waveform diagram showing the relation between ultrasonic signal voltage and high-frequency signal voltage.

Next, with reference to FIG. 121, the first modification of the 12th embodiment is described hereunder. In this first modification, the ultrasonic oscillator 2 is coupled directly to the output terminal of the ultrasonic drive circuit.

As shown in FIG. 121, the hand piece 1 is coupled immediately to one of the output terminals of the high-frequency drive circuit 410 via the active cord A. Connected to a drive control circuit 430 are a plurality of foot switches, 421, 422, and 423, plus a burst drive circuit 431 and the high-frequency drive circuit.

The drive control circuit 430 not only control actuation of the burst drive circuit 431 in response to switching-on/-off of each of the foot switches 421, 422, and 423 but also controls energizing the high-frequency drive circuit 410 according to the on/off conditions of the foot switches 421, 422, and 423.

The burst drive circuit 431 burst-energizes (intermittently energizing) the ultrasonic drive circuit 407, and it also feeds to the drive control circuit 430 a signal showing how the former actuates the latter.

Therefore, with the drive control circuit 430, and the burst drive circuit 431 applied, high-frequency cauterization by the high cautery means, and actuation of the ultrasonic drive circuit 407 can be implemented selectively or alternately.

With this first modification, depressing the foot switch 421 causes the drive control circuit 430 to output a signal by which the burst drive circuit 431 is subsequently energized, whereby the ultrasonic drive circuit 407 is burst-energized.

Figure 122:
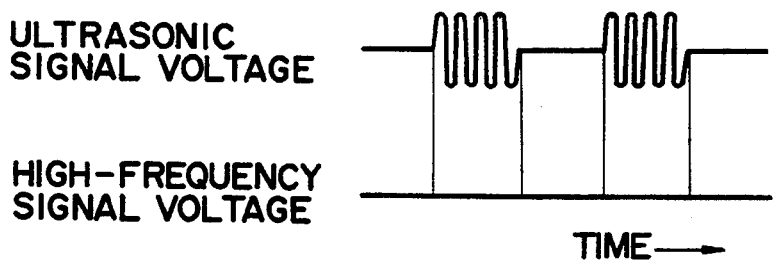

This results in that, as shown in FIG. 122, the ultrasonic drive circuit 407 intermittently outputs the output signal which is then fed to the ultrasonic oscillator 2 of the hand piece. Thereby, the ultrasonic oscillator 2 produces ultrasonic vibrations which are next transmitted to the tissue 405 due to receive treatment through the horn 3 and probe 4, whereby ultrasonic treatment is carried out therein.

Figure 123:
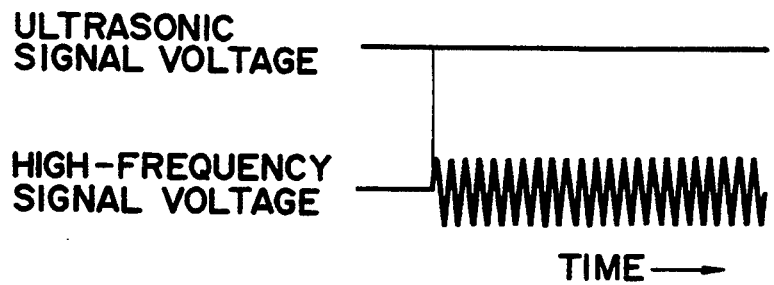

Also depressing the foot switch 422 renders the drive control circuit 430 output a signal, in response to which the high-frequency drive circuit 410 is actuated. As a result, as shown in FIG. 123, the high-frequency drive circuit 410 outputs a high-frequency signal which then flows in the tissue 405 to go through treatment by way of the horn 3, probe 4, and the patient-side electrode, whereby the tissue 405 is ensured of high-frequency cautery treatment.

Similarly depressing the foot switch 423 causes the drive control circuit 430 to send out a signal, according to which the ultrasonic drive circuit 407 is burst-energized, and during an inter-burst drive, the high-frequency drive circuit 410 is actuated.

Figure 124:
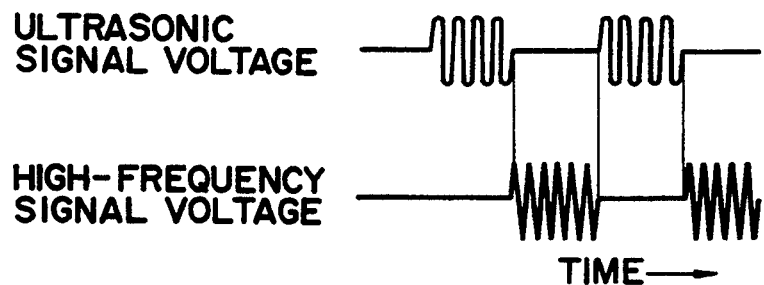

This results in that, as shown in FIG. 124, the ultrasonic and high-frequency signals are given forth alternately. This coincides with another aspect that ultrasonic treatment and high-frequency cautery treatment are implemented alternately, whereby the effect available in each category of these treatments can be maximized, wherein, for example, in the event a blood vessel is cut, incurring bleeding at the stage of incising an undesired tissue such as a tumor or the like midway in the performance of ultrasonic treatment, adequate measures can be taken for immediate stoppage of bleeding and coagulation.

Presented in FIG. 125 is the second modification of the 12th embodiment, wherein, similarly to the preceding modification of the same embodiment, the ultrasonic oscillator 2 is coupled to the output terminal of the ultrasonic drive circuit 407 via the switches 408a and 408b, and wherein the hand piece 1 is connected to the output terminal of the high-frequency drive circuit 410 through the switch 409.

Further, the probe 4 is inset in an inserting section of an electronic endoscope 440 which has a lens 441 at its tip and a CCD (charge coupled diode) 442. A video image obtained through the lens 441 and the CCD 442 is loaded into an image memory via a switch 443.

A control 445 regulates the image memory 444 over image loading and reading-out and has a CRT display coupled thereto. When the probe 4 is insert into the electronic endoscope 440, the hand piece 1 is sustained by a support 447 mounted to the electronic endoscope.

Meanwhile, a switch control circuit 450 controls the switches 408a, 408b, 409 and 443 and runs in a manner that high-frequency cauterization by the high-frequency cautery means, and actuation of the ultrasonic drive circuit 407 will be done alternately.

This second modification is of such a configuration wherein as shown in FIG. 126, initiating the routine for treatment through due manipulations at the control section (omitted from being illustrated) not only actuates the ultrasonic drive circuit 407, causing to generate the ultrasonic signal but also energizes the high-frequency drive circuit 410, likewise causing to generate the high-frequency signal.

Under this condition, the switch control circuit 450 runs in a manner to sequentially turn on the respective switches 408a, 408b, 409, and 443.

Turning on the switches 408a and 408b concurs with feeding the ultrasonic signal to the ultrasonic oscillator 2 which then produces ultrasonic oscillations that are subsequently transmitted to the tissue 405 to receive treatment, whereby ultrasonic treatment is effected therein. Actuating the switch 409 caused the high-frequency signal to flow in the tissue 405 due to go through treatment, whereby high-frequency cautery treatment is implemented therein.

Turning on the switch 443 gives rise to loading into the image memory a video image formed by the lens 441 of the electronic endoscope, and the CCD 442. The video image thus provided has its loading into the image memory 444 properly regulated by the control 445. Also by this control 445, each of the video images thus far stored in the image memory 444 is called out properly on a CRT display 446.

Alternate implementation of ultrasonic treatment and high-frequency cautery treatment as described in the foregoing maximizes the effect of each such categorical treatment. Moreover, electronic endoscope 440 enables to successively observe the phase changing as the tissue goes through treatment, whereby it becomes feasible to do appropriate treatment.

FIG. 127 is a block diagram of a therapeutic system with the ultrasonic treatment apparatus according to a third modification of the 12th embodiment. Presented in each of FIGS. 128 and 129 is an ultrasonic waveform which the ultrasonic apparatus provides.

With reference to FIG. 127, SW-A, for example, is a foot switch 460, SW-B stands for a hand switch 462 furnished for the hand piece 1. An on/off signal of each of these switches is coupled to a switch control circuit 464, thereby the switch control circuit is caused to control the outputs respectively of an ultrasonic drive circuit 466 and a high-frequency drive circuit 468. Each drive circuit output thus controlled is fed to the hand piece 1, whereby the hand piece 1 is rendered workable as an ultrasonic knife or a high-frequency knife.

With such a therapeutic system, each drive circuit output is selectively applied through manipulation of each of these switches on the part of operator.

In an instance of the ultrasonic/high-frequency signal outputting arrangement specified in FIG. 128, turning on the foot switch SW-A (or SW-B) causes the ultrasonic drive circuit 466 to continuously output an ultrasonic signal (US) while depressing on the foot switch SW-B (or SW-A) renders the high-frequency drive circuit 468 intermittently output a high-frequency signal (HF), respectively, through control by the switch control circuit 464.

In another instance given in FIG. 129, the switch control circuit 464 is of such a control arrangement that turning on the foot switch SW-A (or SW-B) gives rise to rendering the ultrasonic drive circuit 466 intermittently output the ultrasonic signal (US) while manipulating on the foot switch SW-B (or SW-A) makes the high-frequency drive circuit 468 continuously output the high-frequency signal (HF).

The high-frequency/ultrasonic signal outputting arrangement may be such that intermittent output of the high-frequency signal or the ultrasonic signal not stems from control by the switch control circuit 464 but results from manipulation of either the foot switch SW-A or SW-B on the part of operator.

In this third modification, it is desired that where the hand piece 1 is applied primarily as an ultrasonic knife, depending on the therapeutic requirements, such an output as given in FIG. 128 be selected while in case the hand piece 1 is used mostly as a high-frequency knife, such an output as shown in FIG. 129 be chosen. This modification is characterized in that the high-frequency/ultrasonic signal outputting arrangement may selectively configured, following the applicative requirements on the part of operator.

FIG. 130 is a block diagram of the therapeutic system according to a 4th modification of the 12th embodiment, and presented in FIG. 131 is a relation between the waveform of each output the on/off condition of each of the above-specified switches.

With regard to FIG. 130, SW-A, for example is a foot switch 470, while SW-B and SW-C are respective hand switches 427 and 473 furnished for the hand piece 1. Each of these switches is coupled to the switch control circuit 474. Working the switch control circuit 474 enables to control the outputs respectively of an ultrasonic drive circuit 476 and a high-frequency drive circuit 478. The output signal from each of these drive circuits is coupled to the hand piece 1, whereby the hand piece 1 is rendered applicable as a high-frequency knife.

For this high-frequency knife, a CUT current to incise the tissue as shown in FIG. 131, and a COAG current to coagulate the blood thereby to stop bleeding are selectively available. The CUT and COAG currents are described later in detail.

FIG. 131 shows a relation between the on/off condition of each of SW-A, SW-B and SW-C, and the respective ultrasonic and high-frequency output signals. In the high-frequency/ultrasonic signal outputting arrangement of this 4th modification, turning on SW-A concurs with an ultrasonic output, switching on SW-B coincides with a high-frequency CUT current output, and manipulating on SW-C entails a high-frequency COAG current output. Each of these outputs is controlled by the switch control circuit 474.

As shown with $US_1$ and $HF_1$ which are quoted in FIG. 131 as one instance of an ultrasonic signal output and a high-frequency signal output, the output of each signal is independently provided. But simultaneously outputting a high-frequency CUT signal ($HF_1$) and an ultrasonic signal ($US_1$) provides a tissue incision capacity far greater than normally required. Therefore, to avoid such trouble, high-frequency/ultrasonic signal output is so controlled that no ultrasonic signal may be output when the high-frequency CUT signal is sent out.

As specified with $US_2$ and $HF_2$ which are quoted in FIG. 131 as another instance of an ultrasonic signal output and a high-frequency signal output, each of these signals is independently output. However, high-frequency/ultrasonic signal output is such controlled that outputting an ultrasonic signal ($US_2$) may not concur with outputting such a high-frequency CUT signal as $HF_2$ given in FIG. 131. With this high-frequency/ultrasonic signal outputting arrangement, the ultrasonic signal and the high-frequency CUT signal are not output at the same time, whereby the same effect as remarked above in the preceding instance is available.

Commonly in these two instances, depending on the therapeutic requirements, the high-frequency CUT signal may be replaced with the high-frequency COAG signal.

A modification of the connection means (connecting member) to couple together the hand piece and the main body respectively of the ultrasonic treatment apparatus according to the present invention is described hereunder.

With the ultrasonic treatment apparatus, connected at the rear end of the hand piece 1 is a liquid supply-suction tube 480. This liquid supply/suction tube is mounted with a HF signal cable 481, and a HF hand switch 483 which can be mounted to and dismounted from the hand piece 1 is fitted to the fore end of the HF signal cable 481. Coupled to the rear end of the HF signal cable is a connector 481a which is joined to the main body (omitted from being illustrated) of the ultrasonic treatment apparatus.

The liquid supply/suction tube has a liquid supply channel 488 and a suction channel and is further provided longitudinally with a recess 484. As shown in FIG. 134, the HF hand switch is arranged such that it can be mounted to a side of the hand piece 1 while the liquid supply/suction tube is of such a configuration as can readily be coupled, in one touch, to a liquid supply/suction receptacle 485 extending from the rear end of the hand piece 1. The rear end of the liquid supply/suction tube 480 branches off into a liquid supply tube 486 and a suction tube 487 which are joined, respectively, to a liquid supply pump and a suction pump (both omitted from being illustrated).

A power supply cord 482 to feed power to the ultrasonic oscillator incorporated in the hand piece 1 extends from the rear end of the hand piece 1, runs along the liquid supply/suction tube 480, and is mounted to the liquid supply/suction tube 480, using a cord clip 482a. Coupled to the rear end of the power cord 482 is a connector 482b which is joined to the main body of the ultrasonic treatment apparatus.

The connection means arranged such as the above allows case of handling the power supply cord and the liquid supply/suction tube over their connection to the hand piece.

Presented in FIGS. 135 through 137 are other modifications of the connection means into which the liquid supply/suction tube are integrated. In one modification quoted in FIG. 135, the liquid supply tube 486, suction tube 487, and HF signal cable 481 are welded or bonded together. In another modification cited in FIG. 136, a dual structural tube is used so that the liquid supply channel 488 and suction channel 489 are coaxially arranged, and the HF signal cable 482 is fitted to the outside periphery of this tube. In a second another modification presented in FIG. 137, the liquid supply/suction tube is molded to-be of an integral structure with the liquid supply channel and suction channel arranged therein in combination, wherein, the HF signal cable 481 is inset within the tube in advance.

The integrated structural tube of such an arrangement as referred to above is assured not only freedom from encountering an entanglement between the respective tubes at the time of their setting but also capability to relieve operator of combing together the liquid supply tube, suction tube, and HF signal cable.

In a further modification illustrated in FIG. 137, each of these tubes is allowed to be of a compact structure.

Illustrated in FIG. 138 is a further modification of the connection means to couple together the hand piece and the main mody of the ultrasonic treatment apparatus. This modification is realized with a power supply cord 490 to deliver power to the ultrasonic oscillator 2 built in the hand piece 1, and a HF active cord 491 combined into one unit as power cord 492. Further, a HF control signal cord 494 coupled to a HF hand switch 493 is provided separately from the power cord 492.

Generally, a dismountable hand switch comes forth in such a configuration with a HF active cord and a control signal cord combined into a unitary cord; therefore, the joint between the unitary cord and hand piece proper is of an electrical connector structure. The result is that the joint not only imposes some restriction over the scope of application but also undergoes certain figuration requirements, resulting in structural complexity.

However, in this modification, the HF control signal cord 494 and the HF active cord 491 are separately provided, whereby the former is not affected by high-frequency noises from the latter and allows ease of mounting and dismounting a hand switch to and from the hand piece proper.

Figure 139A:
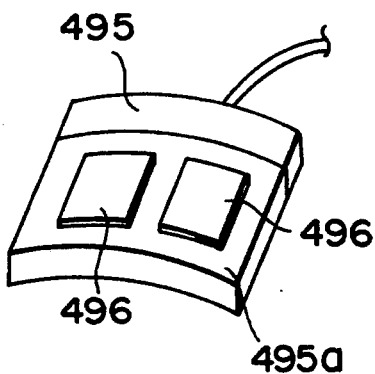
FIGS. 139A and 139B are perspective views showing a modification of a control switch of the ultrasonic treatment apparatus to which the present invention relates.
Figure 139B:
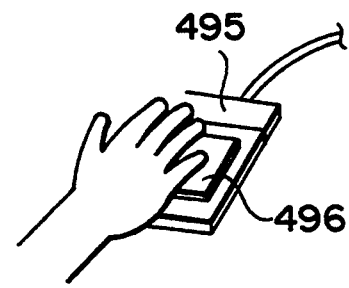
Figure 140:
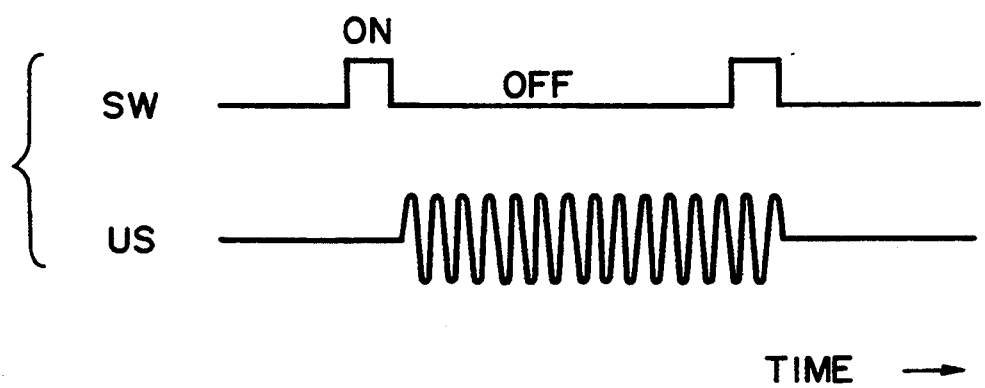
FIG. 140 is a waveform diagram showing the relation between on/off condition of said control switch, and ultrasonic output.

Shown in FIGS. 139A, 139B, and 140 is a pat switch, a modification of a manipulation switch of the ultrasonic treatment apparatus according to the present invention.

The pat switch 495 illustrated in FIG. 139A comprises a switch body 495a and two pressing parts 496. As shown in FIG. 139B, the pat switch can be turned on and off with ease by simply touching these pressing parts 497 alternately. Pressing one pressing part 496 once gives rise to outputting an ultrasonic signal (US) while pressing it twice terminates outputting the ultrasonic signal.

Generally, there is no danger with an ultrasonic knife even with its output maintained on, unless the probe tip is touched. In view of this, the pat switch can provide normal serviceability and is more desired than a foot switch or the like from the standpoint of feasibility of less fatigue imposition on an operator.

Next, a 13th embodiment of the present invention is described hereunder.

Presented in FIGS. 141 through 144 is a 13th embodiment of the present invention, FIG. 141 being an approximate schematic diagram of a surgical operation unit wherein an ultrasonic treatment apparatus. With reference to these figures, 501 is a carriage on which an ultrasonic knife unit 502, an electronic knife 503, and a suction unit 504 are mounted. A connection cable 505 applied as signal input means is coupled between the ultrasonic knife unit 502 and electric knife unit 503 so that a high-frequency treatment signal may be transmitted from the latter to the former.

Coupled to the ultrasonic knife unit 502 through a signal transmission cable 506 is an ultrasonic treatment hand piece 1. The hand piece 1 is equipped with a hand switch 508. Turning on this hand switch 508 energizes the electric knife unit 503 via the ultrasonic knife unit 502, and a high-frequency treatment signal therefrom is input to the hand piece 1. For the ultrasonic knife unit, a foot switch 509 is provided. Depressing on this foot switch actuates the ultrasonic knife unit 502, and an ultrasonic treatment signal therefrom is fed to the hand piece 1. A patient-side electrode 511 is coupled to the electric knife unit 503 by way of an electric cable 510.

As shown in FIG. 142, there comes into existence a drift capacitance Cc with respect to an earth within said ultrasonic knife unit 502. The drift capacitance Cc stays over a physical span defined between a main body of the ultrasonic treatment apparatus and an ultrasonic oscillation circuit 513, normally ranging from some 10 pF to some 100 pF; it is almost impossible to decrement the drift capacitance to 0.

Normally, the high-frequency treatment signal from the electric knife unit passes through a pathologically affected point A of a patient 515 lying on a bed 514 along a path given by a solid line a and flows forward through a patient-side electrode 511. In the presence of this drift capacitance Cc, the high-frequency treatment signal goes into earth, following a path defined with a dotted line b, and then via the bed 514, the signal flows forth, passing through a grounded part such as a contact point B between the patient 515 and the bed 514, and further through the patient-side electrode 511, thus causing a flow of current. This current is called in terms of a shunted current; the greater the drift capacitance Cc, the larger the shunted current. Therefore, should the drift capacitance be large, a thermal burn may sometimes occur at the contact point B by accident. In case where the ultrasonic knife unit 502 and the electric knife unit 503 are combined together, the drift capacitance Cc existing within the ultrasonic knife unit 502 gives rise to criticality in the patient 515 when the high-frequency treatment signal flows through the patient. However, of note is the fact that the 13th embodiment is characterized by a drift capacitance cancel means 516 to eliminate the drift capacitance Cc within the ultrasonic knife unit 502.

The drift capacitance cancel means 516 is arranged such as specified in FIG. 143. With reference to this figure, 517 denotes a parallel resonance circuit made up of a coil L and a capacitor C. The frequency characteristic of this parallel resonance circuit is such that the impedance Z thereof becomes maximal at a resonance frequency fs, as shown in FIG. 144. In this connection, there lies such a background, wherein the parallel resonance circuit works as if no apparent current flows therein with a current Ic flowing through the capacitance C, and a current $I_L$ with a 180°-deviated phase flowing in the coil L counteracting against each other. With this principle applied, the draft capacitance Cc within the ultrasonic knife unit 502 is eliminated. In this case, the resonance frequency fs is obtained according to the following expression:

$$fs = \frac{1}{2\pi \sqrt{LC}}$$

It suffices if the calculated values of fs is matched to the frequency (500 kHz for example) of the high-frequency treatment signal.

As in the foregoing, the drift capacitance cancel means 516 is made up of either the coil L of the coil L and the capacitor C applied in combination, to eliminate the drift capacitance Cc, thus being capable of reducing the shunted current which comes into existence in the presence of the drift capacitance Cc.

The drift capacitance cancel means 516 undergoes no restriction only to such an arrangement disclosed in the 13th embodiment; as arranged in a first modification illustrated in FIG. 145, the drift capacitance cancel means 516 may be of such a configuration comprising either the coil L and a capacitor $C_1$ coupled serially or a parallel resonance circuit 518 with the coil L and a capacitor $C_2$ parallely coupled.

The parallel resonance circuit 518 renders service with such a frequency characteristic as given in FIG. 146. In this case, it suffices if the frequency of the high-frequency treatment signal is matched to a resonance frequency $f_2$.

Though the 13th embodiment is achieved with the drift capacitance Cc cancel means 516 provided between the main body 512 and the ultrasonic oscillation circuit, the same effect as with a second modification illustrated in FIG. 147 is available even when the drift capacitance Cc cancel means 516 is arranged in a joint between the ultrasonic signal transmission cable 506 and the high-frequency signal transmission cable 505. In this case, provision of a drift capacitance cancel means 522 arranged to match the total respectively of a drift capacitance Cc 519 between the joint and the ultrasonic oscillation circuit 513, a drift capacitance Cc 520 between the joint and the main body 512, and a drift capacitance Cc 521 between the main body 512 and the ultrasonic oscillation circuit 513 does good. Where a plurality of high-frequency knife units are used, requiring to change the constant of the element involved in a drift capacitance cancel means from one to another to match each of various frequencies of respective high-frequency treatment signals from individual high-frequency knife units, in such an arrangement as referred to above wherein, as with a third modification presented in FIG. 148, there are provided drift capacitance cancel means 523a and 523b, as well as connectors 524a and 524b respectively for connection cables 505a and 505b, it enables to select the drift capacitance cancel means 523a or 523b by selectively coupling thereto either one of the connectors 524a or 524b.

Provision of such a drift capacitance cancel means to remove the drift capacitance Cc in the ultrasonic knife unit 502 renders practicable to furnish a safe and useful surgical operation unit.

Figure 149:
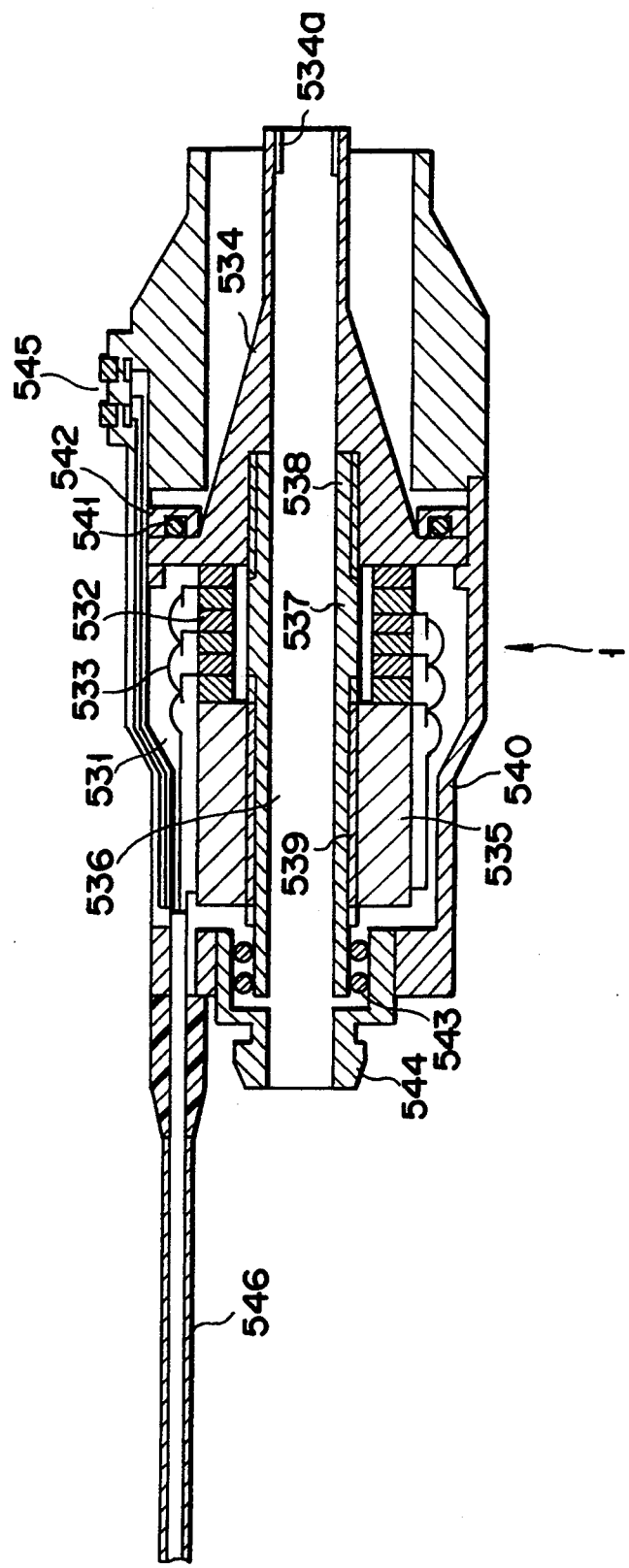
Figure 150:
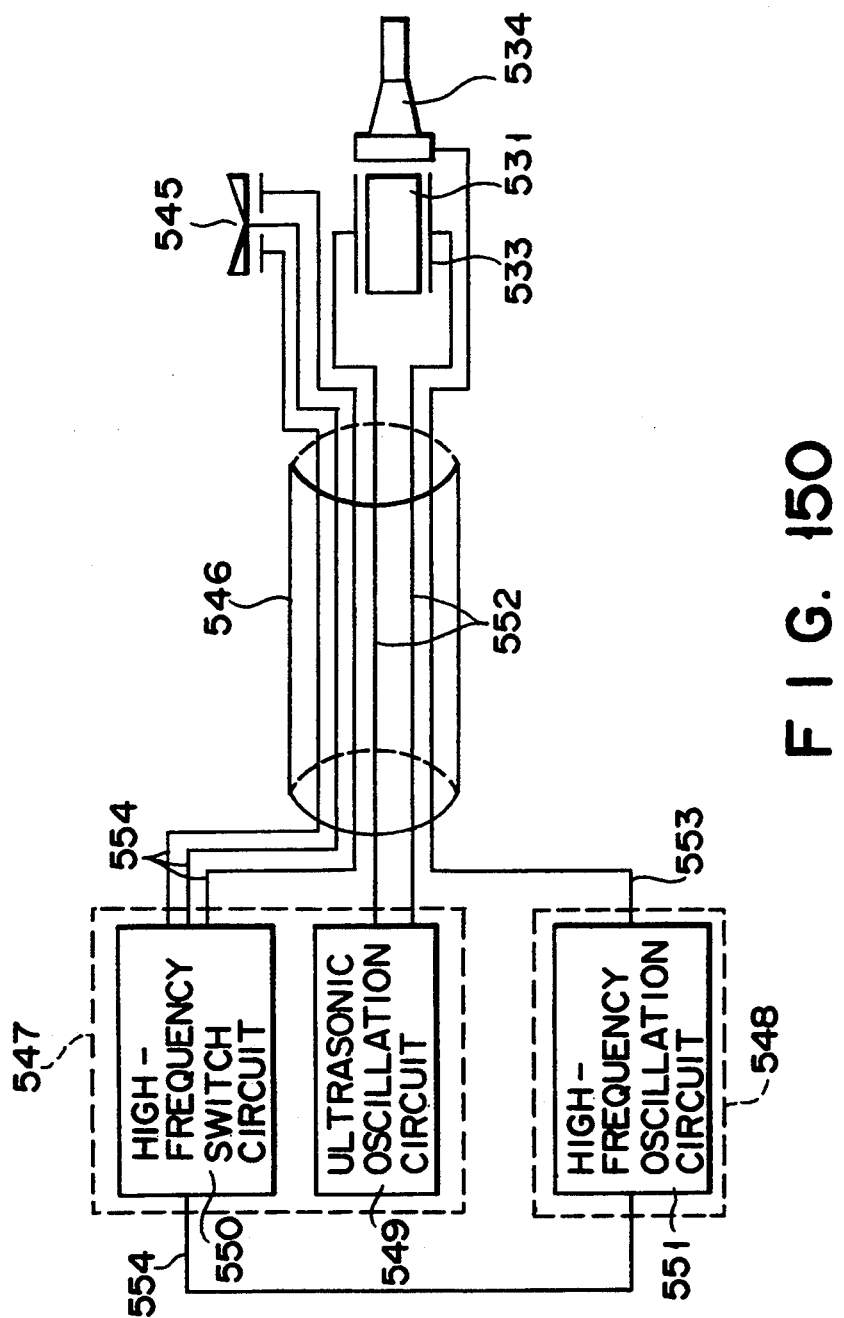

Given in FIGS. 149 through 151 is a modification of the ultrasonic treatment apparatus of the present invention which is characterized by improved maneuverability plus therapeutical efficiency and quickness.

With reference to FIG. 149, 1 stands for a hand piece in which the ultrasonic oscillator 2 is incorporated, which comprises a plurality of piezoelectric elements 532, each made of PZT (zircontitanate), and the same plurality of electrode 533, both of which are staked up alternately one over another. A piezoelectric element-electrode stack thus formed is caught between a force metal block 534 and a rear metal block 535, each provided with transformability (oscillation amplifying capability). A bolt 537 with a suction channel 536 provided along its central axis is screwed in, extending through the fore metal block 534, the piezoelectric element-electrode stack made up of piezoelectric elements 532 and electrode 533, and the rear metal block 535. The fore end part of the bolt 537 has a thread-cut screw for engagement with an internal screw of the fore metal block 534 while the rear end part of said bolt is screwed into engagement with an internal screw of the rear metal block 535. As a consequence, a composite stack comprising a plurality of piezoelectric elements 532 and electrode 533 is firmly held between the fore and rear metal blocks 534 and 535. Said suction channel 536 extends further through the fore metal block 534.

The ultrasonic oscillator 2 thus formed is housed inside a cover 540 and sustainedly locked thereto by a clamp ring 542 with an O-ring which is provided for water-tightness against the fore metal block 534. Further, a pipe sleeve 544 with an O-ring 543 for water-tightness against the rear end of the bolt 537 is sustainedly locked to the cover 540, whereby the hand piece 1 is assured water-tightness. The hand piece 1 is provided a hand switch 545 and has a cord 546 coupled to the electrode 533. 534a provided at the end of the fore metal block 534 is a joint to which the probe (omitted from being illustrated) is coupled.

With reference to FIG. 150, 547 is a ultrasonic knife unit, and 548 an electric knife unit, the ultrasonic knife 547 being provided with an ultrasonic oscillation circuit 549 and a high-frequency switching circuit 550 while the electric knife unit being furnished with a high-frequency oscillation circuit 551.

Said cord 546 contains an ultrasonic oscillator cord 552 to carry an ultrasonic signal from the ultrasonic oscillation circuit 549 to the electrode 533 of the ultrasonic oscillator 2, a high-frequency oscillation circuit 553 to deliver a high-frequency signal from the high-frequency oscillation circuit 551 to the fore metal block 534 of the ultrasonic oscillator 2, and a high-frequency on/off signal cord 554 serving to couple the hand switch 545 to the high-frequency switching circuit 550, and switching on and off the high-frequency signal.

With the ultrasonic treatment apparatus thus arranged as the above, an ultrasonic signal from the ultrasonic oscillation circuit 549 is coupled to the ultrasonic oscillator 2, whereby ultrasonic oscillations propagate through the probe coupled to a joint 534a of the hand piece 1, and midway through the probe, the ultrasonic oscillations have their amplitudes amplified before their travel to the probe tip. Therefore, with the probe tip held in contact with a calculus, it is feasible to break it, or touching the probe tip to a tissue enables to emulsify and incise the tissue. Switching on and off the ultrasonic signal is done by manipulating the foot switch (omitted from being illustrated). In case a tissue incurs bleeding in the performance of ultrasonic treatment, turning on the hand 545 of the hand piece 1 entails a flow of the high-frequency treatment signal through the probe via the fore metal block 534 of the ultrasonic oscillator 2, starting from the high-frequency oscillation circuit 551, whereby the high-frequency signals can be applied to the tissue thereby to stop bleeding.

It is noted that the ultrasonic treatment apparatus arranged such as the above allows simultaneous transmission of the high-frequency and ultrasonic signals without switching from the former to the latter or the vice versa, and permits selecting either a coagulation mode or an incision mode in the cycle of high-frequency treatment through manipulation of the hand switch 545.

Bundling together the ultrasonic oscillator cord 552, high-frequency oscillator cord 553, and high-frequency on/off signal cord 554 as described above results in improving maneuverability of the ultrasonic treatment apparatus and enabling to undertake efficient and quick treatment, compared with a conventional arrangement wherein the respective cords 552, 553, and 554 are maintained unbined.

Further, as shown in FIG. 151, a single cord can be applied commonly as the ultrasonic oscillator cord 552 and high-frequency oscillator cord 553, as illustrated in FIG. 151.

Generally, high-frequency signal transmission with an ultrasonic oscillator on gives an inconvenience that the high-frequency signal from an ultrasonic oscillator cord flows into an ultrasonic oscillation circuit, wherein the signal becomes a noise, whereby the ultrasonic treatment apparatus is sometimes reduced unworkable or sometimes goes into run at such a set-point other than the preselected. FIGS. 152 and 153 each show an arrangement of the ultrasonic treatment apparatus, wherein the above-specified problem is solved. Precisely, the ultrasonic oscillator 2 illustrated in each of these figures is basically identical with those quoted in FIGS. 149 and 150. But this ultrasonic sonic oscillator is different from said each, lacking an insulation ring 557 which said each has between an ultrasonic oscillation unit 556 comprising piezoelectric elements 532 and electrodes 533, and the fore metal block 534, and between the ultrasonic oscillation unit 556 and the rear metal block 535.

In such an arrangement as cited above, the ultrasonic oscillation unit 556 has the fore and rear metal blocks, and the bolt 537 as well electrically insulated. Therefore, high-frequency signal transmission with an ultrasonic oscillator 555 on entails no trouble that the high-frequency signal from the ultrasonic oscillation circuit 549 does not give rise to a noise, whereby the ultrasonic treatment apparatus is assured of stabilized performance. Further of note is another fact that the probe mounted jointly to the ultrasonic oscillation unit 556 and the fore metal block 534 is similarly electrically insulated, leaving behind no chance of a leak current, and with high safety ensured for patients.

FIG. 154 shows a surgical operation system wherein the ultrasonic knife unit and electric knife unit are combined together, and which allows use of a conventional electric knife unit and a like electric knife hand piece.

558 is an ultrasonic knife unit, and 559 an electric knife unit. The ultrasonic knife unit 558 is provided with a connector 561 to couple an ultrasonic knife hand piece 560 thereto, and a connector 563 as well to join an electric knife hand piece to the ultrasonic knife unit. The ultrasonic knife unit 558 and the electric knife unit 559 are coupled together with a connection cable 564. In addition, the electric knife unit is mounted with a pair of electrode plates 565, and the ultrasonic knife unit 585 with a foot switch 566.

It is therefore capable of on-/off-controlling the ultrasonic knife unit 558 by the foot switch, and where a fine blood vessel is cut with bleeding to following in incising a lesion part, while leaving adjacent thick blood vessels and nervous tissues intact, with the tip of the ultrasonic knife hand piece 560 kept energized to transmit ultrasonic oscillations, a switch 560a of the ultrasonic knife hand piece 560 is turned on to give a flow of ultrasonic signals in a tip of the ultrasonic knife hand piece 560, whereby bleeding can be stopped. Meanwhile in case of undertaking incision of a tissue of a body subject to bleeding by use of the electronic knife hand piece 562, instead of the ultrasonic knife hand piece 560, on the occasion of a celiotomy, should bleeding occur, it can be stopped, using the electric knife hand piece 562 coupled to the ultrasonic knife unit 558.

Use of a hand piece applicable commonly for selectively transmitting ultrasonic and high-frequency waves renders provision of a single cord sufficient, gives ease of handling an ultrasonic treatment apparatus, and eliminates the need of additionally providing an electric knife unit.

FIGS. 155 and 156 each show a 14th embodiment of the present invention, FIG. 155 illustrating the approximate arrangement of an surgical operation unit. With reference to these figures, 601 is an ultrasonic knife unit, and 602 an electric knife unit. The ultrasonic knife unit 601 is furnished with a first connector 603, to which an ultrasonic knife hand piece 1 is coupled, as a first hand piece. The ultrasonic knife knife unit 601 effects tissue incision by transmitting ultrasonic oscillations to a probe 4 of the ultrasonic knife hand piece. Said ultrasonic knife unit 601 and an electric knife unit 602 are coupled together with a connection cord 606, and an electric knife signal from the electric knife unit 602 is transmitted via the first connector 603 to the ultrasonic knife hand piece. The ultrasonic knife hand piece 1 is provided with a hand switch 607, whereby manipulating the hand switch enables to on-/off-control the electric knife signal from the probe 4.

Said ultrasonic knife unit 601 is further furnished with a second connector 608, to which an electric knife hand piece 609 is coupled. Normally, however, the ultrasonic knife unit is coupled to a third connector 610 of said electric knife unit 602, whereby said ultrasonic knife unit becomes serviceable as an electric knife. The electric knife unit 602 is provided with a patient-side electrode 611. Since to the third connector 610 is coupled a connection cord 606, the electric knife hand piece 609 is connected to the second connector, whereby manipulating a hand switch 612 mounted to the electric knife hand piece enables to on-/off-control an electric knife signal. The ultrasonic knife unit 601 is further provided with a foot switch 613 to on-/off-control the ultrasonic knife signal.

As a signal in FIG. 156, an ultrasonic oscillator 614 is installed within said ultrasonic knife unit 601 while a high-frequency oscillator 615 is mounted inside the electric knife unit 602. To detect the respective on/off positions of the hand switches 607 and 612, as well as the foot switch 613, each on-/off-controlling the ultrasonic and high-frequency signals which are fed, respectively to the ultrasonic knife hand piece 1, and the electric knife hand piece, output detection circuits 616, 617, and 618 are installed, as respective output detection means, inside the ultrasonic knife unit. More precisely, the output detection circuit 616 is assigned to detect the on- or off-position of the hand switch 607 to output the electric knife signal from the ultrasonic knife hand piece 1, the output detection circuit 617 to detect the on-off-position of the hand switch 609 to output the electric knife signal from the electric knife hand piece 609, and the output detection circuit 618 to detect the on- or off-position of the foot switch 613 to energize the ultrasonic knife hand piece 1 thereby to output ultrasonic oscillations. The consequence of detection done by each of the output detection circuit 616, 617, and 618 is input to a control unit 619 which controls respective switches 620, 621, and 622, each on-/off-controlling the signals to be fed respectively to the ultrasonic knife hand piece 1 and the electric knife hand piece 609.

For example, when the output detection circuit 618 is detecting that ultrasonic excision is under way, using the ultrasonic knife hand piece 1, with the foot switch 613 on, the control unit 619 runs in a manner that attempting the hand switch 612 of the electric knife hand piece 609 will fail to turn on the switch 622, namely resulting in failure of outputting the electric knife signal. In this case if the ultrasonic knife hand piece 1 is such arranged capable of outputting the electric knife signal therefrom that said hand piece provided selective serviceability between an ultrasonic knife and an electric knife, turning on the hand switch 607 of the ultrasonic knife hand piece 1 actuates the switch 623 simultaneously with turning on the switch 621, whereby the electric knife signal is also output from the ultrasonic knife hand piece 1.

On the other hand, where the output detection circuit 617 is detecting that the output from the electric knife hand piece 609 is applied as an electric knife signal with the hand switch 612 on, which is of said hand piece, and also with the switches 622 and 623 subsequently on, the control unit 619 operates so that turning on the hand switch 607 of the ultrasonic knife hand piece 1 will fail to actuate the switch 621, and turning on the foot switch likewise fails to turn on the switch 620, whereby the ultrasonic knife hand piece 1 is reduced unserviceable.

As in the foregoing, hand piece control is such that the hand piece other than that held in the hand of an operator does not give an output, with higher safety thus assured.

The ultrasonic knife hand piece 1 is serviceable as an ultrasonic and an electric knife. Further, of particular note is the fact that the ultrasonic knife hand piece 1 can output both the ultrasonic and electric signals simultaneously, and also that the electric knife hand piece 609 is normally workable while said hand piece is kept coupled to the second connector 608 of the ultrasonic knife unit 601, whereby the operator is allowed to quickly adapt himself to the circumstances of operation in progress. According to this 14th embodiment, the ultrasonic knife hand piece of such an arrangement allowing to control the output by a hand switch is connectable to an existing electric knife hand piece, proving wide universality of application as a system.

Presented in FIG. 157 is a first modification of the 14th embodiment. In this modification, the ultrasonic knife unit 601 is furnished with an output detection circuit 625 to detect the on-/off-position of the hand switch 607 of the ultrasonic knife hand piece 1, and an output detection circuit 626 to detect the on/off-position of the hand switch 612 of the electric knife hand piece 609. A prohibit signal line 627 to transmit a signal of hand switch on-/off-position between each two of the output detection circuits 625 and 626, and an ultrasonic oscillator 614 is also coupled to the ultrasonic knife unit. Further, the ultrasonic knife unit 601 is provided with relay circuits 628 and 629 so that the electric knife signal from a high-frequency oscillator 615 inside the electric knife unit 602 can selectively output to the ultrasonic knife hand piece 1 and electric knife hand piece 609. Namely, the relay circuits 628 and 629 have first contacts 628a and 629a, and second contacts 628b and 629b, respectively, and these relay circuits are so connected that they will be on-/off-controlled, respectively by said output detection circuits 625 and 626.

Each of the output signals respectively from the output detection circuits 625 and 626 is fed to an OR circuit 630, and the output thereof is coupled to an output control unit 631 of the electric knife unit 602 via the connection cord 606 in a manner that the electric knife signal from a high-frequency oscillator 615 will be on-/off-controlled by the output control unit 631. It is noted that the ultrasonic oscillator is on-/off-controllable by a foot switch (omitted from being illustrated) or the like.

Therefore, turning on the hand switch 612 of the electric knife hand piece 609 actuates the output detection circuit 626, whereby the relay circuit 629 is driven and the output control unit 631 within the electric knife unit 602 also goes into run with a hand switch 612 on signal by way of the OR circuit 630, with actuation of the high-frequency oscillator 615 to ensue. With the electric knife signal output from the high-frequency oscillator 615 on, the electric knife hand piece 609 output the electric knife signal. Namely, actuating the relay circuit 629 coincides with inflicting an electric knife signal path a double interruption by the first contact 628a of the relay circuit 628 and the second contact 629b of the relay circuit 629. As long as the output detection circuit 626 is actuated, a prohibit signal is kept fed respectively to the output detection circuit 625 and the ultrasonic oscillator 614, whereby neither the ultrasonic knife signal nor the electric knife signal is output to the ultrasonic knife hand piece.

Meanwhile, manipulating on the hand switch 607 of the ultrasonic knife hand piece 1 actuates the output detection circuit 625, whereby the relay circuit 628 goes into run. In this case the electric knife signal to be fed to the electric knife hand piece 609 undergoes a double interruption by the first contact 629a of the relay circuit 629, and also by the contact 628b of the relay circuit 628. While the output detection circuit 625 or the ultrasonic oscillator 614 remains on, the prohibit signal is delivered to the output detection circuit 626, thereby the function of the hand switch 612 of the electric knife hand piece 609 is nullified, resulting in reducing the electric knife hand piece 609 unserviceable even with the hand switch 612 actuated.

With such an arrangement, the electric knife signal is never transmitted to both hand pieces but is coupled to either one of the two hand pieces, and the relay circuit is of a double contact configuration, whereby though the electric knife signal is output from the ultrasonic knife hand piece 1 when manipulating on the hand switch 607 even with the relay circuit 628 gone into abnormality, and subsequently getting maintained on, there is no chance that the ultrasonic knife hand piece 1 outputs the electric knife signal by accident at the time the hand switch 612 is actuated.

Quoted in FIG. 158 is a second modification of the 14th embodiment, wherein the output detection circuits to respectively detect the on-/off-position of the hand switch 607 of the ultrasonic knife hand switch 1, and that of the hand switch 612 of the electric knife hand piece 609 are different from those used in the preceding modification.

The ultrasonic knife hand piece 1 and the electric knife hand piece 609 are furnished respectively with a pair of hand switches; a pair of switches 607a (COAG current) and 607b (CUT current) goes with the former, and a pair of switches 612a (COAG current) and 612b (CUT current) with the latter. With reference to FIG. 158, 632 denotes a 4-input NAND circuit and 633 for a 2-input AND circuit. In the 2nd modification, there are provided four 4-input NAND circuits 632, and each two of these NAND circuits have their input and outputs coupled, in a stagger mode, to their counterparts. There are also provided four 2-input NAND circuits 633. Two of the outputs from each said 4-input NAND circuit 632 are applied in combination for OR-gating.

Therefore, the above-remarked 4-input NAND and 2-input NAND circuits are thus given priority of their outputs over the hand switches 607a, 607b, 612a and 612b; for example, turning on the hand switch 607a causes one of said 4-input NAND circuits to give an O-output which prohibits functioning remaining three 4-input NAND circuits 632. Namely, even if the hand switches 607b, 612a and 612b are turned on while the hand switch 607a is maintained on, the O-output is kept on, with the remaining three 4-input NAND circuit failing to give their output. Such being the case, no more than one out of O-, P-, Q-, and R-output from the respective 4-input NAND circuits 632 is allowed be sent out. OR-gating one of these outputs enables to select the categories of the output from the ultrasonic knife hand piece 1 and the electric knife hand piece 609 to which an OR-gated O-, P-, Q-, or R-output is coupled. The result is that each of these hand switches is assured of freedom from double-actuation criticality.

FIGS. 159 and 160 each show a third modification of the 14th embodiment, wherein the electric knife output selection circuit is different from that involved in the previous modification.

In the third modification, the ultrasonic knife unit 601 is provided with relay circuits 634 and 635, with which as to the destination of the electric knife signal, either the ultrasonic knife hand piece 1 or the electric knife hand piece 609 is selected. A relay circuit 636 on-/off-controls the electric knife signal output while a control unit 637 controls said relay circuits 634, 635 and 636.

Therefore, turning on the hand switch 607 to have the ultrasonic knife hand piece output the electric knife signal makes a contact 634a of the relay circuit 634 simultaneously with energizing said hand piece, whereby an ultrasonic knife signal path to the ultrasonic knife hand piece 1 is established. At a certain time (t) thereafter, the relay 636 closes, actuating the electric knife unit 602, thereby the electric knife signal is output therefrom. Turning off the hand switch 607 open the relay 636 simultaneously with energizing the ultrasonic knife hand piece, and a certain time (t') thereafter, breaks a contact 643a of the relay 634.

Turning on the hand switch 612 of the electric knife hand piece 609 likewise above makes a contact 635a of the relay circuit 635 simultaneously with energizing said hand piece, whereby an electric knife signal path to the electric knife hand piece 609 is set up, followed by outputting the electric knife signal. Turning off the hand switch concurs with cutting out the electric knife signal path.

In this way, the contacts 634a and 635b respectively of the relay circuits 634 and 635, each on-/off-controlling a high-voltage, large-current electric knife signal are protected. As a result, the contacts 634a and 635a are ensued freedom from the trouble of undergoing accidental welding.

It is understood that the present invention is not limited to the above-cited embodiments and their modifications but can be embodied in various other modifications within the spirit of the present invention, and the scope of the claims appended hereunder.

What is claimed is:

1. An ultrasonic treatment kit comprising:
   at least one hand piece having ultrasonic oscillation means for generating ultrasonic vibration;
   a plurality of probes attachable to said at least one hand piece, and a selected one of said plurality of probes being attached to a designated one of said at least one hand piece so that the selected probe transmits the ultrasonic vibration generated by said one designated hand piece attached thereto;
   ultrasonic drive means connected to said one designated hand piece, for driving said ultrasonic oscillation means; and
   means for regulating each said ultrasonic oscillator means in such a manner that the ultrasonic vibration generated by the ultrasonic oscillator means is maintained constant for each probe from among said plurality of probes attached to said one designated hand piece.

2. The apparatus according to claim 1, further comprising water-supplying means for supplying cooling water to cool said probes.

3. The apparatus according to claim 2, wherein said ultrasonic drive means has adjusting means for adjusting the amplitude of the high-frequency voltage applied to said ultrasonic oscillation means and also the flow rate at which said water-supplying means supplies the cooling water to cool said selected one of said plurality of probes.

4. The apparatus according to claim 1, wherein said ultrasonic drive means has power-supplying means for supplying electric power to said ultrasonic oscillation means.

5. The apparatus according to claim 1, wherein said ultrasonic drive means has a resonance-point drive circuit for detecting a resonant frequency of said ultrasonic oscillation means and the selected one of said plurality of probes which is attached to said one designated hand piece, and drives said ultrasonic oscillation means at the resonant frequency.

6. The apparatus according to claim 1, wherein said ultrasonic drive means has display means for displaying a driven condition of said one designated hand piece.

7. The apparatus according to claim 1, wherein said ultrasonic drive means has probe-identifying means for identifying the selected one of said plurality of probes attached to said one designated hand piece, when said one designated hand piece is connected to said ultrasonic drive means.

8. The apparatus according to claim 7, further comprising a set-up switch for supplying a signal to said probe-identifying means when the selected one of said plurality of probes is connected to said one-designated hand piece, whereby said probe-identifying means starts identifying the selected probe.

9. The apparatus according to claim 7, which further comprises a connector for connecting said one designated hand piece and said ultrasonic drive means together, and in which said probe-identifying means is provided within this connector.

10. The apparatus according to claim 1, wherein said one designated hand piece has a suction channel, said selected one of said plurality of probes has a suction channel, and which further comprises suction means for applying suction force through these suction channels, and suction-mode setting means for setting an output mode for the suction means.

11. The apparatus according to claim 1, wherein said ultrasonic drive means has a foot switch.

12. The apparatus according to claim 1, wherein said one designated hand piece has a suction channel, said selected one of said plurality of probes has a suction channel, and which further comprises suction means for applying suction force through these suction channels, and release means for releasing the suction force.

13. The apparatus according to claim 1, wherein said one designated hand piece has a suction channel, said selected one of said plurality of probes has a suction channel, and which further comprises a suction system for generating and applying suction force through these suction channels.

14. The apparatus according to claim 13, wherein said suction system has a suction bottle for containing fluids supplied under the suction force from a distal end of said selected probe.

15. The apparatus according to claim 13, wherein said one designated hand piece has a connector communicating with said suction channels.

16. The apparatus according to claim 1, wherein said one designated hand piece has a horn with an output end portion producing an ultrasonic vibration, said output end portion being inclined to the longitudinal axis of said horn.

17. The apparatus according to claim 1, wherein said one designated hand piece has a horn for amplifying the ultrasonic vibration generated by said ultrasonic oscillation means, said horn being straight.

18. The apparatus according to claim 1, wherein said water-supplying means has a water-supplying channel, and said one designated hand piece has a water inlet cap communicating with the water-supplying channel.

19. The apparatus according to claim 1, further comprising a cover covering said ultrasonic oscillation means and said selected one of said plurality of probes, and support means for supporting and positioning said ultrasonic oscillation means and said selected probe with respect to said cover, at a loop of third harmonic waves, when said ultrasonic oscillation means imparts ultrasonic vibration to said selected probe.

20. The apparatus according to claim 1, wherein said one designated hand piece has a cover covering said ultrasonic oscillation means, and said ultrasonic oscillation means has a flange at a node of ultrasonic vibration, and an elastic member interposed between the flange and said cover, for fastening the flange to said cover.

21. The apparatus according to claim 1, wherein said designated probe hand piece has a rear end portion and fluid connectors protruded from the rear end portion.

22. The apparatus according to claim 1, wherein each of said plurality of probes have a length which is an integral multiple of half the wavelength of the ultrasonic vibration transmitted from said ultrasonic oscillation means.

23. The apparatus according to claim 1, wherein at least one of said plurality of probes has a bent portion.

24. The apparatus according to claim 1, wherein at least one of said plurality of probes is straight.

25. The apparatus according to claim 1, wherein each of said plurality of probes comprises a thin shaft and a tip fused to the thin shaft.

26. The apparatus according to claim 1, wherein each of said plurality of probes has at least a distal end portion thereof substantially free of oxide coating and substantially free of cracks and scars.

27. The apparatus according to claim 1, wherein each of said plurality of probes has surfaces thereof substantially free of oxide coating and substantially free of cracks and scars.

28. The apparatus according to claim 1, wherein said plurality of probes have different transformation ratios of ultrasonic waves suitable for specific purposes.

29. The apparatus according to claim 1, wherein said plurality of probes are made of titanium alloy.

30. The apparatus according to claim 1, further comprising a sheath covering the circumferential surface of the probe attached to said one designated hand piece.

31. The apparatus according to claim 30, wherein the distal end of said plurality of selected probes projects from a distal end of said sheath.

32. The apparatus according to claim 1, further comprising probe-guiding means for guiding the selected one of said plurality of probes into a body cavity.

33. The apparatus according to claim 32, wherein said probe-guiding means is an endoscope having observation means.

34. The apparatus according to claim 32, wherein said selected probe is straight, and said probe-guiding means has an adapter means capable of projecting for a controllable distance.

35. An ultrasonic treatment kit comprising:
   a plurality of hand pieces of different types, each having ultrasonic oscillation means for generating ultrasonic vibration;
   at least one probe attachable to said plurality of hand pieces, and a selected one of said plurality of hand pieces being attached to a designated one of said at least one probe, which probe transmits the ultrasonic vibration generated by the ultrasonic oscillation means of said selected one of said plurality of hand pieces attached thereto;
   ultrasonic drive means connected to the selected hand piece, for driving said ultrasonic oscillation means of the selected hand piece; and
   means for regulating said ultrasonic oscillator means of said plurality of hand pieces in such a manner that the ultrasonic vibration generated by the ultrasonic oscillator means of said selected hand piece is maintained constant for said one designated probe attached to said selected hand piece.

36. The apparatus according to claim 35, further comprising water-supplying means for supplying cooling water to cool said probe.

37. The apparatus according to claim 36, wherein said ultrasonic drive means has adjusting means for adjusting the amplitude of the high-frequency voltage applied to said ultrasonic oscillation means and also the flow rate at which said water-supplying means supplies the cooling water to cool said one designated probe.

38. The apparatus according to claim 35, wherein said ultrasonic drive means has power-supplying means for supplying electric power to said ultrasonic oscillation means.

39. The apparatus according to claim 35, wherein said ultrasonic drive means has a resonance-point drive circuit for detecting a resonant frequency of said ultrasonic oscillation means and said at least one probe, and drives said ultrasonic oscillation means at the resonant frequency.

40. The apparatus according to claim 35, wherein said ultrasonic drive means has display means for displaying a driven condition of said selected one of said plurality of hand pieces.

41. The apparatus according to claim 35, wherein said ultrasonic drive means has probe-identifying means for identifying the one designated probe attached to one of said hand pieces, which is connected to said ultrasonic drive means.

42. The apparatus according to claim 41, further comprising a set-up switch for supplying a signal to said probe-identifying means when the one designated probe is connected to said selected one of said plurality of hand pieces, whereby said probe-identifying means starts identifying the one designated probe.

43. The apparatus according to claim 41, which further comprises a connector for connecting said selected one of said plurality of hand pieces to said ultrasonic drive means, and in which said probe-identifying means is provided within this connector.

44. The apparatus according to claim 35, wherein each of said plurality of hand pieces has a suction channel, said one designated probe has a suction channel, which further comprises suction means for applying suction force through these suction channels, and suction-mode setting means for setting an output mode for the suction means.

45. The apparatus according to claim 35, wherein said ultrasonic drive means has a foot switch.

46. The apparatus according to claim 35, wherein each of said plurality of hand pieces has a suction channel, said one designated probe has a suction channel, and which further comprises suction means for applying suction force through these suction channels, and release means for releasing the suction force.

47. The apparatus according to claim 35, wherein each of said plurality of hand pieces has a suction channel, said one designated probe has a suction channel, and which further comprises a suction system for generating and applying suction force through these suction channels.

48. The apparatus according to claim 47, wherein said one designated suction system has a suction bottle for containing fluids supplied under the suction force from a distal end of said probe.

49. The apparatus according to claim 47, wherein said hand piece has a suction cap communicating with said suction channels.

50. The apparatus according to claim 35, wherein said selected one of said plurality of hand pieces has a horn with an output end portion producing an ultrasonic vibration, said output end portion being inclined to the longitudinal axis of said horn.

51. The apparatus according to claim 35, wherein each of said plurality of hand pieces has a horn for amplifying the ultrasonic vibration generated by said ultrasonic oscillation means, said horn being straight.

52. The apparatus according to claim 35, wherein said water-supplying means has a water-supplying channel, and each of said plurality of hand pieces has a water inlet cap adapted for communicating with the water-supplying channel.

53. The apparatus according to claim 35, further comprising a cover covering said one designated probe and the ultrasonic oscillation means of said selected one of said plurality of hand pieces connected to said one designated probe, and support means for supporting and positioning said ultrasonic oscillation means and said one designated probe with respect to said cover, at a loop of third harmonic waves, when said ultrasonic oscillation means imparts ultrasonic vibration to said one designated probe.

54. The apparatus according to claim 35, wherein each of said plurality of hand pieces has a cover covering said ultrasonic oscillation means, and said ultrasonic oscillation means has a flange at a node of ultrasonic vibration, and an elastic member interposed between the flange and said cover, for fastening the flange to said cover.

55. The apparatus according to claim 35, wherein said selected one of said plurality of hand pieces has a rear end portion and fluid connectors protruded from the rear end portion.

56. The apparatus according to claim 35, wherein said designated probe has a length which is an integral multiple of half the wavelength of the ultrasonic vibration transmitted from any one of said ultrasonic oscillation means in said plurality of hand pieces.

57. The apparatus according to claim 35, wherein said designated probe has a bent portion.

58. The apparatus according to claim 35, wherein said designated probe is straight.

59. The apparatus according to claim 35, wherein said designated probe comprises a thin shaft and a tip fused to the thin shaft.

60. The apparatus according to claim 35, wherein said designated probe has at least a distal end portion thereof substantially free of oxide coating and substantially free of cracks and scars.

61. The apparatus according to claim 35, wherein said designated probe has surfaces thereof substantially free of oxide coating and substantially free of cracks and scars.

62. The apparatus according to claim 35, wherein said designated probe has a transformation ratio of ultrasonic wave suitable for a specific purpose.

63. The apparatus of claim 35, wherein said designated probe is made of titanium alloy.

64. The apparatus according to claim 35, further comprising a sheath covering the circumferential surface of the one designated probe attached to the selected one of said plurality of hand pieces.

65. The apparatus according to claim 64, wherein the distal end of said one designated probe projects from a distal end of said sheath.

66. The apparatus according to claim 35, further comprising probe-guiding means for guiding said one designated probe into a body cavity.

67. The apparatus according to claim 66, wherein said probe-guiding means is an endoscope having observation means.

68. The apparatus according to claim 66, wherein said one designated probe is straight, and said probe-guiding means has an adapter means capable of projecting for a controllable distance.

69. The apparatus according to claim 1, wherein said ultrasonic drive means has a manual switch.

70. The apparatus according to claim 35, wherein said ultrasonic drive means has a manual switch.

* * * * *